US012759979B2

(12) United States Patent
Weissman

(10) Patent No.: US 12,759,979 B2
(45) Date of Patent: Oct. 13, 2026

(54) CRYSTALLINE FORMS OF 2-(TERT-BUTOXY)-4-(3-METHYL-3-(5-(METHYLSULFONYL)ISOINDOLIN-2-YL)BUTYL)PHENOL FUMARATE SALT

(71) Applicant: Cognition Therapeutics, Inc., Purchase, NY (US)

(72) Inventor: Steven A. Weissman, Short Hills, NJ (US)

(73) Assignee: Cognition Therapeutics, Inc., Purchase, NY (US)

( * ) Notice: Subject to any disclaimer, the term of this patent is extended or adjusted under 35 U.S.C. 154(b) by 0 days.

(21) Appl. No.: 19/563,468

(22) Filed: Mar. 11, 2026

(65) Prior Publication Data

US 2026/0200848 A1 Jul. 16, 2026

Related U.S. Application Data

(63) Continuation of application No. PCT/US2025/047026, filed on Sep. 18, 2025.

(60) Provisional application No. 63/696,061, filed on Sep. 18, 2024.

(51) Int. Cl.

| | |
|---|---|
| ***C07D 209/44*** | (2006.01) |
| ***A61K 31/4035*** | (2006.01) |
| ***C07C 57/15*** | (2006.01) |

(52) U.S. Cl.

CPC ........ *C07D 209/44* (2013.01); *A61K 31/4035* (2013.01); *C07C 57/15* (2013.01); *C07B 2200/13* (2013.01)

(58) Field of Classification Search

CPC .... C07D 209/44; A61K 31/4035; C07C 57/15

USPC .......................................................... 514/416

See application file for complete search history.

(56) References Cited

U.S. PATENT DOCUMENTS

| | | | |
|---|---|---|---|
| 9,796,672 | B2 | 10/2017 | Rishton et al. |
| 10,207,991 | B2 | 2/2019 | Rishton et al. |
| 10,611,728 | B2 | 4/2020 | Rishton et al. |
| 11,691,947 | B2 | 7/2023 | Rishton et al. |
| 12,466,795 | B2 | 11/2025 | Rishton et al. |

FOREIGN PATENT DOCUMENTS

| | | | |
|---|---|---|---|
| WO | 2015116923 | A1 | 8/2015 |
| WO | 2022197885 | A1 | 9/2022 |
| WO | 2024020059 | A1 | 1/2024 |
| WO | 2026064543 | A1 | 3/2026 |

OTHER PUBLICATIONS

International Search Report and Written Opinion for application No. PCT/US2025/047026 dated Nov. 20, 2025.

Weissman et al., "Commercial Route Development of Sigma-2 Receptor Modulator, CT1812 Leveraging Photoflow, and HTS Technologies—Supplemental Information," Organic Process Research & Development, Jan. 29, 2025, 29(2):1-29.

Weissman et al. "Commercial Route Development of Sigma-2 Receptor Modulator, CT1812 Leveraging Photoflow, and HTS Technologies" Jan. 29, 2025, Organic Process Research & Development 29(2):373-388.

*Primary Examiner* — Kahsay Habte

(74) *Attorney, Agent, or Firm* — DLA Piper LLP (US)

(57) ABSTRACT

The present disclosure describes crystalline forms of 2-(tert-butoxy)-4-(3-methyl-3-(5-(methylsulfonyl)isoindolin-2-yl) butyl)phenol fumarate salts and pharmaceutical compositions of same. Also described are methods of using the crystalline forms treating Alzheimer's Disease, Dementia with Lewy Bodies and Dry age-related macular degeneration in a subject in need thereof, comprising administering the crystalline form to the subject. Methods of making the solid forms are also described.

30 Claims, 42 Drawing Sheets

CRYSTALLINE FORMS OF 2-(TERT-BUTOXY)-4-(3-METHYL-3-(5-(METHYLSULFONYL)ISOINDOLIN-2-YL)BUTYL)PHENOL FUMARATE SALT

CROSS-REFERENCE TO RELATED APPLICATIONS

This Application is a continuation under 35 U.S.C. § 111(a) of International Patent Application No. PCT/US2025/047026 filed on Sep. 18, 2025, which claims priority to U.S. Provisional Application No. 63/696,061 filed on Sep. 18, 2024, which are incorporated herein by reference in their entirety.

GOVERNMENT INTEREST

This invention was made with government support under R01AG065248 awarded by the National Institute on Aging of the National Institute of Health. The government has certain rights in this invention.

SUMMARY

In some aspects, the techniques described herein relate to 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) including characteristic 2θ peaks at 9.69, 16.51, 17.23, 19.02, 25.10, and 26.49° (±0.2°).

In some aspects, the techniques described herein relate to 2-(t-butoxy)-4-(3-methyl-3-(5-(methylsulfonyl)isoindolin-2-yl)butyl)phenol mono-fumarate salt crystal form A characterized by an X-ray powder diffraction (XRPD) pattern including characteristic 2θ peaks at 5.23, 16.84, 17.41, 20.72 and 25.55° (±0.2°).

In some aspects, the techniques described herein relate to 2-(t-butoxy)-4-(3-methyl-3-(5-(methylsulfonyl)isoindolin-2-yl)butyl)phenol mono-fumarate salt, acetone solvate crystal form B characterized by an X-ray powder diffraction pattern (XRPD) including characteristic 2θ peaks at 6.09, 20.79, 21.05, 25.24, and 25.86° (±0.2°).

In some aspects, the techniques described herein relate to 2-(t-butoxy)-4-(3-methyl-3-(5-(methylsulfonyl)isoindolin-2-yl)butyl)phenol mono-fumarate salt, acetonitrile solvate crystal form C characterized by an X-ray powder diffraction pattern (XRPD) including characteristic 2θ peaks at 5.27, 16.47, 17.65, 19.36, and 21.09° (±0.2°).

In some aspects, the techniques described herein relate to 2-(t-butoxy)-4-(3-methyl-3-(5-(methylsulfonyl)isoindolin-2-yl)butyl)phenol mono-fumarate salt crystal form D characterized by an X-ray powder diffraction pattern (XRPD) including characteristic 2θ peaks at 5.24, 17.06, 17.49, and 27.12° (±0.2°).

In some aspects, the techniques described herein relate to 2-(t-butoxy)-4-(3-methyl-3-(5-(methylsulfonyl)isoindolin-2-yl)butyl)phenol mono-fumarate salt, hemi-hydrate crystal form F characterized by an X-ray powder diffraction pattern (XRPD) including characteristic 2θ peaks at 5.20, 12.51, 16.84, 20.84, and 25.14° (±0.2°).

In some aspects, the techniques described herein relate to a pharmaceutical composition comprising crystal form E of 2-(t-butoxy)-4-(3-methyl-3-(5-(methylsulfonyl)isoindolin-2-yl)butyl)phenol hemi-fumarate dihydrate salt according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form E of 2-(t-butoxy)-4-(3-methyl-3-(5-(methylsulfonyl)isoindolin-2-yl)butyl)phenol hemi-fumarate dihydrate salt according to any aspect described herein In some aspects, the techniques described herein relate to a pharmaceutical composition comprising crystal form A of 2-(t-butoxy)-4-(3-methyl-3-(5-(methylsulfonyl)isoindolin-2-yl)butyl)phenol mono-fumarate salt according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form A of 2-(t-butoxy)-4-(3-methyl-3-(5-(methylsulfonyl)isoindolin-2-yl)butyl)phenol mono-fumarate salt according to any aspect described herein.

In some aspects, the techniques described herein relate to a pharmaceutical composition comprising crystal form B of 2-(t-butoxy)-4-(3-methyl-3-(5-(methylsulfonyl)isoindolin-2-yl)butyl)phenol mono-fumarate salt, acetone solvate according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form B of 2-(t-butoxy)-4-(3-methyl-3-(5-(methylsulfonyl)isoindolin-2-yl)butyl)phenol mono-fumarate salt, acetone solvate according to any aspect described herein In some aspects, the techniques described herein relate to a pharmaceutical composition comprising crystal form C of 2-(t-butoxy)-4-(3-methyl-3-(5-(methylsulfonyl)isoindolin-2-yl)butyl)phenol mono-fumarate salt, acetonitrile solvate according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form C of 2-(t-butoxy)-4-(3-methyl-3-(5-(methylsulfonyl)isoindolin-2-yl)butyl)phenol mono-fumarate salt, acetonitrile solvate according to any aspect described herein In some aspects, the techniques described herein relate to a pharmaceutical composition comprising crystal form D of 2-(t-butoxy)-4-(3-methyl-3-(5-(methylsulfonyl)isoindolin-2-yl)butyl)phenol mono-fumarate salt according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form D of 2-(t-butoxy)-4-(3-methyl-3-(5-(methylsulfonyl)isoindolin-2-yl)butyl)phenol mono-fumarate salt according to any aspect described herein In some aspects, the techniques described herein relate to a pharmaceutical composition comprising the crystal form F of 2-(t-butoxy)-4-(3-methyl-3-(5-(methylsulfonyl)isoindolin-2-yl)butyl)phenol mono-fumarate salt, hemi-hydrate according to any aspect described herein, and a pharmaceutically acceptable excipient.

In some aspects, the techniques described herein relate to methods of treating a disease selected from the group consisting of Alzheimer's Disease, Dementia with Lewy Bodies and Dry age-related macular degeneration in a subject in need thereof, comprising administering to the subject, crystal form F of 2-(t-butoxy)-4-(3-methyl-3-(5-(methylsulfonyl)isoindolin-2-yl)butyl)phenol mono-fumarate salt, hemi-hydrate according to any aspect described herein

DETAILED DESCRIPTION

Figure 1:
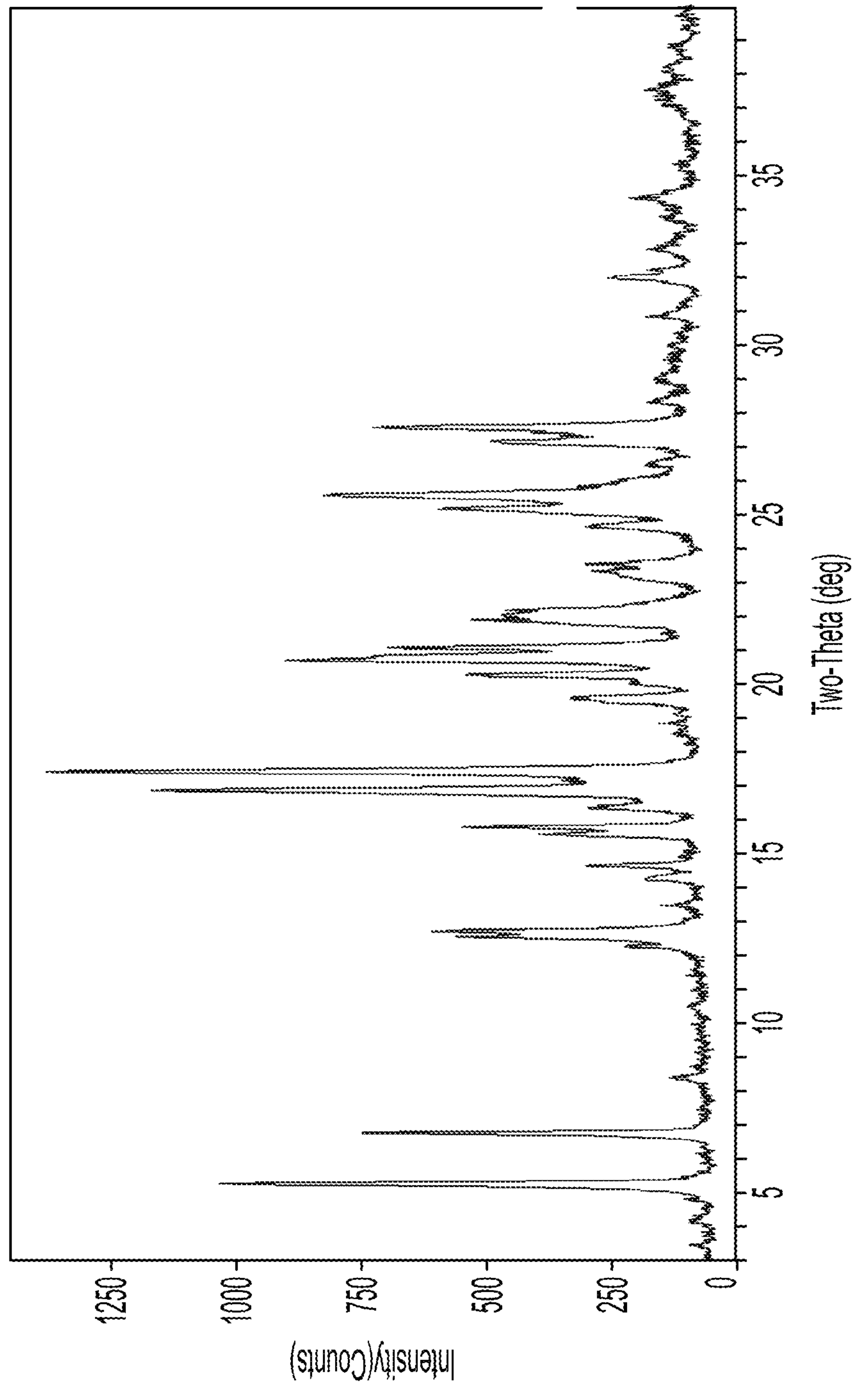
FIG. 1 is an X-ray powder diffraction pattern of 2-(t-butoxy)-4-(3-methyl-3-(5-(methylsulfonyl)isoindolin-2-yl)butyl)phenol mono-fumarate salt, crystal form A.

Compounds can exist in a variety of solid forms. These forms have different chemical and physical properties such as solubility, melting point, hygroscopicity, density, optical and mechanical properties, particle shape, flowability and dissolution rates and these properties can impact, for example, the compounds bioavailability, stability and ease of manufacture.

While a particular compound may be a solid, one cannot predict with any degree of certainty whether a compound will exist as a crystalline solid, single polymorph, have multiple polymorphs, or be amorphous. Furthermore, one cannot predict how to make possible polymorphs or what their physical properties will be.

CT1812 is a compound of Formula I (I)

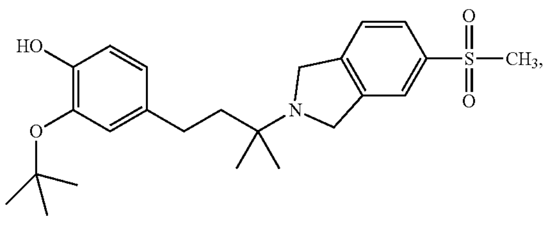

also known as 2-(tert-butoxy)-4-(3-methyl-3-(5-(methylsulfonyl)isoindolin-2-yl)butyl)phenol. It is a first-in-class, orally bioavailable investigational drug currently in Ph II clinical trials for Alzheimer's Disease, Lewy Body dementia (DLB) and for the treatment of geographic atrophy (GA) secondary to dry age-related macular degeneration (dry AMD). CT1812 is disclosed in International Publication WO2015/116923, and U.S. Pat. No. 9,796,672.

The present disclosure provides polymorphs of CT1812 fumarate salts, which includes solvates, hydrates, and anhydrous forms. The present disclosure also provides processes for making the crystalline forms and methods for using them to treat a variety of diseases and disorders.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present disclosure, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The articles "a" and "an" as used herein mean "one or more" or "at least one," unless otherwise indicated. That is, reference to any element of the present disclosure by the indefinite article "a" or "an" does not exclude the possibility that more than one of the elements is present.

The term "about" when used before a numerical designation, e.g., temperature, time, amount, and concentration, including a range, indicates approximations which may vary by ±10%, ±5% or ±1%.

The terms "administration," refers to introducing an agent into a patient. A therapeutic amount can be administered, which can be determined by the treating physician or the like. An oral route of administration is preferred for compounds of the present disclosure. The related terms and phrases "administering" and "administration of", when used in connection with a compound or pharmaceutical formulation (and grammatical equivalents) refer both to administration, which may be administration to a patient by a medical professional or by self-administration by the patient. In any event, administration entails delivery of the drug to the patient.

The term "API" is the abbreviation for "active pharmaceutical ingredient." As used herein, API refers to any 2-(t-butoxy)-4-(3-methyl-3-(5-(methylsulfonyl)isoindolin-2-yl)butyl)phenol fumarate salt described herein.

"Binder" refers to any pharmaceutically acceptable substance which can be used to bind the active and inert components together to maintain cohesive and discrete portions. Non-limiting examples of binders include hydroxypropylcellulose, hydroxypropylmethylcellulose, povidone, and ethyl cellulose.

"Chemical purity" refers to the purity of a compound in relation to all other materials (impurities) detectable by chemical analysis. In some instances, the chemical purity is measured by HPLC. In some instances, the chemical purity is measured by GC. "Area percent chemical purity", or "A %", is the percent ratio of the peak area of the compound being measured, to the sum of all peak areas in a high-performance liquid chromatography (HPLC) or gas chromatography (GC) chromatogram.

$$\text{Purity (peak area \%)} = \frac{\text{Peak Area}_{compound}}{\text{Sum of all Peak Areas}} \times 100\%$$

The A % purity is determined by the amount of the compound compared to related substances that are detectable by the method and does not consider the amount of other impurities that are not detectable by the method.

Throughout the application, descriptions of various aspects use "comprising" language, however in some specific instances, an aspect can alternatively be described using the language "consisting essentially of" or "consisting of".

"Diluent or filler" refers to substances that are used to dilute the active pharmaceutical ingredient prior to delivery. Diluents can also serve as stabilizers. Non-limiting examples of diluents include starch, saccharides, disaccharides, sucrose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, compressible sugars, dibasic calcium phosphate dehydrate, mannitol, and tribasic calcium phosphate.

"Effective amount", "pharmaceutically effective amount" or "therapeutically effective amount" is used herein to refer to an amount of the active ingredient sufficient to have a therapeutic effect upon administration, e.g. that amount which will cause an improvement or change in the condition for which it is administered. Effective amounts will vary with the particular condition being treated, the severity of the condition, the duration of the treatment, the stage of advancement of the condition, the body surface area affected with the clinical condition (for topical administration), and the specific components of the composition. The amount is sufficient to treat a disorder, disease or condition or one or more of its symptoms and/or to prevent the occurrence of the disease or disorder and can be determined by standard clinical techniques. Appropriate amounts in any given instance will be readily apparent to those skilled in the art or capable of determination by routine experimentation.

"Disintegrant or disintegrating agents" refers to a substance which, upon addition to a solid preparation, facilitates its break-up or disintegration after administration and permits the release of an active ingredient as efficiently as possible to allow for its rapid dissolution. Non-limiting examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

The terms "disorders," "diseases," and "conditions" are used inclusively herein and refer to any condition deviating from normal.

The term "excipient" or "pharmaceutically acceptable excipient" refers to pharmacologically inactive substances that are added to a pharmaceutical preparation in addition to the active pharmaceutical ingredient. Excipients may take the function of vehicle, diluent, release, disintegration or dissolution modifying agent, absorption enhancer, stabilizer or a manufacturing aid among others. Excipients may include fillers (diluents), binders, disintegrating agents, lubricants, and glidants.

"Glidant" as used herein is intended to mean agents used in tablet and capsule formulations to improve flow-properties during tablet compression and to produce an anti-caking effect. Non-limiting examples of glidants include colloidal silicon dioxide, talc, fumed silica, starch, starch derivatives, and bentonite.

The term "hemi-fumarate" or "hemi-fumarate salt" is used to indicate that one half of an equivalent of fumaric acid is present for each CT1812 free base molecule. For CT1812, the hemifumarate salt can be represented by the following chemical structure:

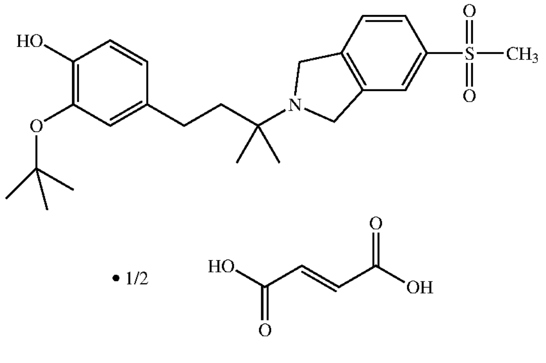

"Lubricant" refers to an excipient which is added to a powder blend to prevent the compacted powder mass from sticking to the equipment during the tableting or encapsulation process. It aids the ejection of the tablet form and can improve powder flow. Non-limiting examples of lubricants include magnesium stearate, stearic acid, silica, fats, calcium stearate, polyethylene glycol, sodium stearyl fumarate, talc, or fatty acids including lauric acid, oleic acid, and $C_8/C_{10}$ fatty acid.

The term "mono-fumarate" or "mono-fumarate salt" is used to indicate that one fumaric acid equivalent is present for each CT1812 free base molecule. For CT1812, the fumarate salt can be represented by the following chemical structure:

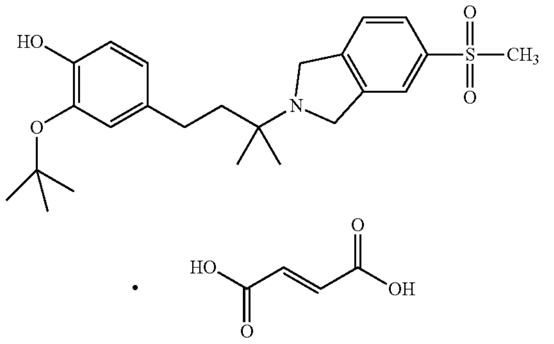

The term "pharmaceutically acceptable" indicates that the material does not have properties that would cause one of skill in the art to avoid administration of the material to a patient, taking into consideration the disease or conditions to be treated and the respective route of administration. Further, the material is considered to be safe for administration in humans or animals.

The term "polymorphism" is the ability of a chemical compound to crystallize in more than one crystal structure and it occurs when there is more than one way for molecules of the compound to pack in three-dimensional space. A "polymorph", or polymorphic form" as described herein relate to different crystalline forms and includes solvate and hydrate forms as defined herein. An "amorphous" form does not have a distinguishable crystal lattice and consists of a disordered arrangement of the molecules. "Solvates" are crystal forms containing either stoichiometric or non-stoichiometric amounts of a solvent. "Hydrates" are crystal forms containing either stoichiometric or non-stoichiometric amounts of a water.

The term "polymorph purity" refers to the purity of a particular polymorph (of 2-(t-butoxy)-4-(3-methyl-3-(5-(methylsulfonyl)isoindolin-2-yl)butyl)phenol fumarate salt (i.e., form A, or form B, or form C, or form D, or form E, or form F, or form G) relative to all other forms of the 2-(t-butoxy)-4-(3-methyl-3-(5-(methylsulfonyl)isoindolin-2-yl)butyl)phenol fumarate salt (i.e., other polymorphs including anhydrous, hydrates, solvates; and amorphous forms) present. For example, reference to "crystal form E that has a polymorph purity of at least 95%", means that at least 95% of the 2-(t-butoxy)-4-(3-methyl-3-(5-(methylsulfonyl)isoindolin-2-yl)butyl)phenol fumarate salt is crystal form E. Polymorph purity can be measure by any known method of measuring polymorph purity, for example, XRPD, DSC and Raman spectroscopy. In some aspects, the polymorph purity is measured by XRPD DSC or Raman spectroscopy or a combination thereof. In some aspects, the polymorph purity is measured by XRPD. In some aspects, the polymorph purity is measured by DSC. In some aspects, the polymorph purity is measured by Raman spectroscopy. In some aspects, the polymorph purity is measured by XRPD.

The terms "subject," "individual" or "patient" are used interchangeably and as used herein are intended to include human and non-human animals. Non-human animals include all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows, and horses. The methods are particularly suitable for treating human patients having a disease or disorder described herein.

The term "substantially as shown in FIG" in reference to a figure describing an XRPD, DSC, TGA or FTIR spectrum, relates to an XRPD, DSC, TGA or FTIR spectrum that would be considered by one skilled in the art to represent a compound possessing the same crystal form as the compound that provided the XRPD, DSC, TGA or FTIR spectrum of that figure. For example, as used herein an X-ray powder diffraction pattern that is "substantially as shown in FIG. 1" or the like, relates to an X-ray powder diffraction pattern that would be considered by one skilled in the art to represent a compound possessing the same crystal form as the compound that provided the XRPD pattern of FIG. 1. It is well known and understood to those skilled in the art that the apparatus employed, humidity, temperature, orientation of the powder crystals, and other parameters involved in obtaining an X-ray powder diffraction pattern may cause some variability in the appearance, intensities, and positions of the lines in the diffraction pattern. Thus, an X-ray powder diffraction pattern that is "substantially as shown in FIG. 1" or the like, may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining (e.g. by overlaying) if a sample of a crystalline compound has the same form as, or a different form from, a form disclosed herein by comparison of their XRPD patterns.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition.

It will be understood by one of skill in the art that any reference to form A refers to 2-(t-butoxy)-4-(3-methyl-3-(5-(methylsulfonyl)isoindolin-2-yl)butyl)phenol mono-fumarate salt, crystal form A. For example the terms "2-(t-butoxy)-4-(3-methyl-3-(5-(methylsulfonyl)isoindolin-2-yl)butyl)phenol mono-fumarate salt, crystal form A", "2-(t-butoxy)-4-(3-methyl-3-(5-(methylsulfonyl)isoindolin-2-yl)butyl)phenol mono-fumarate salt, form A", "2-(t-butoxy)-4-(3-methyl-3-(5-(methylsulfonyl)isoindolin-2-yl)butyl)phenol fumarate salt, crystal form A", "2-(t-butoxy)-4-(3-methyl-3-(5-(methylsulfonyl)isoindolin-2-yl)butyl)phenol fumarate salt, form A", "form A", "crystal form A", "CT1812 mono-fumarate crystal form A", "CT1812 mono-fumarate form A", "CT1812 fumarate salt form A", and "CT1812-fumarate salt crystal form A", are synonymous.

It will be understood by one of skill in the art that any reference to form B refers to 2-(t-butoxy)-4-(3-methyl-3-(5-(methylsulfonyl)isoindolin-2-yl)butyl)phenol mono-fumarate salt, acetone solvate, crystal form B. For example the terms "2-(t-butoxy)-4-(3-methyl-3-(5-(methylsulfonyl)isoindolin-2-yl)butyl)phenol mono-fumarate salt, acetone solvate, crystal form B", "2-(t-butoxy)-4-(3-methyl-3-(5-(methylsulfonyl)isoindolin-2-yl)butyl)phenol mono-fumarate salt, acetone solvate, form B", "2-(t-butoxy)-4-(3-methyl-3-(5-(methylsulfonyl)isoindolin-2-yl)butyl)phenol fumarate salt, acetone solvate, crystal form B", "2-(t-butoxy)-4-(3-methyl-3-(5-(methylsulfonyl)isoindolin-2-yl)butyl)phenol fumarate salt, acetone solvate, form B", "2-(t-butoxy)-4-(3-methyl-3-(5-(methylsulfonyl)isoindolin-2-yl)butyl)phenol fumarate salt, crystal form B", "2-(t-butoxy)-4-(3-methyl-3-(5-(methylsulfonyl)isoindolin-2-yl)butyl)phenol fumarate salt, form B", "form B", "crystal form B", "CT1812 mono-fumarate salt, acetone solvate, crystal form B", "CT1812 mono-fumarate salt, acetone solvate, form B", "CT1812 mono-fumarate salt, crystal form B", "CT1812 mono-fumarate salt, form B", "CT1812 fumarate salt, acetone solvate, crystal form B", "CT1812 fumarate salt, acetone solvate, form B", "CT1812 fumarate salt, form B", and "CT1812 fumarate salt, crystal form B", are synonymous.

It will be understood by one of skill in the art that any reference to form C refers to 2-(t-butoxy)-4-(3-methyl-3-(5-(methylsulfonyl)isoindolin-2-yl)butyl)phenol mono-fumarate salt, acetonitrile solvate, crystal form C. For example the terms "2-(t-butoxy)-4-(3-methyl-3-(5-(methylsulfonyl)isoindolin-2-yl)butyl)phenol mono-fumarate salt, acetonitrile solvate, crystal form C", "2-(t-butoxy)-4-(3-methyl-3-(5-(methylsulfonyl)isoindolin-2-yl)butyl)phenol mono-fumarate salt, acetonitrile solvate, form C", "2-(t-butoxy)-4-(3-methyl-3-(5-(methylsulfonyl)isoindolin-2-yl)butyl)phenol fumarate salt, acetonitrile solvate, crystal form C", "2-(t-butoxy)-4-(3-methyl-3-(5-(methylsulfonyl)isoindolin-2-yl)butyl)phenol fumarate salt, acetonitrile solvate, form C", "2-(t-butoxy)-4-(3-methyl-3-(5-(methylsulfonyl)isoindolin-2-yl)butyl)phenol fumarate salt, crystal form C", "2-(t-butoxy)-4-(3-methyl-3-(5-(methylsulfonyl)isoindolin-2-yl)butyl)phenol fumarate salt, form C" "form C", "crystal form C", "CT1812 mono-fumarate salt, acetonitrile solvate, crystal form C", "CT1812 mono-fumarate salt, acetonitrile solvate, form C", "CT1812 mono-fumarate salt, crystal form C", "CT1812 mono-fumarate salt, form C", "CT1812 fumarate salt, acetonitrile solvate, crystal form C", "CT1812 fumarate salt, acetonitrile solvate, form C", "CT1812 fumarate salt, form C", and "CT1812 fumarate salt, crystal form C", are synonymous.

It will be understood by one of skill in the art that any reference to form D refers to 2-(t-butoxy)-4-(3-methyl-3-(5-(methylsulfonyl)isoindolin-2-yl)butyl)phenol mono-fumarate salt, crystal form D. For example the terms "2-(t-butoxy)-4-(3-methyl-3-(5-(methylsulfonyl)isoindolin-2-yl)butyl)phenol mono-fumarate salt, crystal form D", "2-(t-butoxy)-4-(3-methyl-3-(5-(methylsulfonyl)isoindolin-2-yl)butyl)phenol mono-fumarate salt, form D", "2-(t-butoxy)-4-(3-methyl-3-(5-(methylsulfonyl)isoindolin-2-yl)butyl)phenol fumarate salt, crystal form D", "2-(t-butoxy)-4-(3-methyl-3-(5-(methylsulfonyl)isoindolin-2-yl)butyl)phenol fumarate salt, form D", "form D", "crystal form D", "CT1812 mono-fumarate crystal form D", "CT1812 mono-fumarate form D", "CT1812 fumarate salt form D and "CT 1812 fumarate salt crystal form D", are synonymous.

It will be understood by one of skill in the art that any reference to form E refers to 2-(t-butoxy)-4-(3-methyl-3-(5-(methylsulfonyl)isoindolin-2-yl)butyl)phenol hemi-fumarate dihydrate salt, crystal form E. For example the terms "2-(t-butoxy)-4-(3-methyl-3-(5-(methylsulfonyl)isoindolin-2-yl)butyl)phenol hemi-fumarate dihydrate salt, crystal form E", "2-(t-butoxy)-4-(3-methyl-3-(5-(methylsulfonyl)isoindolin-2-yl)butyl)phenol hemi-fumarate dihydrate salt, form E", "2-(t-butoxy)-4-(3-methyl-3-(5-(methylsulfonyl)isoindolin-2-yl)butyl)phenol fumarate salt, hydrate crystal form E", "2-(t-butoxy)-4-(3-methyl-3-(5-(methylsulfonyl)isoindolin-2-yl)butyl)phenol fumarate salt, hydrate form E", "2-(t-butoxy)-4-(3-methyl-3-(5-(methylsulfonyl)isoindolin-2-yl)butyl)phenol fumarate salt, crystal form E", "2-(t-butoxy)-4-(3-methyl-3-(5-(methylsulfonyl)isoindolin-2-yl)butyl)phenol fumarate salt, form E", "form E", "crystal form E", "CT1812 hemi-fumarate dihydrate crystal form E", "CT1812 hemi-fumarate dihydrate form E", "CT1812 fumarate salt, hydrate crystal form E, and "CT1812 fumarate salt, hydrate form E", "CT1812 fumarate salt crystal form E, and "CT1812 fumarate salt form E", are synonymous.

It will be understood by one of skill in the art that any reference to form F refers 2-(t-butoxy)-4-(3-methyl-3-(5-(methylsulfonyl)isoindolin-2-yl)butyl)phenol mono-fumarate salt, hemi-hydrate, crystal form F. For example the terms "2-(t-butoxy)-4-(3-methyl-3-(5-(methylsulfonyl)isoindolin-2-yl)butyl)phenol mono-fumarate salt, hemi-hydrate, crystal form F", "2-(t-butoxy)-4-(3-methyl-3-(5-(methylsulfonyl)isoindolin-2-yl)butyl)phenol mono-fumarate salt, hemi-hydrate, form F", "2-(t-butoxy)-4-(3-methyl-3-(5-(methylsulfonyl)isoindolin-2-yl)butyl)phenol fumarate salt, hydrate, crystal form F", "2-(t-butoxy)-4-(3-methyl-3-(5-(methylsulfonyl)isoindolin-2-yl)butyl)phenol fumarate salt, hydrate, form F", "2-(t-butoxy)-4-(3-methyl-3-(5-(methylsulfonyl)isoindolin-2-yl)butyl)phenol fumarate salt, crystal form F", "2-(t-butoxy)-4-(3-methyl-3-(5-(methylsulfonyl)isoindolin-2-yl)butyl)phenol fumarate salt, crystal form F", "form F", "crystal form F", "CT1812 mono-fumarate salt crystal form F", "CT1812 mono-fumarate salt form F", "CT1812 fumarate salt form F", "CT1812 fumarate salt crystal form F", CT1812 fumarate salt, hemi-hydrate form F", "CT1812 fumarate salt, hemi-hydrate, crystal form F", "CT1812 mono-fumarate hemi-hydrate, crystal form F", "CT1812 mono-fumarate hemi-hydrate, form F", "CT1812 fumarate salt, hydrate, form F", and "CT1812 fumarate salt hydrate, crystal form F" are synonymous.

It will be understood by one of skill in the art that any reference to form G refers to 2-(t-butoxy)-4-(3-methyl-3-(5-(methylsulfonyl)isoindolin-2-yl)butyl)phenol mono-fumarate salt, methanol solvate, crystal form G. For example the terms "2-(t-butoxy)-4-(3-methyl-3-(5-(methylsulfonyl)isoindolin-2-yl)butyl)phenol mono-fumarate salt, methanol solvate, crystal form G", "2-(t-butoxy)-4-(3-methyl-3-(5-(methylsulfonyl)isoindolin-2-yl)butyl)phenol mono-fumarate salt, methanol solvate, form G", "2-(t-butoxy)-4-(3-methyl-3-(5-(methylsulfonyl)isoindolin-2-yl)butyl)phenol fumarate salt, methanol solvate, crystal form G", "2-(t-butoxy)-4-(3-methyl-3-(5-(methylsulfonyl)isoindolin-2-yl)butyl)phenol fumarate salt, methanol solvate, form G", "2-(t-butoxy)-4-(3-methyl-3-(5-(methylsulfonyl)isoindolin-2-yl)butyl)phenol fumarate salt, crystal form G", "2-(t-butoxy)-4-(3-methyl-3-(5-(methylsulfonyl)isoindolin-2-yl)butyl)phenol fumarate salt, form G" "form G", "crystal form G", "CT1812 mono-fumarate salt, methanol solvate, crystal form G", "CT 1812 mono-fumarate salt, methanol solvate, form G", "CT1812 mono-fumarate salt, crystal form G", "CT1812 mono-fumarate salt, form G", "CT1812 fumarate salt, methanol solvate, crystal form G", "CT1812 fumarate salt, methanol solvate, form G", "CT1812 fumarate salt, form G", and "CT1812 fumarate salt, crystal form G", are synonymous.

Crystal Forms

Generally, the present disclosure provides crystalline forms of 2-(t-butoxy)-4-(3-methyl-3-(5-(methylsulfonyl) isoindolin-2-yl)butyl)phenol fumarate salts. In some aspects, the salt is a mono fumarate salt. In some aspects, the salt is a hemi-fumarate salt.

In some aspects, the crystalline form is 2-(t-butoxy)-4-(3-methyl-3-(5-(methylsulfonyl)isoindolin-2-yl)butyl)phenol mono-fumarate salt, crystal form A characterized by an X-ray powder diffraction (XRPD) pattern comprising at least three characteristic 2θ peaks at 5.23, 16.84, 17.41, 20.72 and 25.550 (t 0.2°). In some aspects, the crystalline form is 2-(t-butoxy)-4-(3-methyl-3-(5-(methylsulfonyl) isoindolin-2-yl)butyl)phenol mono-fumarate salt, crystal form A characterized by an X-ray powder diffraction (XRPD) pattern comprising characteristic 2θ peaks at 5.23, 16.84, 17.41, 20.72 and 25.55° (+0.2°). In some aspects, the XRPD of crystal form A further comprises additional peaks at 6.73, 12.65, 21.06, 25.15 and 27.55° (±0.2°). In some aspects, the XRPD of crystal form A further comprises additional peaks at 12.51, 15.75, 20.25, 21.90, 22.15 and 27.12° (±0.2°). In some aspects, the XRPD of crystal form A further comprises peaks at 15.55 and 19.55° (±0.2°). In some aspects, the XRPD of crystal form A further comprises peaks at 14.63, 23.28, 23.51, 24.65, and 31.98° (±0.2°). In some aspects, the XRPD of crystal form A is substantially as shown in FIG. 1. In some aspects, the XRPD of crystal form A comprises peaks as described in Table 1.

TABLE 1

XRPD 2-Theta values of 2-(t-butoxy)-4-(3-methyl-3-(5-(methylsulfonyl)isoindolin-2-yl)butyl)phenol mono-fumarate salt, crystal form A

| Pos. °2θ | Rel. Int. % |
|---|---|
| 4.1537 | 2.46 |
| 5.2313 | 69.13 |
| 6.7295 | 44.05 |
| 8.3616 | 4.77 |
| 12.5103 | 35.07 |
| 12.6535 | 40.25 |
| 13.4633 | 4.05 |
| 14.2591 | 8.87 |
| 14.6259 | 15.59 |
| 15.5549 | 23.68 |
| 15.7536 | 30.95 |
| 16.3567 | 16.99 |
| 16.8415 | 83.72 |
| 17.4058 | 100 |
| 19.5459 | 20.95 |
| 20.2515 | 35.46 |
| 20.7208 | 65.47 |
| 21.0555 | 44.51 |
| 21.9045 | 35.07 |
| 22.1521 | 30.45 |
| 23.2773 | 15.56 |
| 23.5109 | 14.68 |
| 24.6459 | 17.36 |
| 25.1459 | 41.22 |
| 25.5517 | 61.43 |
| 26.4881 | 7.55 |
| 27.1242 | 32.99 |
| 27.549 | 50.27 |
| 28.3323 | 6.85 |
| 28.9916 | 6.02 |
| 30.8434 | 5.8 |
| 31.9796 | 12.97 |
| 32.8256 | 5.66 |
| 34.3171 | 8.32 |
| 37.3949 | 4.59 |
| 38.1141 | 3.41 |

Figure 2:
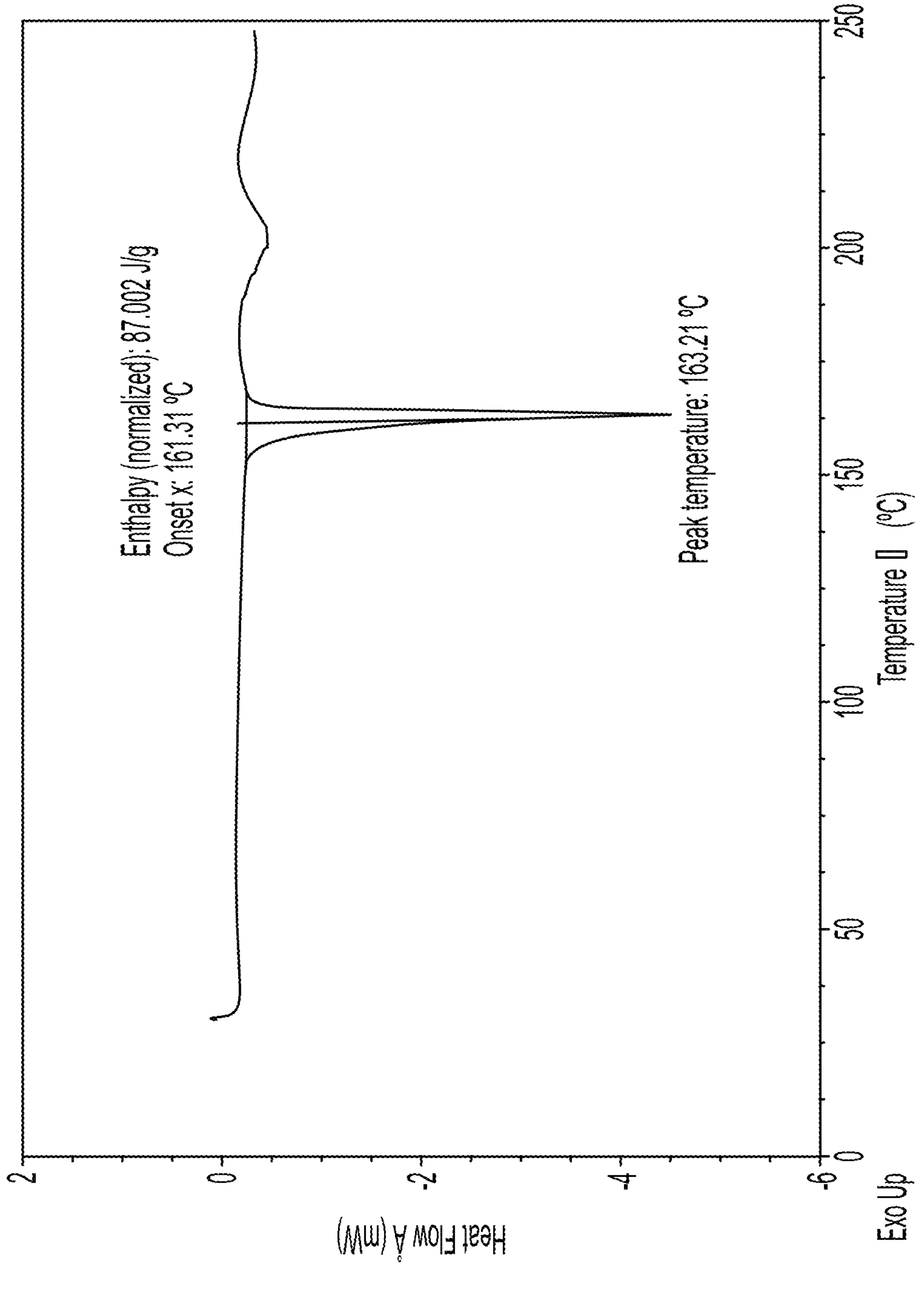
FIG. 2 is a differential scanning calorimetry (DSC) curve of 2-(t-butoxy)-4-(3-methyl-3-(5-(methylsulfonyl)isoindolin-2-yl)butyl)phenol mono-fumarate salt, crystal form A.

In some aspects, the 2-(t-butoxy)-4-(3-methyl-3-(5-(methylsulfonyl)isoindolin-2-yl)butyl)phenol mono-fumarate salt, crystal form A is characterized by a differential scanning calorimetry (DSC) curve that has a melting peak at T onset of about 161.3° C. and an enthalpy of about 87 J/g. In some aspects, the crystal form A is characterized by a differential scanning calorimetry curve that has a peak temperature of melting at about 163.2° C. In some aspects, the DSC of crystal form A is substantially as shown in FIG. 2.

Figure 3:
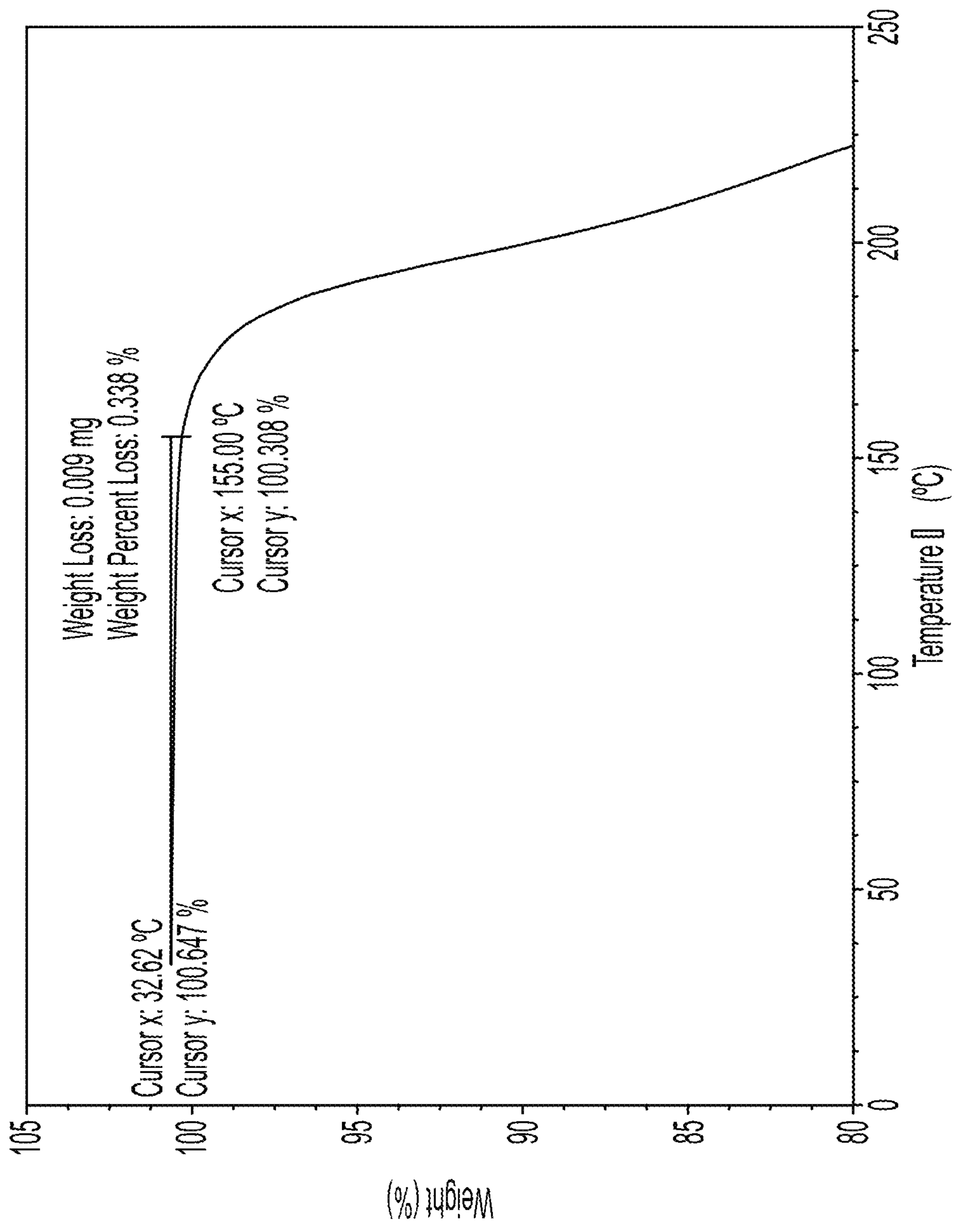
FIG. 3 is a thermogravimetric analysis (TGA) of 2-(t-butoxy)-4-(3-methyl-3-(5-(methylsulfonyl)isoindolin-2-yl)butyl)phenol mono-fumarate salt, crystal form A.

In some aspects, 2-(t-butoxy)-4-(3-methyl-3-(5-(methylsulfonyl)isoindolin-2-yl)butyl)phenol mono-fumarate salt, crystal form A shows about 0.3% weight loss at about 155° C. by thermogravimetric analysis (TGA). In some aspects, the TGA of crystal form A is substantially as shown in FIG. 3.

Figure 4:
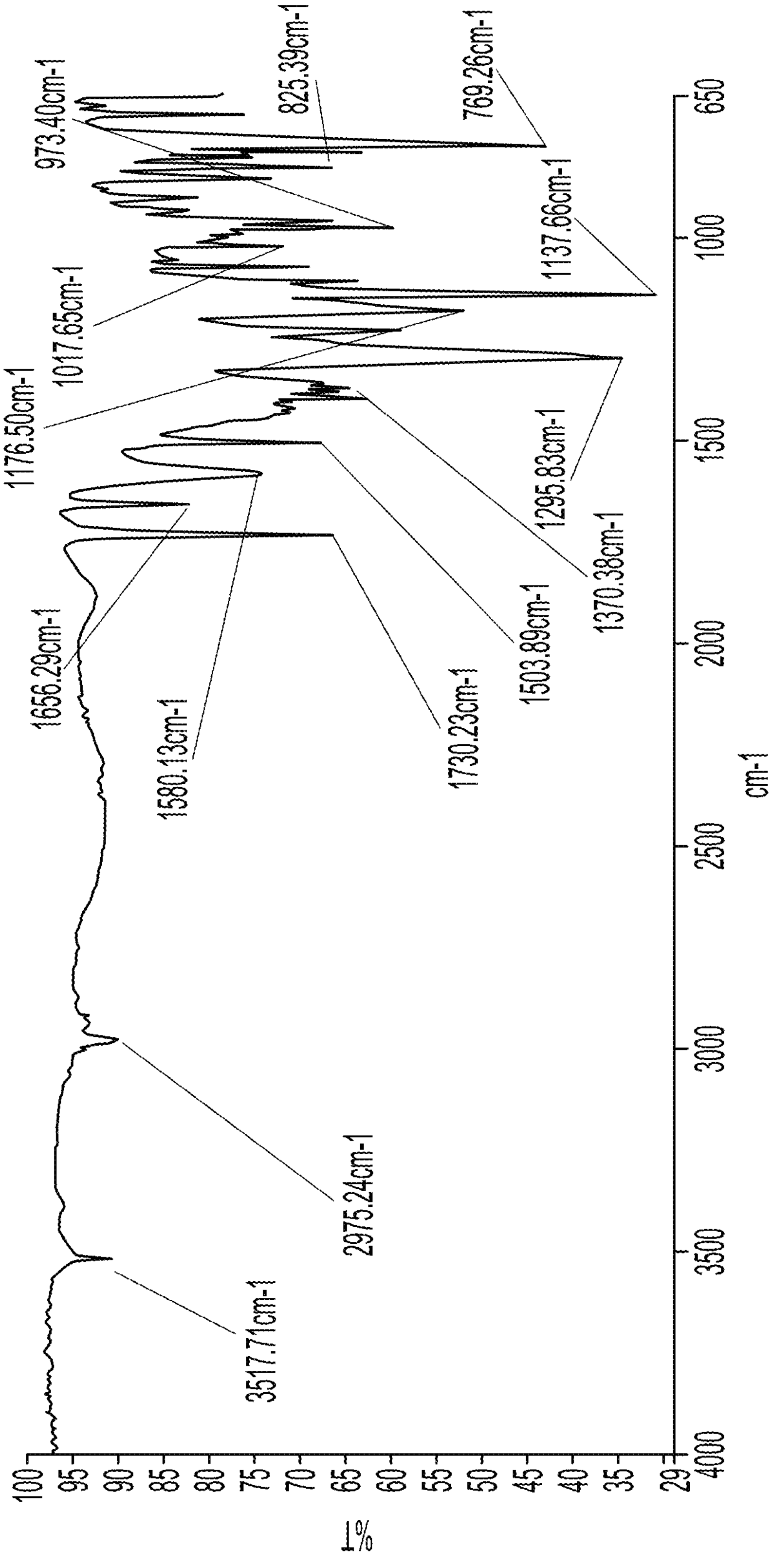
FIG. 4 is a Fourier-transform infrared (FTIR) spectrum of 2-(t-butoxy)-4-(3-methyl-3-(5-(methylsulfonyl)isoindolin-2-yl)butyl)phenol mono-fumarate salt, crystal form A.

In some aspects, 2-(t-butoxy)-4-(3-methyl-3-(5-(methylsulfonyl)isoindolin-2-yl)butyl)phenol mono-fumarate salt, crystal form A has a Fourier-transform infrared (FTIR) spectrum substantially as shown in FIG. 4.

In some aspects, 2-(t-butoxy)-4-(3-methyl-3-(5-(methylsulfonyl)isoindolin-2-yl)butyl)phenol mono-fumarate salt, crystal form A is described by an XRPD as described in any aspect of paragraphs [0098]-0 in combination with any aspect of DSC, as described in paragraph [0100], TGA as described in paragraph [0101] and/or FTIR as described in paragraph [0102].

In some aspects, 2-(t-butoxy)-4-(3-methyl-3-(5-(methylsulfonyl)isoindolin-2-yl)butyl)phenol mono-fumarate salt, crystal form A according to any aspect described herein, has a polymorph purity of at least 50%. In some aspects, crystal form A has a polymorph purity of at least 75%. In some aspects, crystal form A has a polymorph purity of at least 80%. In some aspects, crystal form A has a polymorph purity of at least 85%. In some aspects, crystal form A has a polymorph purity of at least 90%. In some aspects, crystal form A has a polymorph purity of at least 95%. In some aspects, crystal form A has a polymorph purity of at least 96%. In some aspects, crystal form A has a polymorph purity of at least 97%. In some aspects, crystal form A has a polymorph purity of at least 98%. In some aspects, crystal form A has a polymorph purity of at least 99%. In some aspects, crystal form A has a polymorph purity of about 95%. In some aspects, crystal form A has a polymorph purity of about 96%. In some aspects, crystal form A has a polymorph purity of about 97%. In some aspects, crystal form A has a polymorph purity of about 98%. In some aspects, crystal form A has a polymorph purity of about 99%.

In some aspects, 2-(t-butoxy)-4-(3-methyl-3-(5-(methylsulfonyl)isoindolin-2-yl)butyl)phenol mono-fumarate salt, crystal form A, according to any aspect described herein has a chemical purity of at least 50 A %. In some aspects, crystal form A has a chemical purity of at least 75 A %. In some aspects, crystal form A has a chemical purity of at least 80 A %. In some aspects, crystal form A has a chemical purity of at least 85 A %. In some aspects, crystal form A has a chemical purity of at least 90 A %. In some aspects, crystal form A has a chemical purity of at least 91 A %. In some aspects, crystal form A has a chemical purity of at least 92 A %. In some aspects, crystal form A has a chemical purity of at least 93 A %. In some aspects, crystal form A has a chemical purity of at least 94 A %. In some aspects, crystal form A has a chemical purity of at least 95 A %. In some aspects, crystal form A has a chemical purity of at least 96 A %. In some aspects, crystal form A has a chemical purity of at least 97 A %. In some aspects, crystal form A has a chemical purity of at least 98 A %. In some aspects, crystal form A has a chemical purity of at least 99 A %. In some aspects, crystal form A has a chemical purity of about 90 A %. In some aspects, crystal form A has a chemical purity of about 91 A %. In some aspects, crystal form A has a chemical purity of about 92 A %. In some aspects, crystal form A has a chemical purity of about 93 A %. In some aspects, crystal form A has a chemical purity of about 94 A %. In some aspects, crystal form A has a chemical purity of about 95 A %. In some aspects, crystal form A has a chemical purity of about 96 A %. In some aspects, crystal form A has a chemical purity of about 97 A %. In some aspects, crystal form A has a chemical purity of about 98 A %. In some aspects, crystal form A has a chemical purity of about 99 A %.

Figure 10:
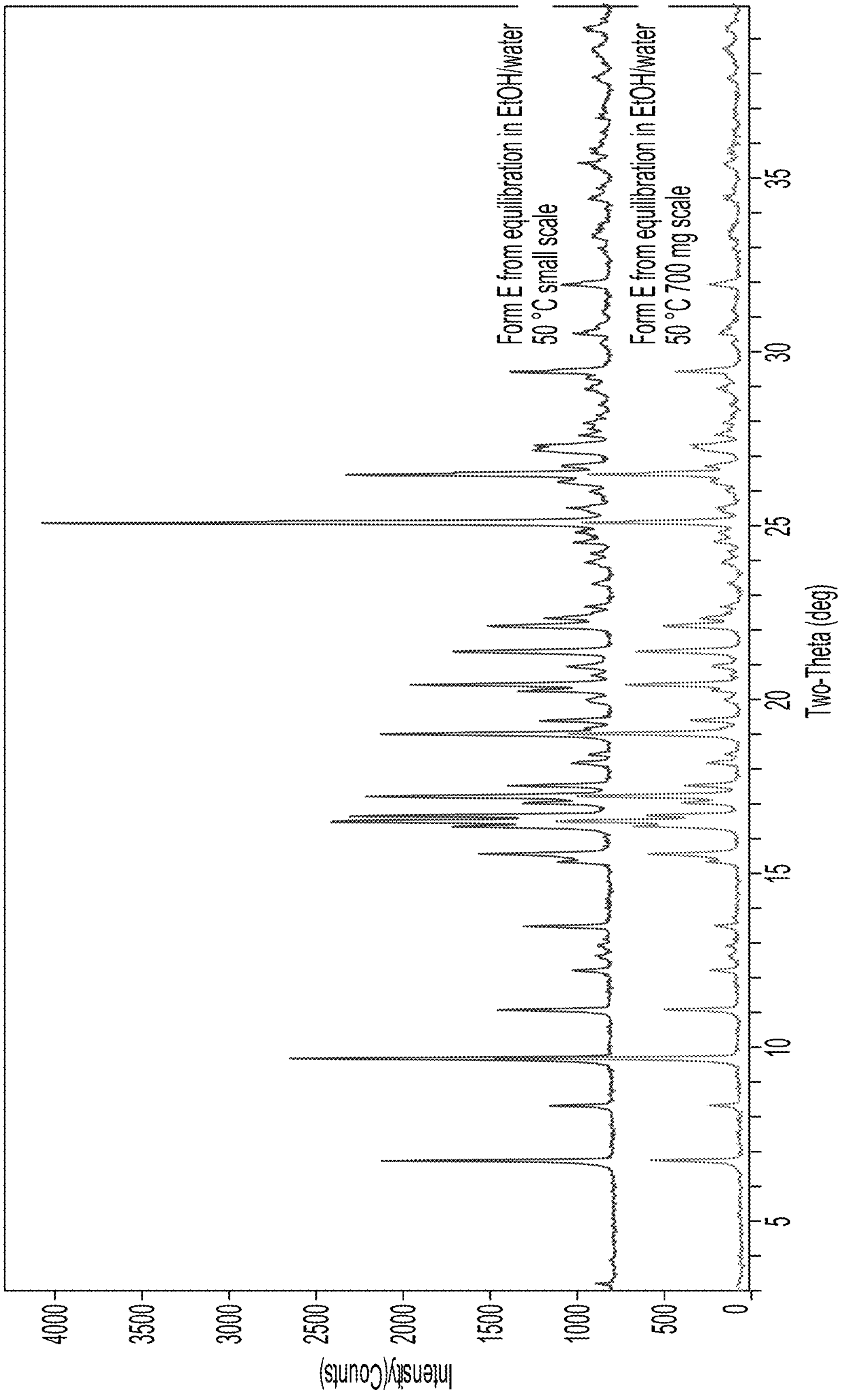
FIG. 10 is an X-ray powder diffraction pattern overlay of 2-(t-butoxy)-4-(3-methyl-3-(5-(methylsulfonyl)isoindolin-2-yl)butyl)phenol hemi-fumarate dihydrate salt, crystal form E obtained by equilibration of 2-(t-butoxy)-4-(3-methyl-3-(5-(methylsulfonyl)isoindolin-2-yl)butyl)phenol mono-fumarate salt, crystal form A at 50° C. in 1:1 EtOH:water (V/V). The top XRPD is on a 50 mg scale of crystal form A, and the bottom XRPD is on a 700 mg scale of form A.
Figure 40:
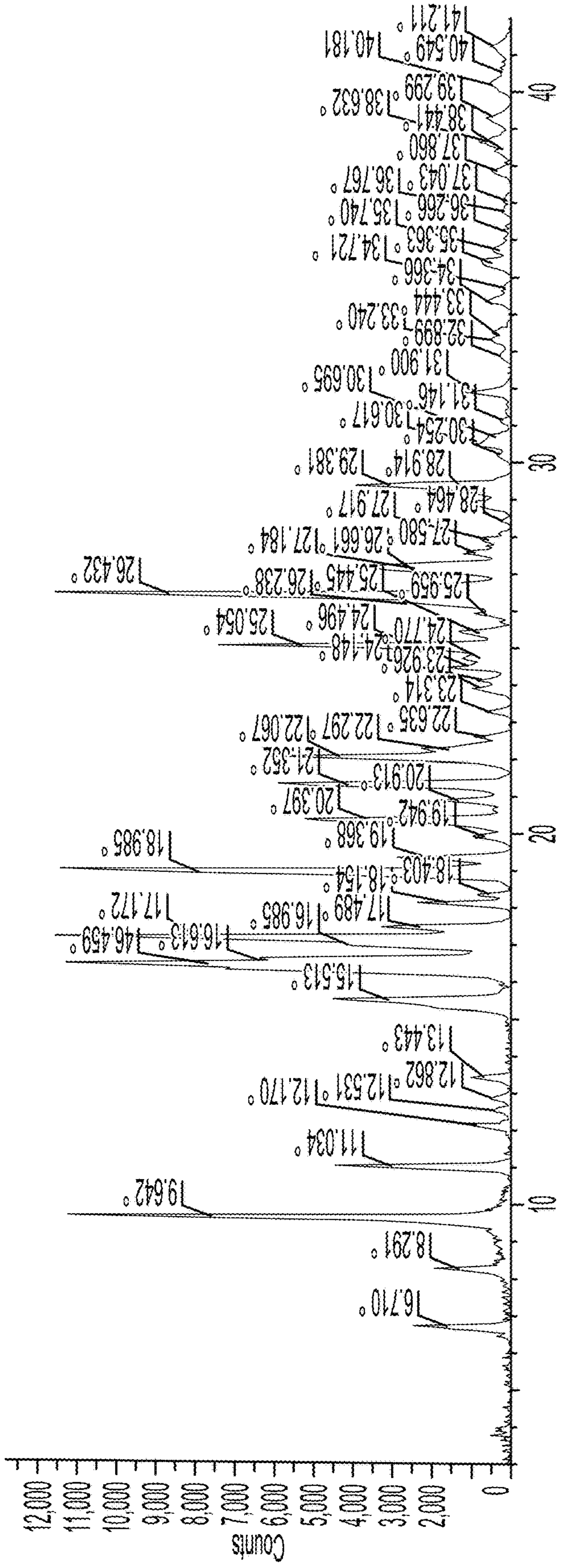
FIG. 40 is an X-ray powder diffraction pattern of 2-(t-butoxy)-4-(3-methyl-3-(5-(methylsulfonyl)isoindolin-2-yl)butyl)phenol hemi-fumarate dihydrate salt, crystal form E obtained by the method of Example 2, Method K.

In some aspects, the crystalline form is 2-(t-butoxy)-4-(3-methyl-3-(5-(methylsulfonyl)isoindolin-2-yl)butyl)phenol hemi-fumarate dihydrate salt, crystal form E characterized by an X-ray powder diffraction (XRPD) pattern comprising at least three characteristic 2θ peaks at 9.69, 16.51, 17.23, 19.02, 25.10, and 26.49° (±0.2°). In some aspects, the crystalline form is 2-(t-butoxy)-4-(3-methyl-3-(5-(methylsulfonyl)isoindolin-2-yl)butyl)phenol hemi-fumarate dihydrate salt, crystal form E characterized by an X-ray powder diffraction (XRPD) pattern comprising characteristic 2θ peaks at 9.69, 16.51, 17.23, 19.02, 25.10, and 26.49° (±0.2°). In some aspects, the XRPD of crystal form E comprises additional peaks at 6.75, 11.09, 15.56, 16.35, 16.67, 20.43, 21.39, and 22.12° (±0.2°). In some aspects, the XRPD of crystal form E further comprises additional peaks at 17.04, 17.54, 19.41, and 29.45° (±0.2°). In some aspects, the XRPD of crystal form E further comprises peaks at 15.34, 22.35, 26.71, 27.17, and 27.29° (±0.2°). In some aspects, the XRPD of crystal form E is substantially as shown in FIG. 10. In some aspects, the XRPD of crystal form E is substantially as shown in FIG. 40. In some aspects, the XRPD of crystal form E comprises peaks as described in Table 2.

TABLE 2

XRPD of 2-(t-butoxy)-4-(3-methyl-3-(5-(methylsulfonyl)isoindolin-2-yl)butyl)phenol hemi-fumarate dihydrate salt, crystal form E

| Pos. [°2θ] | Rel. Int. % |
|---|---|
| 6.75 | 33.09 |
| 8.33 | 11.27 |
| 9.69 | 100 |
| 11.09 | 29.14 |
| 12.22 | 11.77 |
| 12.62 | 4.18 |
| 12.93 | 5.41 |
| 13.49 | 10.4 |
| 15.34 | 13.6 |
| 15.56 | 36.07 |
| 16.35 | 39.36 |
| 16.51 | 73.01 |
| 16.67 | 37.38 |
| 17.04 | 22.91 |
| 17.23 | 65.55 |
| 17.54 | 20.67 |
| 18.19 | 12.75 |
| 18.44 | 5.98 |
| 19.02 | 65.97 |
| 19.41 | 19.63 |
| 20.00 | 6.28 |
| 20.26 | 11.18 |
| 20.43 | 44.1 |
| 20.71 | 4.09 |
| 20.97 | 9.94 |
| 21.39 | 40.23 |
| 22.12 | 30.77 |
| 22.35 | 14.46 |
| 22.68 | 7.05 |
| 23.35 | 4.32 |
| 23.95 | 6.89 |
| 24.23 | 4.4 |
| 24.55 | 9.93 |
| 24.82 | 8.49 |
| 25.10 | 62.23 |
| 25.51 | 9.49 |
| 26.02 | 5.36 |
| 26.28 | 11.69 |
| 26.49 | 59.54 |
| 26.71 | 14.03 |
| 27.17 | 14.66 |
| 27.29 | 17.04 |
| 27.64 | 8.05 |
| 27.98 | 6.74 |
| 28.49 | 3.55 |
| 28.95 | 8.96 |
| 29.45 | 24.42 |
| 30.25 | 3.1 |
| 30.54 | 7.07 |
| 31.24 | 2.57 |
| 31.95 | 12.16 |
| 33.39 | 4.33 |
| 34.40 | 6.16 |
| 35.41 | 6.82 |
| 35.82 | 3.83 |
| 36.33 | 2.4 |
| 36.75 | 2.71 |
| 37.89 | 4.36 |
| 38.72 | 6.42 |
| 39.30 | 5.11 |

In some aspects, the crystalline form is 2-(t-butoxy)-4-(3-methyl-3-(5-(methylsulfonyl)isoindolin-2-yl)butyl)phenol hemi-fumarate dihydrate salt, crystal form E, having a unit crystal that shows, in single-crystal analysis, the crystal data in Table 3.

TABLE 3

Single crystal analysis of 2-(t-butoxy)-4-(3-methyl-3-(5-(methylsulfonyl)isoindolin-2-yl)butyl)phenol hemi-fumarate dihydrate salt, crystal form E

| | |
|---|---|
| Crystal dimension (mm) | 0.15 × 0.12 × 0.08 |
| Temperature (K) | 170 |
| a (Å) | 32.5801(12) |
| b (Å) | 9.7212(4) |
| c (Å) | 21.2820(7) |
| α (°) | 90 |
| β (°) | 126.4700(10) |
| γ (°) | 90 |

TABLE 3-continued

| Single crystal analysis of 2-(t-butoxy)-4-(3-methyl-3-(5-(methylsulfonyl)isoindolin-2-yl)butyl)phenol hemi-fumarate dihydrate salt, crystal form E | |
|---|---|
| V (Å$^3$) | 5420.4(4) |
| Space Group | C2/c |
| Z | 8 |
| Chemical formula/ asymmetric unit | $C_{24}H_{34}NO_4S \bullet 0.5C_4H_2O_4 \bullet 2H_2O$ |
| Crystal density (g/cm$^3$) | 1.288 |

Figure 11:
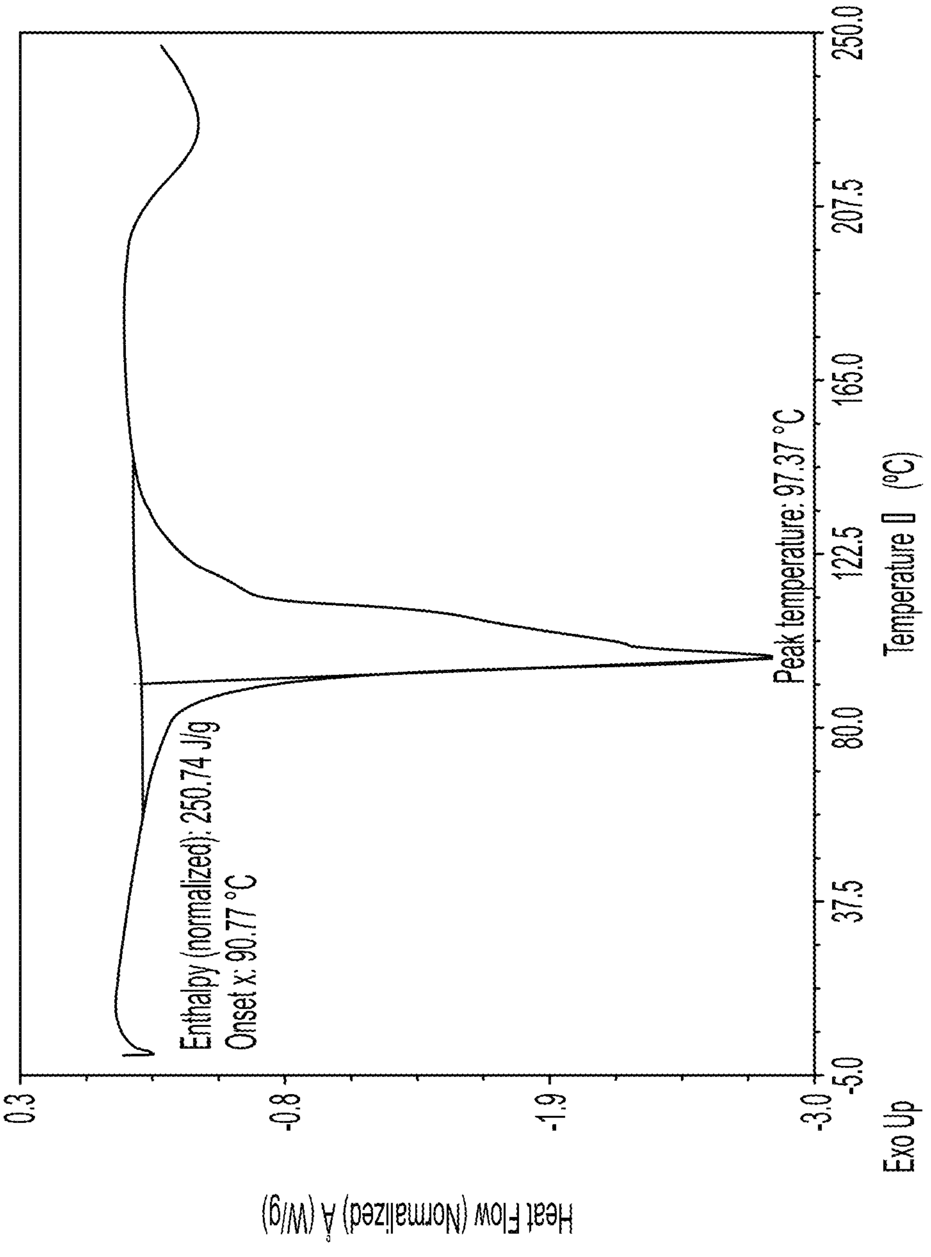
FIG. 11 is a differential scanning calorimetry (DSC) curve of 2-(t-butoxy)-4-(3-methyl-3-(5-(methylsulfonyl)isoindolin-2-yl)butyl)phenol hemi-fumarate dihydrate salt, crystal form E.
Figure 41:
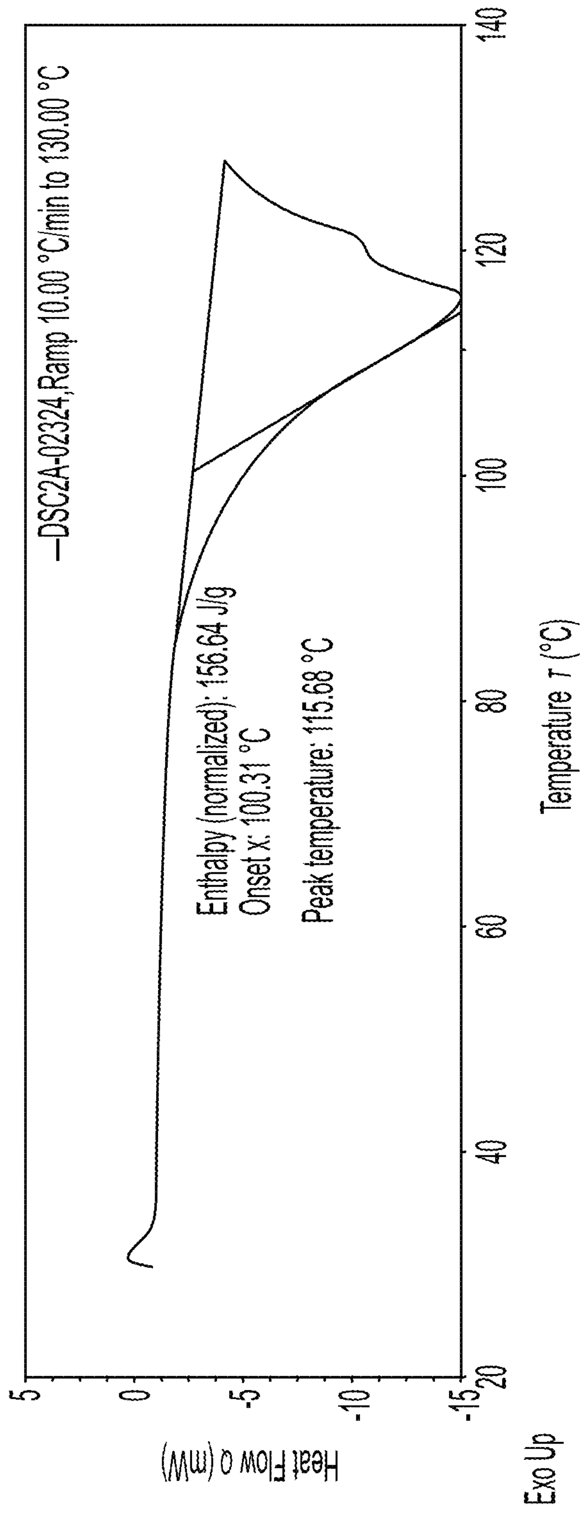
FIG. 41 is a differential scanning calorimetry (DSC) curve of 2-(t-butoxy)-4-(3-methyl-3-(5-(methylsulfonyl)isoindolin-2-yl)butyl)phenol hemi-fumarate dihydrate salt, crystal form E obtained by the method of Example 2, Method K.

In some aspects, 2-(t-butoxy)-4-(3-methyl-3-(5-(methylsulfonyl)isoindolin-2-yl)butyl)phenol hemi-fumarate dihydrate salt, crystal form E is characterized by a differential scanning calorimetry (DSC) curve has a broad dehydration peak at T onset of about 90.8° C. with an enthalpy of about 251 J/g. In some aspects, 2-(t-butoxy)-4-(3-methyl-3-(5-(methylsulfonyl)isoindolin-2-yl)butyl)phenol hemi-fumarate dihydrate salt, crystal form E is characterized by a differential scanning calorimetry (DSC) curve has a broad dehydration peak at T onset of about 90.8° C. with a peak at 115.7° C. In some aspects, the DSC of crystal form E is substantially as shown in FIG. 11. In some aspects, the DSC of crystal form E is substantially as shown in FIG. 41

Figure 12:
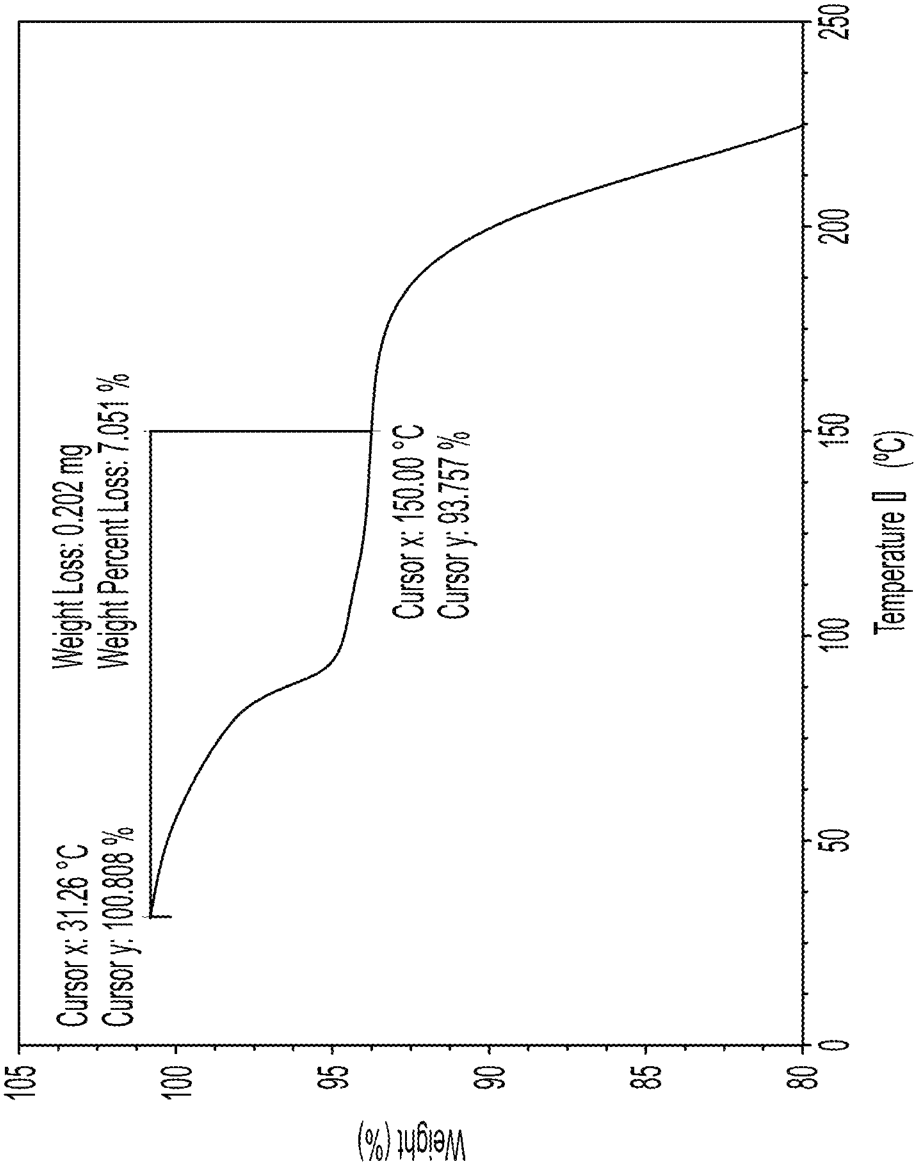
FIG. 12 is a thermogravimetric analysis (TGA) of 2-(t-butoxy)-4-(3-methyl-3-(5-(methylsulfonyl)isoindolin-2-yl)butyl)phenol hemi-fumarate dihydrate salt, crystal form E.
Figure 42:
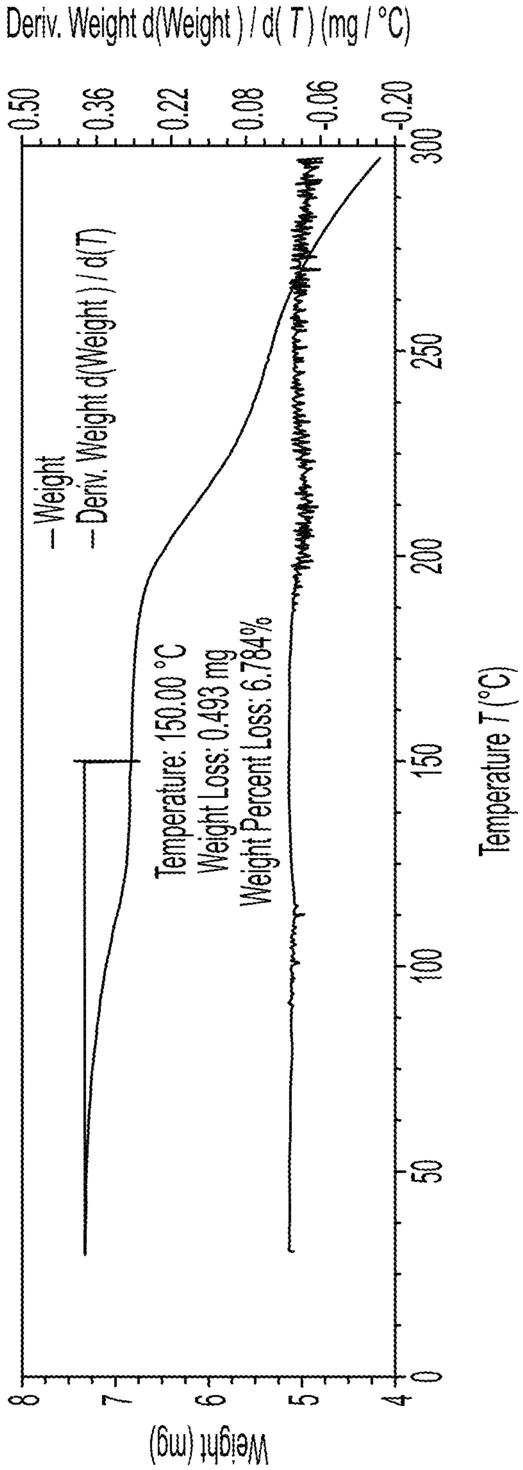
FIG. 42 is a thermogravimetric analysis (TGA) of 2-(t-butoxy)-4-(3-methyl-3-(5-(methylsulfonyl)isoindolin-2-yl)butyl)phenol hemi-fumarate dihydrate salt, crystal form E obtained by the method of Example 2, Method K.

In some aspects, 2-(t-butoxy)-4-(3-methyl-3-(5-(methylsulfonyl)isoindolin-2-yl)butyl)phenol hemi-fumarate dihydrate salt, crystal form E shows about 6.8 to about 7.0% weight loss at about 150° C. by thermogravimetric analysis (TGA). In some aspects, the TGA of crystal form E is substantially as shown in FIG. 12. In some aspects, the TGA of crystal form E is substantially as shown in FIG. 42.

Figure 13:
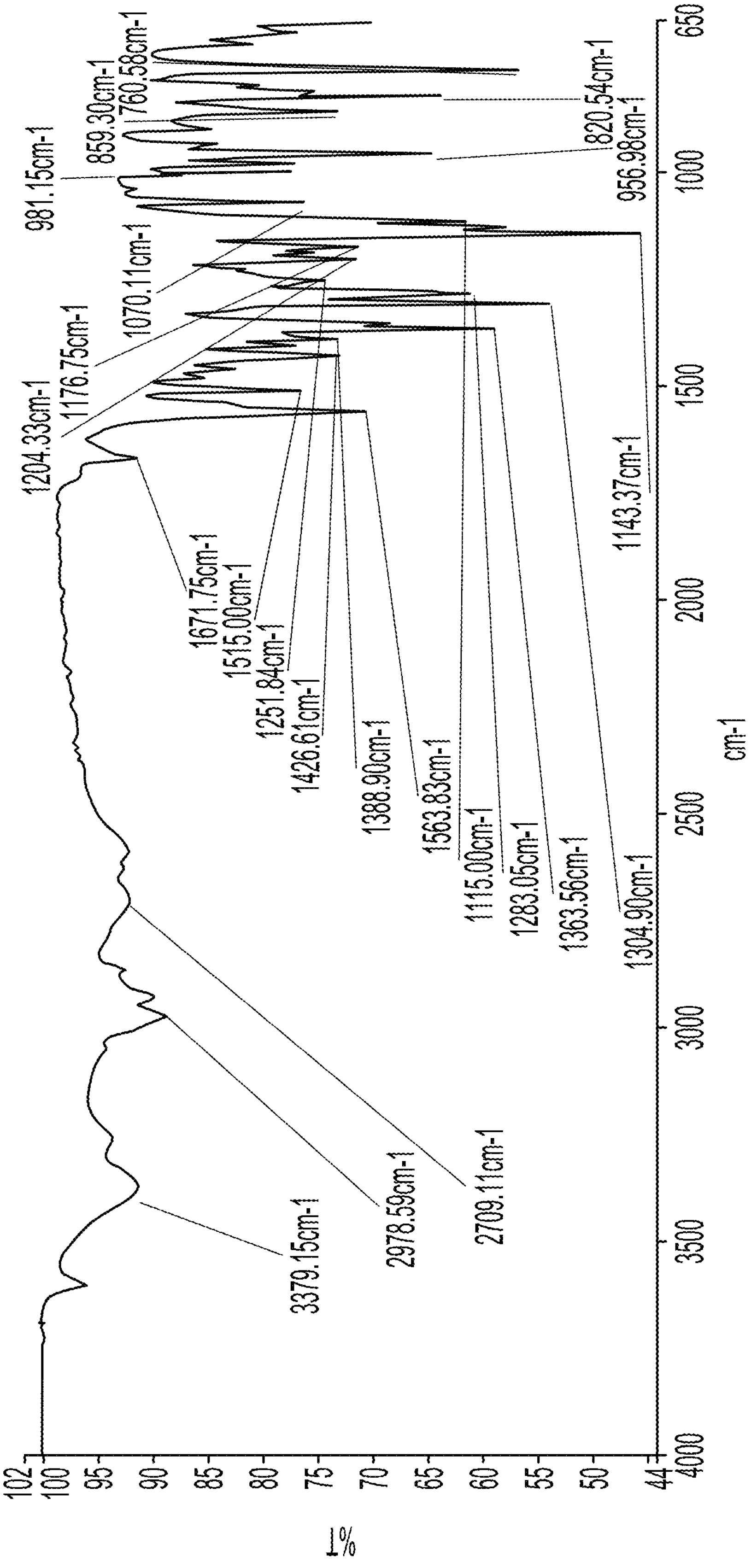
FIG. 13 is a Fourier-transform infrared (FTIR) spectrum of 2-(t-butoxy)-4-(3-methyl-3-(5-(methylsulfonyl)isoindolin-2-yl)butyl)phenol hemi-fumarate dihydrate, crystal form E.
Figure 14:
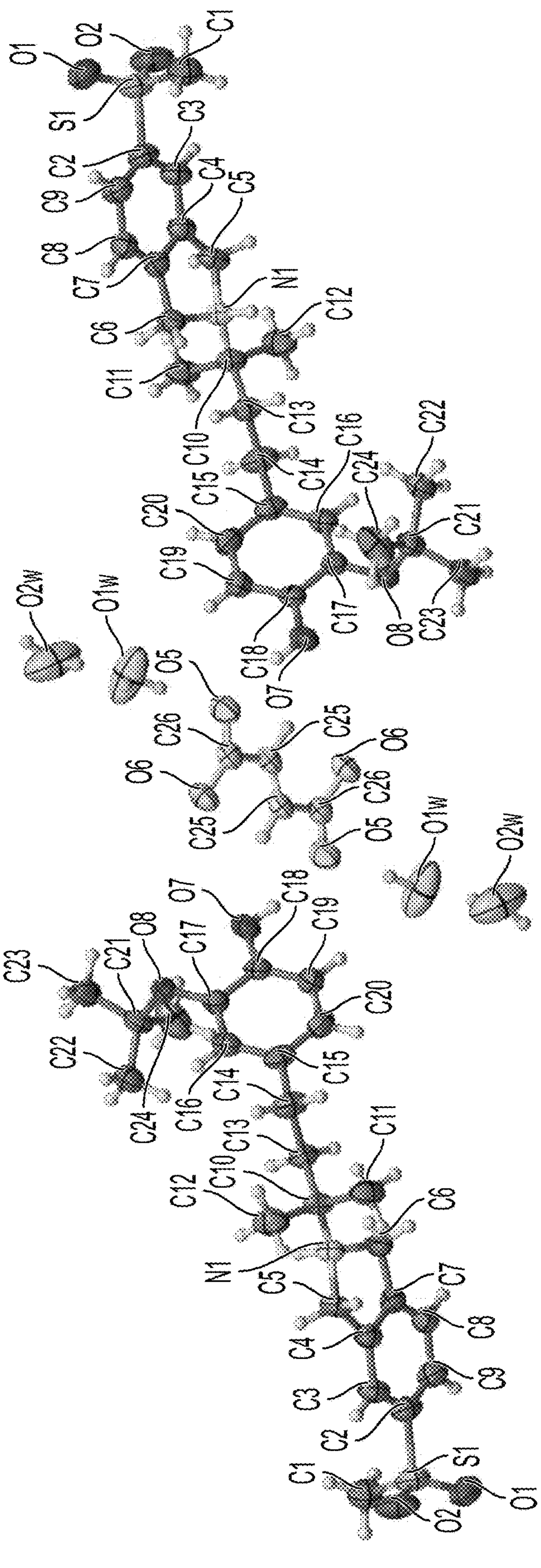
FIG. 14 is an ORTEP drawing of 2-(t-butoxy)-4-(3-methyl-3-(5-(methylsulfonyl)isoindolin-2-yl)butyl)phenol hemi-fumarate dihydrate salt, crystal form E. Non hydrogen atoms are drawn in ellipsoid at 75% probability level and hydrogen atoms are drawn in small circles.
Figure 15:
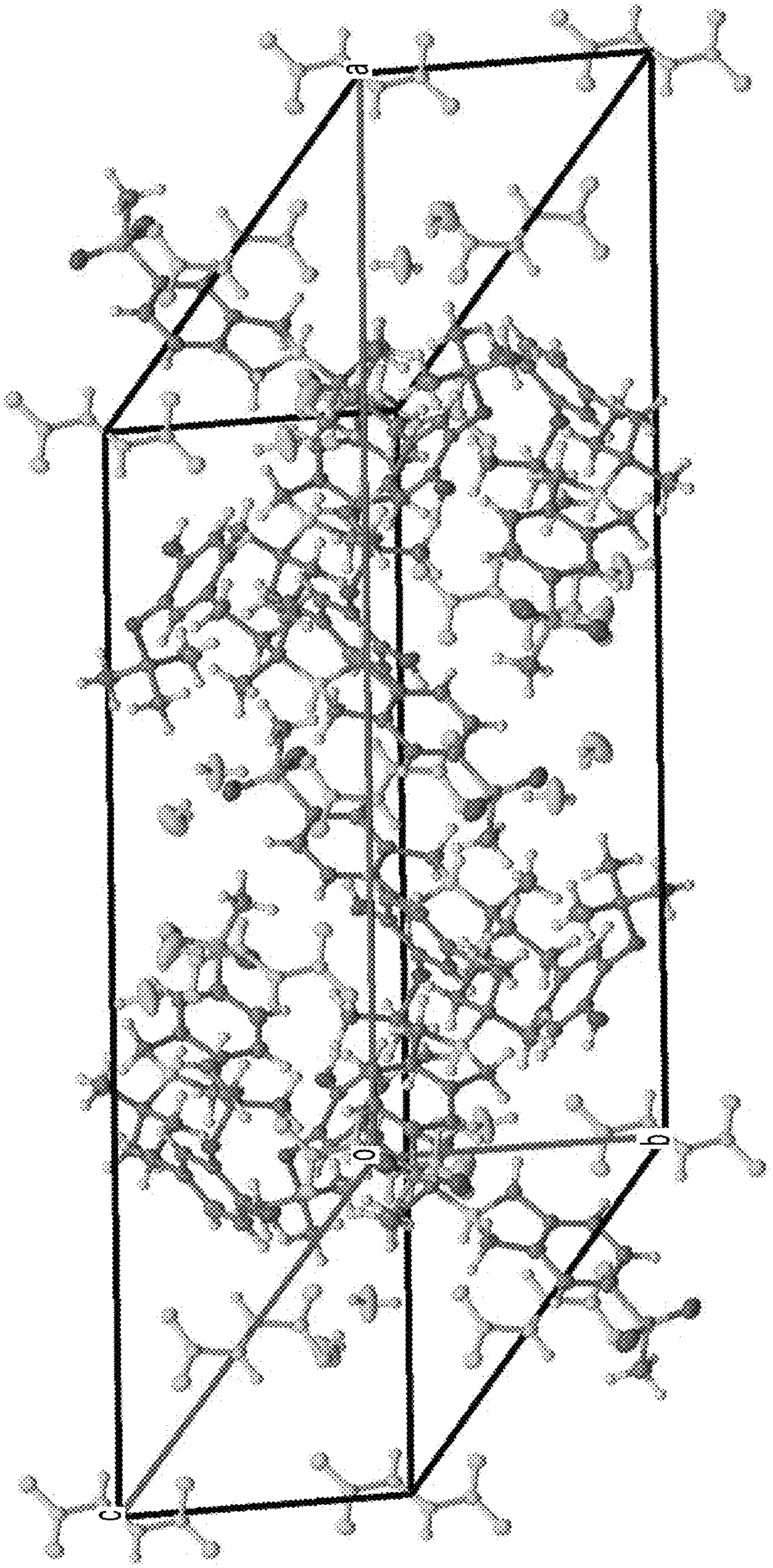
FIG. 15 is a unit cell of 2-(t-butoxy)-4-(3-methyl-3-(5-(methylsulfonyl)isoindolin-2-yl)butyl)phenol hemi-fumarate dihydrate salt, crystal form E, showing 8 molecules, 4 fumarate counterions and 16 water molecules.

In some aspects, 2-(t-butoxy)-4-(3-methyl-3-(5-(methylsulfonyl)isoindolin-2-yl)butyl)phenol hemi-fumarate dihydrate salt, crystal form E has a Fourier-transform infrared (FTIR) spectrum substantially as shown in FIG. 13.

In some aspects, 2-(t-butoxy)-4-(3-methyl-3-(5-(methylsulfonyl)isoindolin-2-yl)butyl)phenol hemi-fumarate dihydrate salt, crystal form E is described by an XRPD as described in any aspect of paragraphs [0106]-[0109] in combination with any aspect of DSC, as described in paragraph [0110], TGA as described in paragraph [0111] and/or FTIR as described in paragraph [0112].

In some aspects, 2-(t-butoxy)-4-(3-methyl-3-(5-(methylsulfonyl)isoindolin-2-yl)butyl)phenol hemi-fumarate dihydrate salt, crystal form E, according to any aspect described herein has a polymorph purity of at least 50%. In some aspects, crystal form E has a polymorph purity of at least 75%. In some aspects, crystal form E has a polymorph purity of at least 80%. In some aspects, crystal form E has a polymorph purity of at least 85%. In some aspects, crystal form E has a polymorph purity of at least 90%. In some aspects, crystal form E has a polymorph purity of at least 95%. In some aspects, crystal form E has a polymorph purity of at least 96%. In some aspects, crystal form E has a polymorph purity of at least 97%. In some aspects, crystal form E has a polymorph purity of at least 98%. In some aspects, crystal form E has a polymorph purity of at least 99%. In some aspects, crystal form E has a polymorph purity of about 95%. In some aspects, crystal form E has a polymorph purity of about 96%. In some aspects, crystal form E has a polymorph purity of about 97%. In some aspects, crystal form E has a polymorph purity of about 98%. In some aspects, crystal form E has a polymorph purity of about 99%.

In some aspects, 2-(t-butoxy)-4-(3-methyl-3-(5-(methylsulfonyl)isoindolin-2-yl)butyl)phenol hemi-fumarate dihydrate salt, crystal form E, according to any aspect described herein has a chemical purity of at least 50 A %. In some aspects, crystal form E has a chemical purity of at least 75 A %. In some aspects, crystal form E has a chemical purity of at least 80 A %. In some aspects, crystal form E has a chemical purity of at least 85 A %. In some aspects, crystal form E has a chemical purity of at least 90 A %. In some aspects, crystal form E has a chemical purity of at least 91 A %. In some aspects, crystal form E has a chemical purity of at least 92 A %. In some aspects, crystal form E has a chemical purity of at least 93 A %. In some aspects, crystal form E has a chemical purity of at least 94 A %. In some aspects, crystal form E has a chemical purity of at least 95 A %. In some aspects, crystal form E has a chemical purity of at least 96 A %. In some aspects, crystal form E has a chemical purity of at least 97 A %. In some aspects, crystal form E has a chemical purity of at least 98 A %. In some aspects, crystal form E has a chemical purity of at least 99 A %. In some aspects, crystal form E has a chemical purity of about 90 A %. In some aspects, crystal form E has a chemical purity of about 91 A %. In some aspects, crystal form E has a chemical purity of about 92 A %. In some aspects, crystal form E has a chemical purity of about 93 A %. In some aspects, crystal form E has a chemical purity of about 94 A %. In some aspects, crystal form E has a chemical purity of about 95 A %. In some aspects, crystal form E has a chemical purity of about 96 A %. In some aspects, crystal form E has a chemical purity of about 97 A %. In some aspects, crystal form E has a chemical purity of about 98 A %. In some aspects, crystal form E has a chemical purity of about 99 A %.

Figure 16:
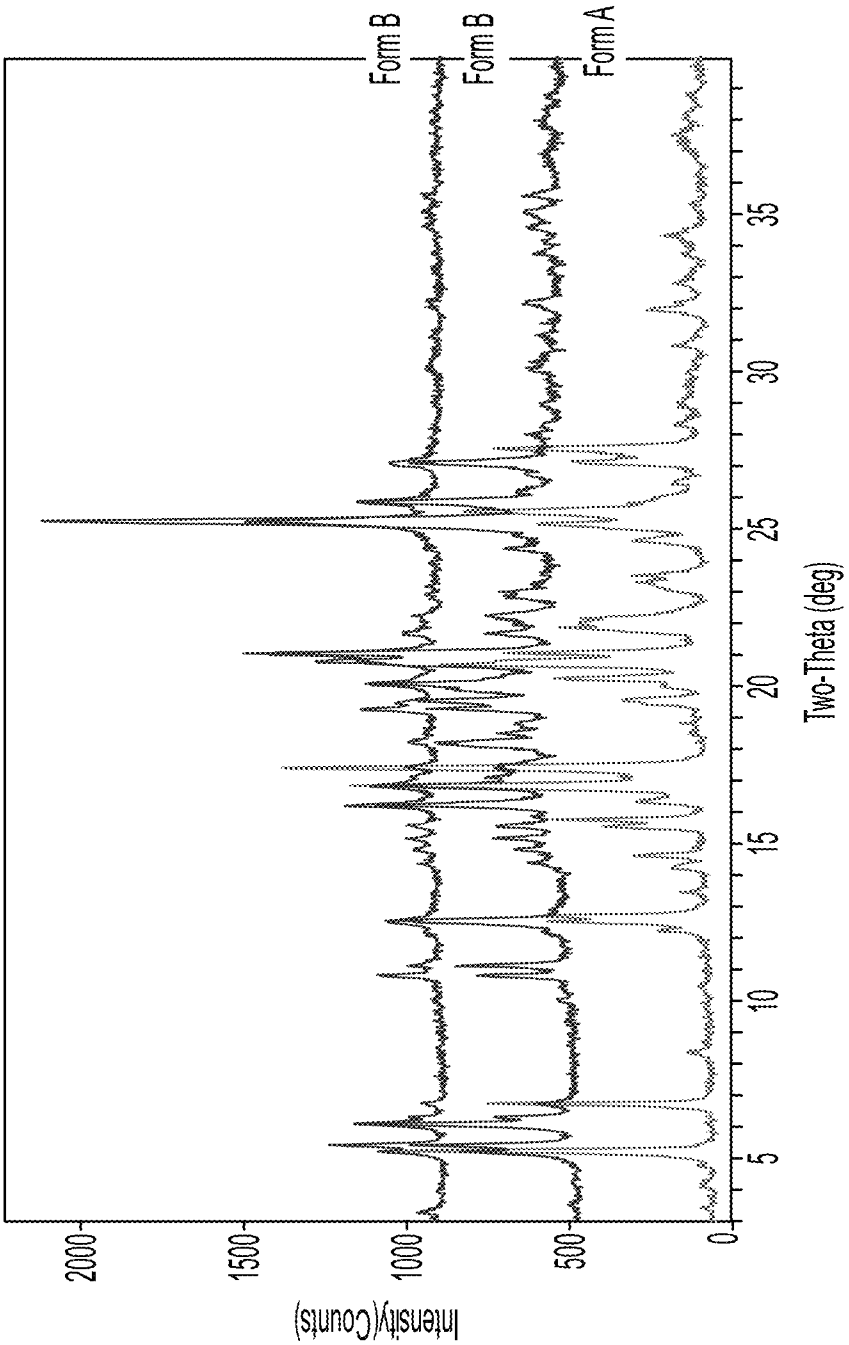
FIG. 16 is an X-ray powder diffraction pattern overlay of 2-(t-butoxy)-4-(3-methyl-3-(5-(methylsulfonyl)isoindolin-2-yl)butyl)phenol mono-fumarate salt, acetone solvate, crystal form B obtained by fast cooling of 2-(t-butoxy)-4-(3-methyl-3-(5-(methylsulfonyl)isoindolin-2-yl)butyl)phenol mono-fumarate salt, crystal form A in acetone (top XRPD and middle XRPD) overlayed with crystal form A (bottom XRPD).

In some aspects, the crystalline form is 2-(t-butoxy)-4-(3-methyl-3-(5-(methylsulfonyl)isoindolin-2-yl)butyl)phenol mono-fumarate salt, acetone solvate, crystal form B characterized by an X-ray powder diffraction (XRPD)pattern comprising at least three characteristic 2θ peaks at 6.09, 20.79, 21.05, 25.24, and 25.86° (±0.2°). In some aspects, the crystalline form is 2-(t-butoxy)-4-(3-methyl-3-(5-(methylsulfonyl)isoindolin-2-yl)butyl)phenol mono-fumarate salt, acetone solvate, crystal form B, is characterized by an X-ray powder diffraction (XRPD) pattern comprising characteristic 2θ peaks at 6.09, 20.79, 21.05, 25.24, and 25.86° (±0.2°). In some aspects, the XRPD of crystal form B further comprises additional peaks at 5.42, 12.55, 16.22, 16.83, and 20.08,° (±0.2°). In some aspects, the XRPD of crystal form B further comprises additional peaks at 0.20, 11.13, 18.18, 19.29, 19.55, and 27.100 (+0.2°). In some aspects, the XRPD of crystal form B further comprises peaks at 6.30, 10.81, 14.82, 15.18, 15.56, 17.08, 17.44, 18.50, 18.80, 21.68, 22.24, 22.89, and 24.38° (±0.2°). In some aspects, the XRPD of crystal form B is substantially as shown in FIG. 16. In some aspects, the XRPD of crystal form B comprises peaks as described in Table 4.

TABLE 4

XRPD 2-(t-butoxy)-4-(3-methyl-3-(5-(methylsulfonyl)isoindolin-2-yl)butyl)phenol mono-fumarate salt, acetone solvate, crystal form B

| Pos. °2θ | Rel. Int. % |
|---|---|
| 3.51 | 0.99 |
| 5.20 | 21.46 |
| 5.42 | 31.92 |
| 6.09 | 42.59 |
| 6.30 | 15.26 |
| 6.73 | 7.27 |
| 10.02 | 2.82 |

TABLE 4-continued

| XRPD 2-(t-butoxy)-4-(3-methyl-3-(5-(methylsulfonyl)isoindolin-2-yl)butyl)phenol mono-fumarate salt, acetone solvate, crystal form B | |
|---|---|
| Pos. °2θ | Rel. Int. % |
| 10.81 | 18.46 |
| 11.13 | 21.37 |
| 12.55 | 32.73 |
| 14.39 | 7.60 |
| 14.82 | 10.90 |
| 15.18 | 14.16 |
| 15.56 | 14.15 |
| 16.22 | 37.23 |
| 16.83 | 33.81 |
| 17.08 | 13.11 |
| 17.44 | 13.58 |
| 18.18 | 23.43 |
| 18.50 | 13.46 |
| 18.80 | 9.98 |
| 19.29 | 25.59 |
| 19.55 | 29.25 |
| 20.08 | 38.79 |
| 20.79 | 48.29 |
| 21.05 | 61.69 |
| 21.68 | 15.84 |
| 22.24 | 15.61 |
| 22.89 | 10.35 |
| 24.38 | 12.14 |
| 25.24 | 100 |
| 25.86 | 40.10 |
| 27.10 | 29.52 |
| 27.96 | 6.09 |
| 28.95 | 4.47 |
| 30.07 | 6.16 |
| 31.11 | 3.78 |
| 32.19 | 6.88 |
| 33.77 | 4.61 |
| 34.58 | 5.78 |
| 35.06 | 6.94 |
| 35.60 | 6.48 |
| 36.83 | 2.62 |
| 38.02 | 2.86 |

Figure 17:
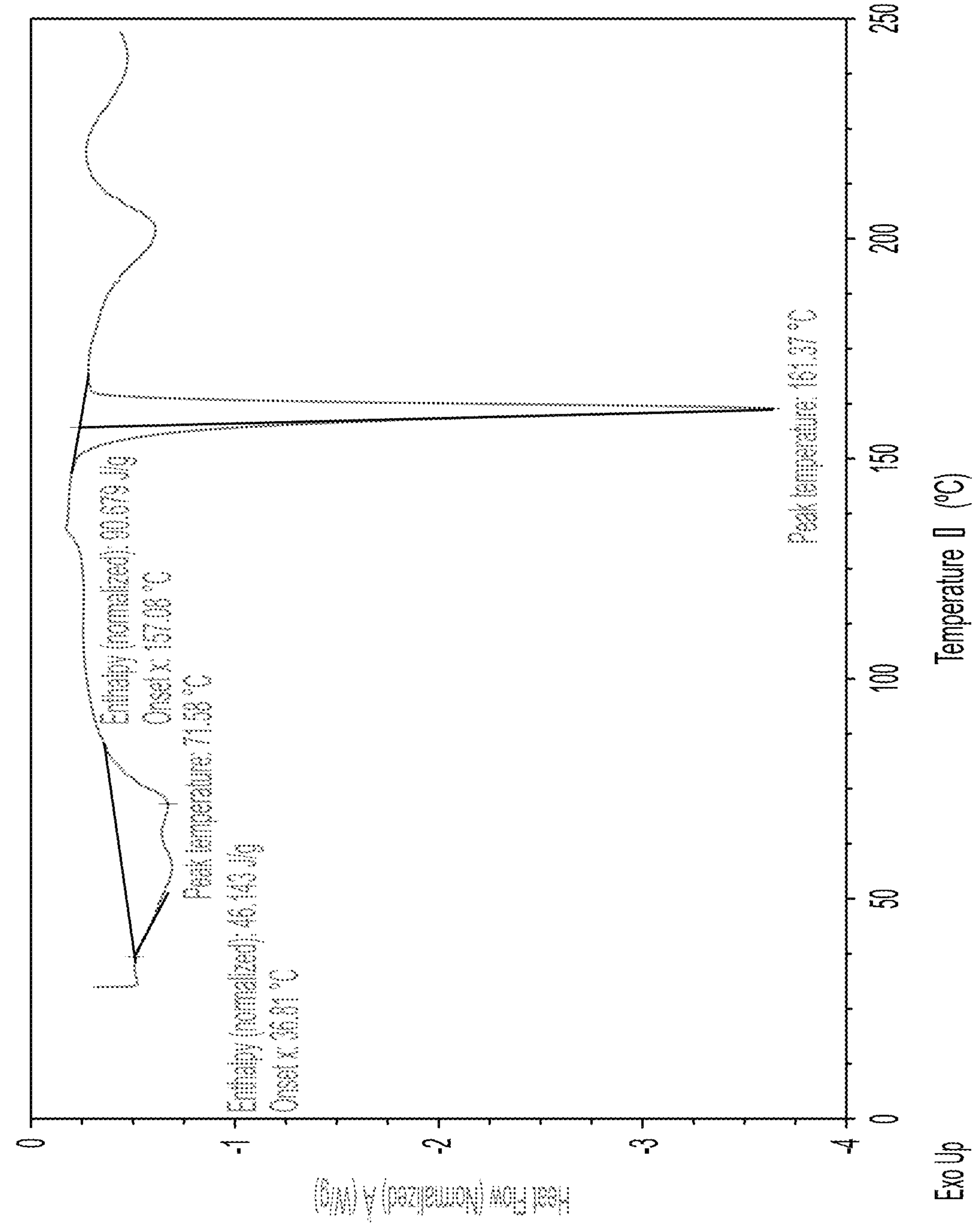
FIG. 17 is a differential scanning calorimetry (DSC) curve of 2-(t-butoxy)-4-(3-methyl-3-(5-(methylsulfonyl)isoindolin-2-yl)butyl)phenol mono-fumarate salt, acetone solvate, crystal form B.

In some aspects, 2-(t-butoxy)-4-(3-methyl-3-(5-(methylsulfonyl)isoindolin-2-yl)butyl)phenol mono-fumarate salt, acetone solvate, crystal form B is characterized by a differential scanning calorimetry (DSC) curve that shows multiple thermal events (including an endothermic peak at about 161.37° C.). In some aspects, the DSC of crystal form B is substantially as shown in FIG. 17.

Figure 18:
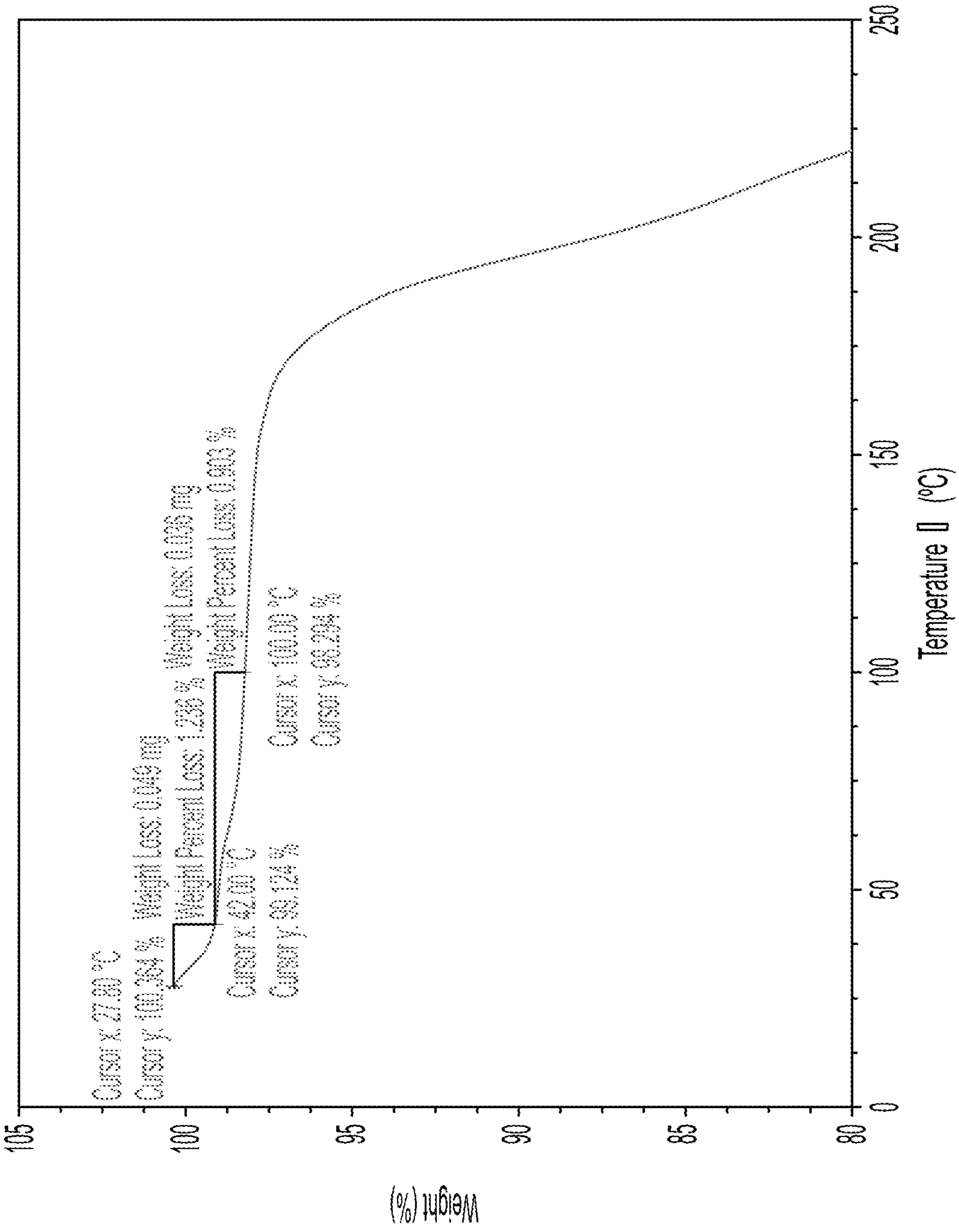
FIG. 18 is a thermogravimetric analysis (TGA) of 2-(t-butoxy)-4-(3-methyl-3-(5-(methylsulfonyl)isoindolin-2-yl)butyl)phenol mono-fumarate salt, acetone solvate, crystal form B

In some aspects, 2-(t-butoxy)-4-(3-methyl-3-(5-(methylsulfonyl)isoindolin-2-yl)butyl)phenol mono-fumarate salt, acetone solvate, crystal form B shows mass losses of about 1.2% at about 42.0° C. followed by about 2.1% at about 100.0° C. by thermogravimetric analysis (TGA). In some aspects, the TGA of crystal form B is substantially as shown in FIG. 18.

In some aspects, 2-(t-butoxy)-4-(3-methyl-3-(5-(methylsulfonyl)isoindolin-2-yl)butyl)phenol mono-fumarate salt, acetone solvate, crystal form B is described by an XRPD as described in any aspect of paragraphs [0116]-[0117] in combination with any aspect of DSC, as described in paragraph [0118], and/or TGA as described in paragraph [0119].

In some aspects, 2-(t-butoxy)-4-(3-methyl-3-(5-(methylsulfonyl)isoindolin-2-yl)butyl)phenol mono-fumarate salt, acetone solvate, crystal form B according to any aspect described herein has a polymorph purity of at least 50%. In some aspects, crystal form B has a polymorph purity of at least 75%. In some aspects, crystal form B has a polymorph purity of at least 80%. In some aspects, crystal form B has a polymorph purity of at least 85%. In some aspects, crystal form B has a polymorph purity of at least 90%. In some aspects, crystal form B has a polymorph purity of at least 95%. In some aspects, crystal form B has a polymorph purity of at least 96%. In some aspects, crystal form B has a polymorph purity of at least 97%. In some aspects, crystal form B has a polymorph purity of at least 98%. In some aspects, crystal form B has a polymorph purity of at least 99%. In some aspects, crystal form B has a polymorph purity of about 95%. In some aspects, crystal form B has a polymorph purity of about 96%. In some aspects, crystal form B has a polymorph purity of about 97%. In some aspects, crystal form B has a polymorph purity of about 98%. In some aspects, crystal form B has a polymorph purity of about 99%.

In some aspects, 2-(t-butoxy)-4-(3-methyl-3-(5-(methylsulfonyl)isoindolin-2-yl)butyl)phenol mono-fumarate salt, acetone solvate, crystal form B according to any aspect described herein has a chemical purity of at least 50 A %. In some aspects, crystal form B has a chemical purity of at least 75 A %. In some aspects, crystal form B has a chemical purity of at least 80 A %. In some aspects, crystal form B has a chemical purity of at least 85 A %. In some aspects, crystal form B has a chemical purity of at least 90 A %. In some aspects, crystal form B has a chemical purity of at least 91 A %. In some aspects, crystal form B has a chemical purity of at least 92 A %. In some aspects, crystal form B has a chemical purity of at least 93 A %. In some aspects, crystal form B has a chemical purity of at least 94 A %. In some aspects, crystal form B has a chemical purity of at least 95 A %. In some aspects, crystal form B has a chemical purity of at least 96 A %. In some aspects, crystal form B has a chemical purity of at least 97 A %. In some aspects, crystal form B has a chemical purity of at least 98 A %. In some aspects, crystal form B has a chemical purity of at least 99 A %. In some aspects, crystal form B has a chemical purity of about 90 A %. In some aspects, crystal form B has a chemical purity of about 91 A %. In some aspects, crystal form B has a chemical purity of about 92 A %. In some aspects, crystal form B has a chemical purity of about 93 A %. In some aspects, crystal form B has a chemical purity of about 94 A %. In some aspects, crystal form B has a chemical purity of about 95 A %. In some aspects, crystal form B has a chemical purity of about 96 A %. In some aspects, crystal form B has a chemical purity of about 97 A %. In some aspects, crystal form B has a chemical purity of about 98 A %. In some aspects, crystal form B has a chemical purity of about 99 A %.

Figure 24:
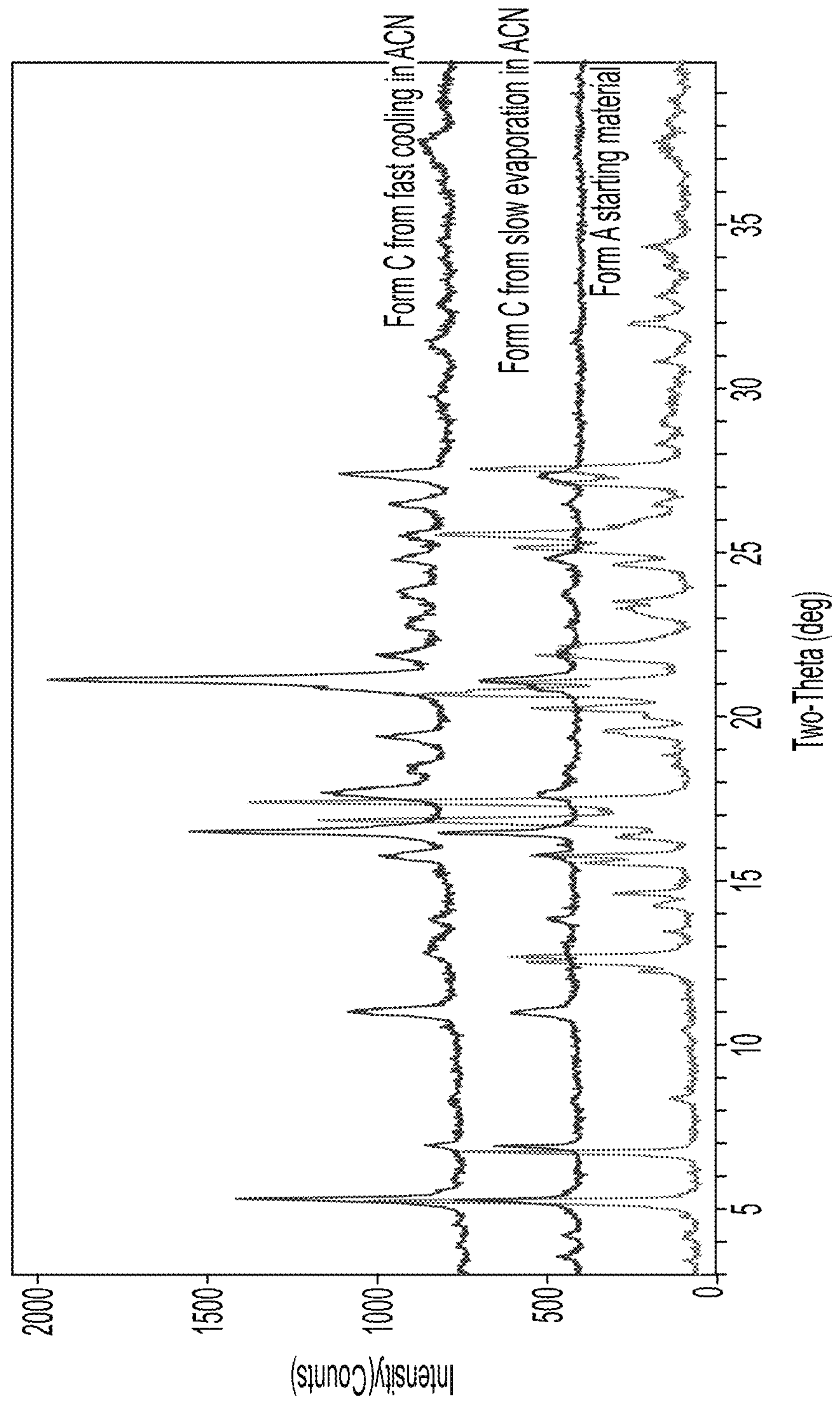
FIG. 24 is an X-ray powder diffraction pattern overlay of polymorphs obtained from 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol mono-fumarate salt, acetonitrile solvate, crystal form C obtained by fast cooling in ACN. The middles XRPD is of 2-(t-butoxy)-4-(3-methyl-3-(5-(methylsulfonyl)isoindolin-2-yl)butyl)phenol mono-fumarate salt, acetonitrile solvate, crystal form C obtained by slow evaporation at room temperature in ACN. The bottom XRPD is 2-(t-butoxy)-4-(3-methyl-3-(5-(methylsulfonyl)isoindolin-2-yl)butyl)phenol mono-fumarate salt, crystal form A

In some aspects, the crystalline form is 2-(t-butoxy)-4-(3-methyl-3-(5-(methylsulfonyl)isoindolin-2-yl)butyl)phenol mono-fumarate salt, acetonitrile solvate, crystal form C characterized by an X-ray powder diffraction (XRPD)pattern comprising at least three characteristic 2θ peaks at 5.27, 16.47, 17.65, 19.36, and 21.09° (±0.2°). In some aspects, the crystalline form is 2-(t-butoxy)-4-(3-methyl-3-(5-(methylsulfonyl)isoindolin-2-yl)butyl)phenol mono-fumarate salt, acetonitrile solvate, crystal form C characterized by an X-ray powder diffraction (XRPD) pattern comprising characteristic 2θ peaks at 5.27, 16.47, 17.65, 19.36, and 21.09° (±0.2°). In some aspects, the XRPD of 2-(t-butoxy)-4-(3-methyl-3-(5-(methylsulfonyl)isoindolin-2-yl)butyl)phenol mono-fumarate salt, acetonitrile solvate, crystal form C further comprises additional peaks at 10.95, 12.71, 15.74, 20.79, 21.82, 25.53, and 27.37° (±0.2°). In some aspects, the XRPD of crystal form C further comprises additional peaks at 11.09, 16.22, 17.36, and 24.80° (+0.2°). In some aspects, the XRPD of crystal form C further comprises peaks at 6.73, 18.42, 22.71, 22.88, 23.16, 23.79 and 26.43° (±0.2°). In some aspects, the XRPD of crystal form C of 2-(t-butoxy)-4-(3-methyl-3-(5-(methylsulfonyl)isoindolin-2-yl)butyl)

phenol mono-fumarate salt is substantially as shown in FIG. 24. In some aspects, the XRPD of crystal form C comprises peaks as described in Table 5.

TABLE 5

XRPD 2-theta values of 2-(t-butoxy)-4-(3-methyl-3-(5-(methylsulfonyl)isoindolin-2-yl)butyl)phenol mono-fumarate salt, acetonitrile solvate, crystal form C.

| Pos. °2θ | Rel. Int. % |
|---|---|
| 5.27 | 77.69 |
| 5.53 | 6.75 |
| 6.73 | 15.85 |
| 6.90 | 11.01 |
| 8.32 | 8.24 |
| 10.95 | 38.38 |
| 11.09 | 23.57 |
| 12.71 | 29.60 |
| 13.10 | 11.47 |
| 13.78 | 11.05 |
| 15.10 | 12.04 |
| 15.74 | 30.02 |
| 16.22 | 22.94 |
| 16.47 | 94.33 |
| 17.36 | 26.09 |
| 17.65 | 50.02 |
| 18.42 | 18.66 |
| 19.36 | 46.72 |
| 20.26 | 11.71 |
| 20.79 | 36.08 |
| 21.09 | 100 |
| 21.82 | 31.56 |
| 22.71 | 15.14 |
| 22.88 | 15.89 |
| 23.16 | 13.73 |
| 23.79 | 19.70 |
| 24.32 | 9.26 |
| 24.80 | 21.86 |
| 25.53 | 40.69 |
| 26.12 | 9.70 |
| 26.43 | 16.50 |
| 27.37 | 38.73 |
| 29.70 | 8.13 |
| 30.08 | 6.21 |
| 31.39 | 6.63 |
| 31.76 | 4.66 |
| 32.57 | 5.72 |
| 34.45 | 4.60 |
| 35.01 | 4.87 |
| 36.22 | 4.43 |
| 37.00 | 6.16 |
| 37.49 | 10.56 |
| 38.46 | 6.01 |
| 39.27 | 4.04 |

Figure 22:
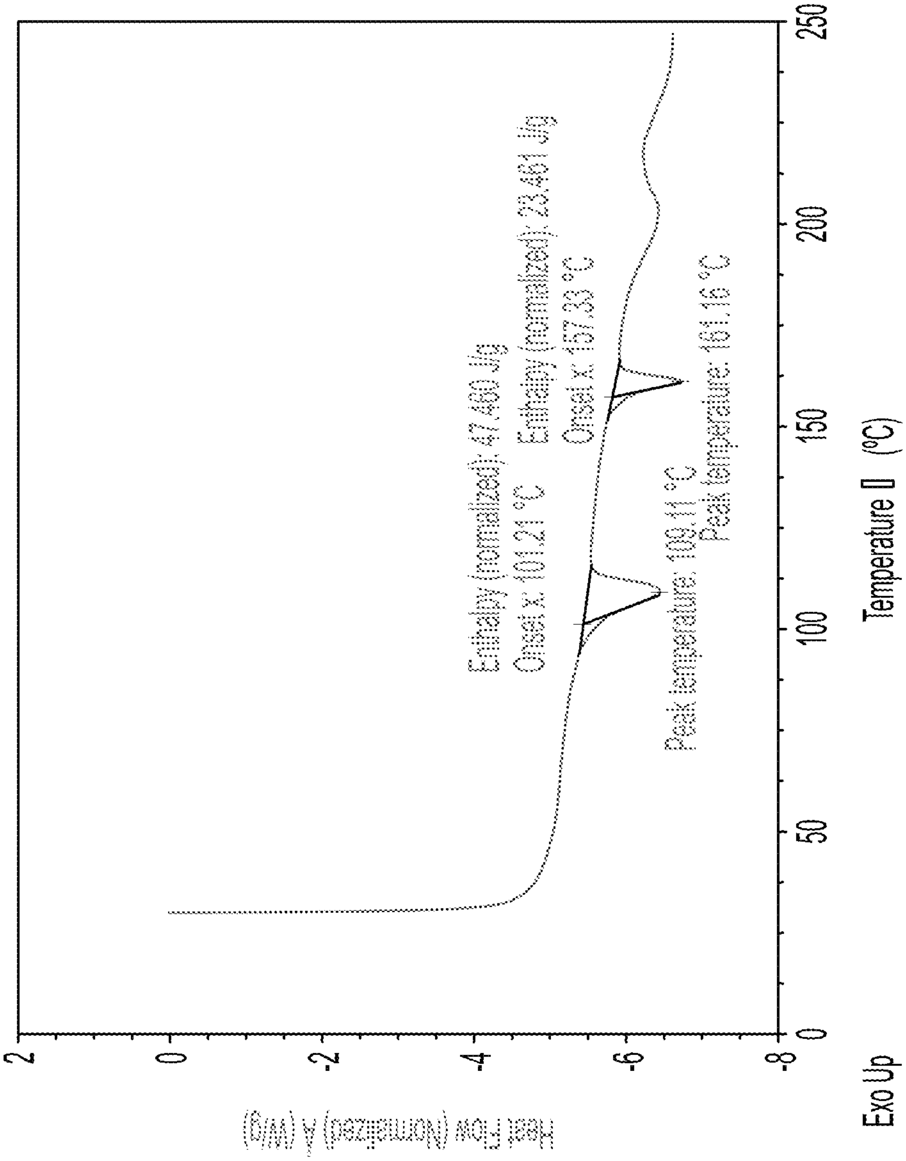
FIG. 22 is a differential scanning calorimetry (DSC) curve of 2-(t-butoxy)-4-(3-methyl-3-(5-(methylsulfonyl)isoindolin-2-yl)butyl)phenol mono-fumarate salt, acetonitrile solvate, crystal form C.

In some aspects, 2-(t-butoxy)-4-(3-methyl-3-(5-(methylsulfonyl)isoindolin-2-yl)butyl)phenol mono-fumarate salt, acetonitrile solvate, crystal form C. is characterized by a differential scanning calorimetry (DSC) curve that comprises thermal events at onset of about 101.2° C. and about 157.3° C. In some aspects, the DSC of crystal form C is substantially as shown in FIG. 22.

Figure 23:
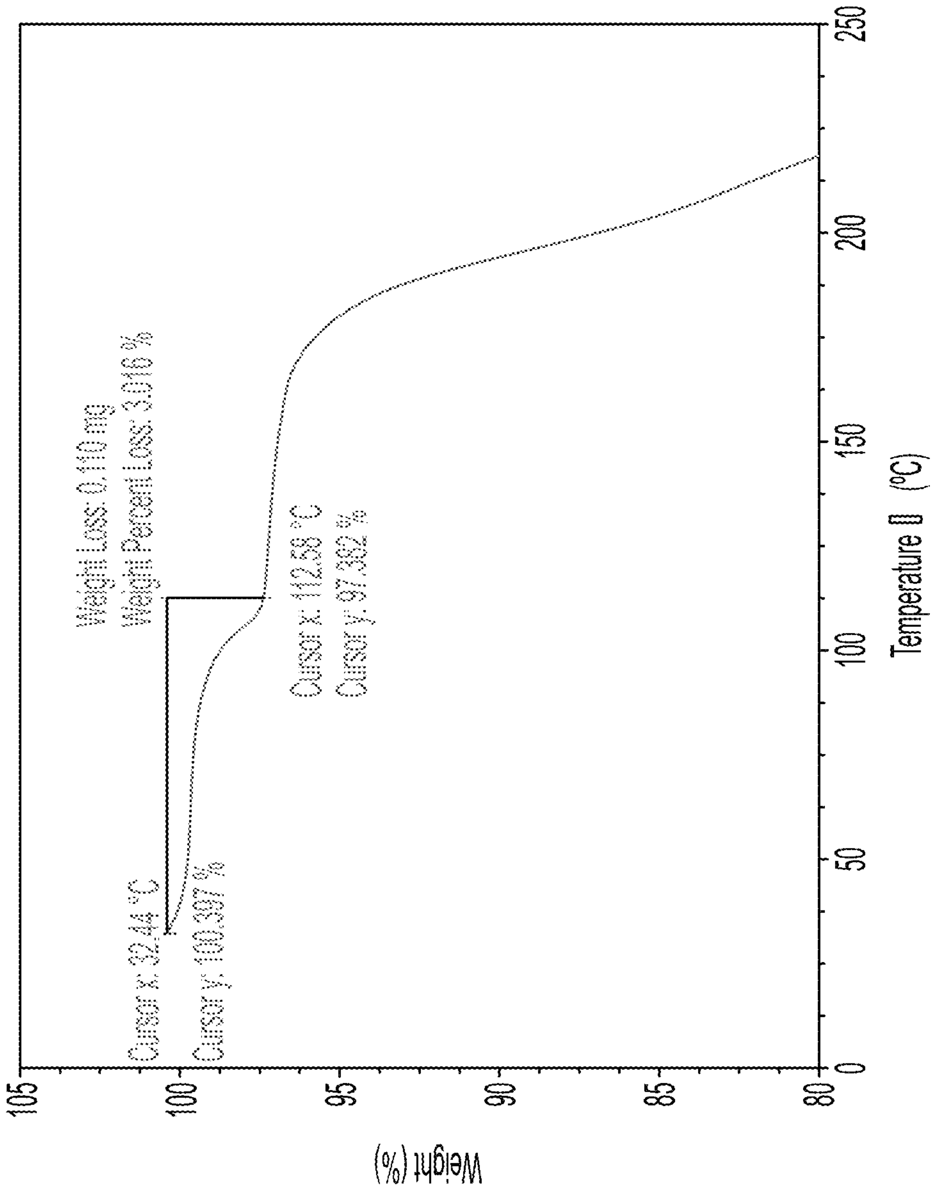
FIG. 23 is a thermogravimetric analysis (TGA) of 2-(t-butoxy)-4-(3-methyl-3-(5-(methylsulfonyl)isoindolin-2-yl)butyl)phenol mono-fumarate salt, acetonitrile solvate (form C).

In some aspects, 2-(t-butoxy)-4-(3-methyl-3-(5-(methylsulfonyl)isoindolin-2-yl)butyl)phenol mono-fumarate salt, acetonitrile solvate, crystal form C. shows a mass loss of about 3.0% at about 112.6° C. by thermogravimetric analysis (TGA). In some aspects, the TGA of crystal form C is substantially as shown in FIG. 23.

In some aspects, 2-(t-butoxy)-4-(3-methyl-3-(5-(methylsulfonyl)isoindolin-2-yl)butyl)phenol mono-fumarate salt, acetonitrile solvate, crystal form C is described by an XRPD as described in any aspect of paragraphs [0123]-[0124] in combination with any aspect of DSC, as described in paragraph [0125], and/or TGA as described in paragraph [0126].

In some aspects, 2-(t-butoxy)-4-(3-methyl-3-(5-(methylsulfonyl)isoindolin-2-yl)butyl)phenol mono-fumarate salt, acetonitrile solvate, crystal form C according to any aspect described herein has a polymorph purity of at least 50%. In some aspects, crystal form C has a polymorph purity of at least 75%. In some aspects, crystal form C has a polymorph purity of at least 80%. In some aspects, crystal form C has a polymorph purity of at least 85%. In some aspects, crystal form C has a polymorph purity of at least 90%. In some aspects, crystal form C has a polymorph purity of at least 95%. In some aspects, crystal form C has a polymorph purity of at least 96%. In some aspects, crystal form C has a polymorph purity of at least 97%. In some aspects, crystal form C has a polymorph purity of at least 98%. In some aspects, crystal form C has a polymorph purity of at least 99%. In some aspects, crystal form C has a polymorph purity of about 95%. In some aspects, crystal form C has a polymorph purity of about 96%. In some aspects, crystal form C has a polymorph purity of about 97%. In some aspects, crystal form C has a polymorph purity of about 98%. In some aspects, crystal form C has a polymorph purity of about 99%.

In some aspects, 2-(t-butoxy)-4-(3-methyl-3-(5-(methylsulfonyl)isoindolin-2-yl)butyl)phenol mono-fumarate salt, acetonitrile solvate, crystal form C according to any aspect described herein has a chemical purity of at least 50 A %. In some aspects, crystal form C has a chemical purity of at least 75 A %. In some aspects, crystal form C has a chemical purity of at least 80 A %. In some aspects, crystal form C has a chemical purity of at least 85 A %. In some aspects, crystal form C has a chemical purity of at least 90 A %. In some aspects, crystal form C has a chemical purity of at least 91 A %. In some aspects, crystal form C has a chemical purity of at least 92 A %. In some aspects, crystal form C has a chemical purity of at least 93 A %. In some aspects, crystal form C has a chemical purity of at least 94 A %. In some aspects, crystal form C has a chemical purity of at least 95 A %. In some aspects, crystal form C has a chemical purity of at least 96 A %. In some aspects, crystal form C has a chemical purity of at least 97 A %. In some aspects, crystal form C has a chemical purity of at least 98 A %. In some aspects, crystal form C has a chemical purity of at least 99 A %. In some aspects, crystal form C has a chemical purity of about 90 A %. In some aspects, crystal form C has a chemical purity of about 91 A %. In some aspects, crystal form C has a chemical purity of about 92 A %. In some aspects, crystal form C has a chemical purity of about 93 A %. In some aspects, crystal form C has a chemical purity of about 94 A %. In some aspects, crystal form C has a chemical purity of about 95 A %. In some aspects, crystal form C has a chemical purity of about 96 A %. In some aspects, crystal form C has a chemical purity of about 97 A %. In some aspects, crystal form C has a chemical purity of about 98 A %. In some aspects, crystal form C has a chemical purity of about 99 A %.

Figure 25:
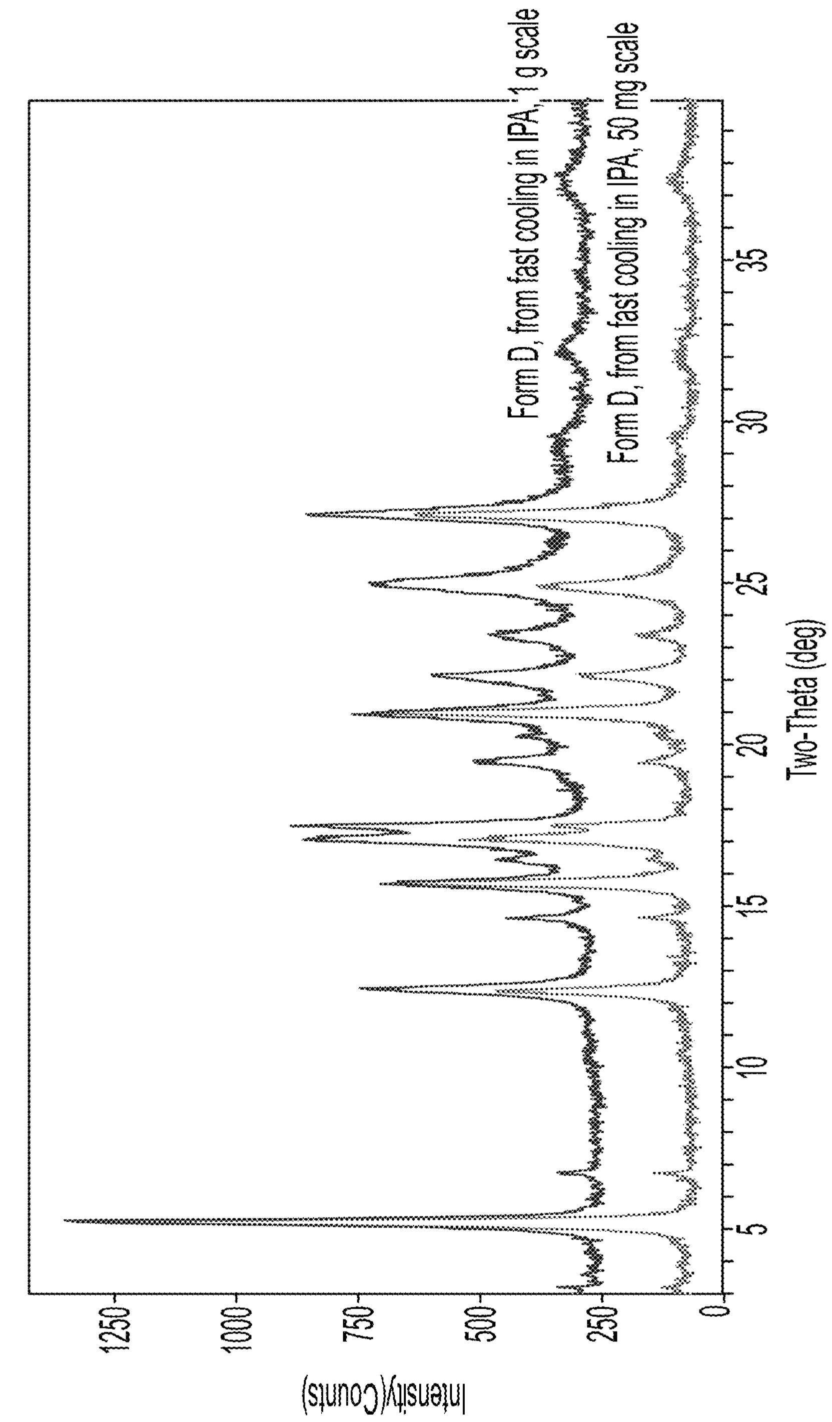
FIG. 25 is an X-ray powder diffraction pattern overlay of 2-(t-butoxy)-4-(3-methyl-3-(5-(methylsulfonyl)isoindolin-2-yl)butyl)phenol mono-fumarate salt, crystal form D obtained by fast cooling of 2-(t-butoxy)-4-(3-methyl-3-(5-(methylsulfonyl)isoindolin-2-yl)butyl)phenol mono-fumarate salt, crystal form A in IPA. The top XRPD is on a 1 g scale of crystal form A, and the bottom XRPD is on a 50 mg scale of crystal form A.

In some aspects, the crystalline form is 2-(t-butoxy)-4-(3-methyl-3-(5-(methylsulfonyl)isoindolin-2-yl)butyl)phenol mono-fumarate salt, crystal form D characterized by an X-ray powder diffraction (XRPD) pattern comprising at least three characteristic 2θ peaks at 5.24, 17.06, 17.49, and 27.12° (±0.2°). In some aspects, the crystalline form is 2-(t-butoxy)-4-(3-methyl-3-(5-(methylsulfonyl)isoindolin-2-yl)butyl)phenol mono-fumarate salt, crystal form D characterized by an X-ray powder diffraction (XRPD) pattern comprising characteristic 2θ peaks at 5.24, 17.06, 17.49, and 27.12° (±0.2°). In some aspects, the XRPD of 2-(t-butoxy)-4-(3-methyl-3-(5-(methylsulfonyl)isoindolin-2-yl)butyl)

phenol mono-fumarate salt, crystal form D further comprises additional peaks at 12.44, 15.70, 20.95, 24.87, and 25.12° (±0.2°). In some aspects, the XRPD of crystal form D further comprises additional peaks at 19.48, 22.14, and 24.70° (±0.2°). In some aspects, the XRPD of crystal form D further comprises peaks at 14.63, 16.44, 20.26, and 23.370 (±0.2°). In some aspects, the XRPD 2-(t-butoxy)-4-(3-methyl-3-(5-(methylsulfonyl)isoindolin-2-yl)butyl)phenol mono-fumarate salt, crystal form D is substantially as shown in FIG. 25. In some aspects, the XRPD of crystal form D comprises peaks as described in Table 6.

TABLE 6

XRPD 2-theta values of 2-(t-butoxy)-4-(3-methyl-3-(5-(methylsulfonyl)isoindolin-2-yl)butyl)phenol mono-fumarate salt, crystal form D

| Pos. °2θ | Rel. Int. % |
|---|---|
| 5.24 | 1 |
| 6.74 | 6.04 |
| 12.44 | 42.62 |
| 14.63 | 16.39 |
| 15.70 | 38.79 |
| 16.44 | 18.61 |
| 17.06 | 55.69 |
| 17.49 | 55.48 |
| 19.48 | 21.25 |
| 20.26 | 14.41 |
| 20.95 | 41.96 |
| 22.14 | 29.08 |
| 23.37 | 18.60 |
| 24.70 | 24.38 |
| 24.87 | 37.17 |
| 25.12 | 36.43 |
| 27.12 | 53.03 |
| 32.21 | 4.39 |
| 37.63 | 4.17 |

Figure 26:
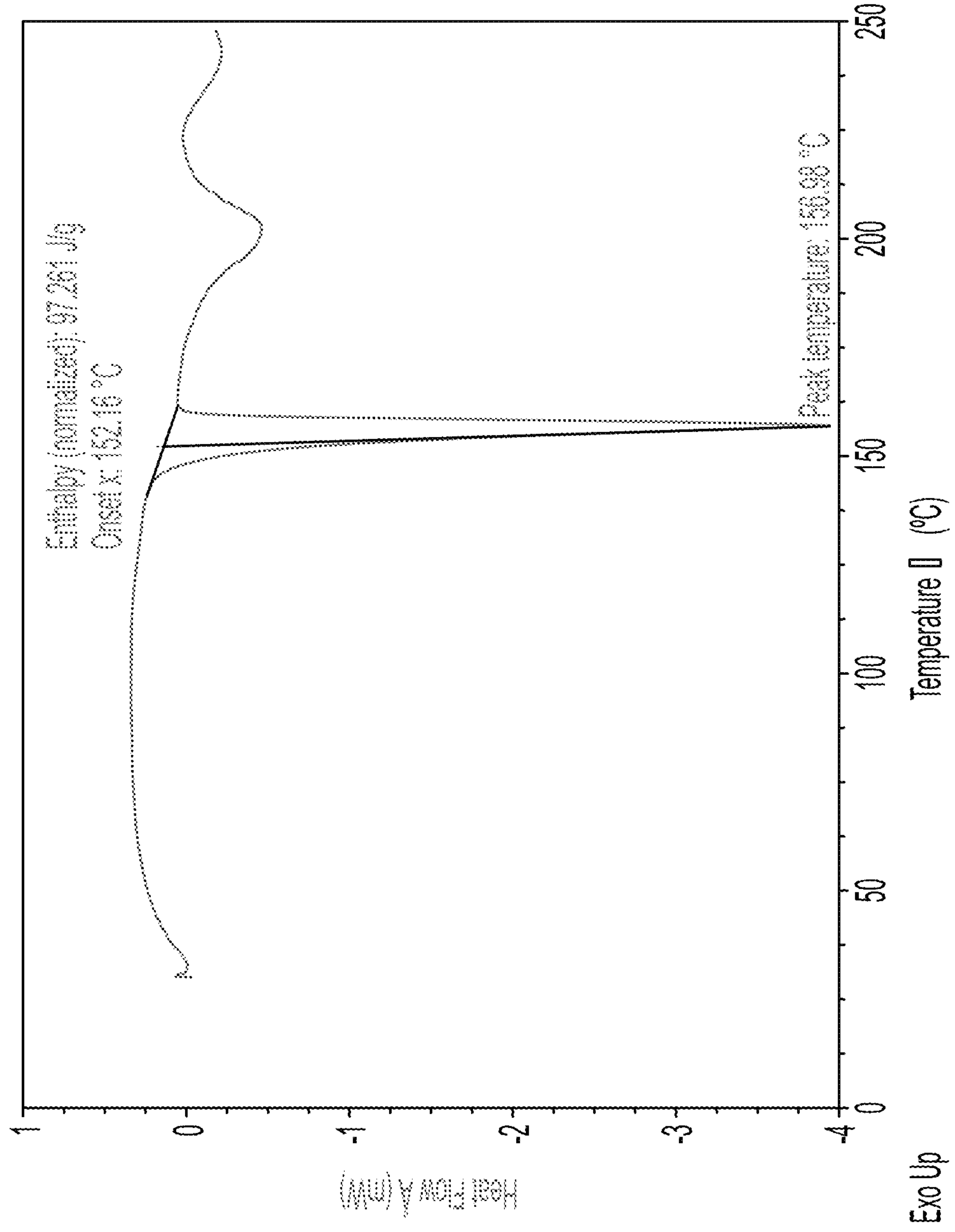
FIG. 26 is a differential scanning calorimetry (DSC) curve of 2-(t-butoxy)-4-(3-methyl-3-(5-(methylsulfonyl)isoindolin-2-yl)butyl)phenol mono-fumarate salt, crystal form D.

In some aspects, the DSC of 2-(t-butoxy)-4-(3-methyl-3-(5-(methylsulfonyl)isoindolin-2-yl)butyl)phenol mono-fumarate salt, crystal form D shows a T onset at about 152.2° C. and an enthalpy of about 97 J/g. In some aspects, the DSC of 2-(t-butoxy)-4-(3-methyl-3-(5-(methylsulfonyl)isoindolin-2-yl)butyl)phenol mono-fumarate salt, crystal form D is substantially as shown in FIG. 26.

Figure 27:
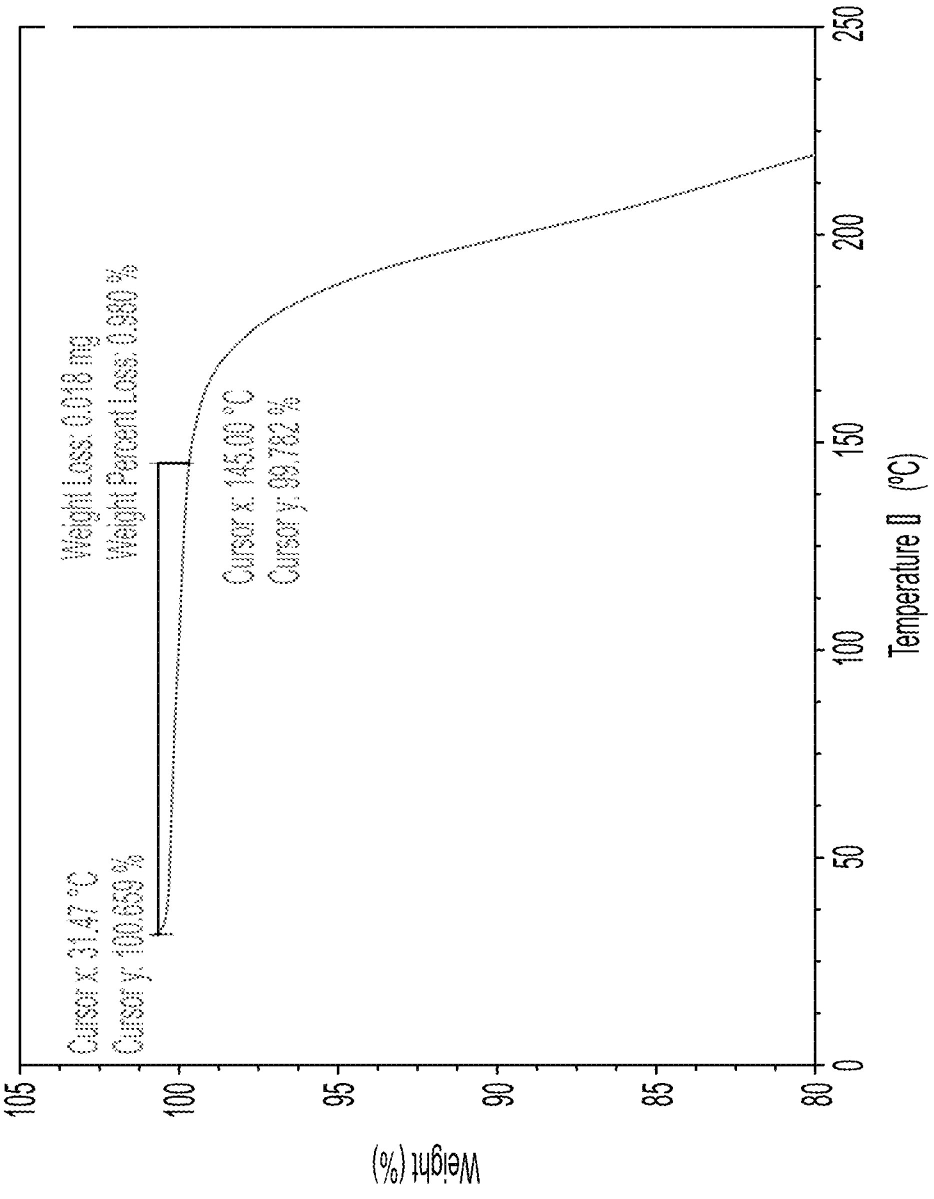
FIG. 27 is a thermogravimetric analysis (TGA) of 2-(t-butoxy)-4-(3-methyl-3-(5-(methylsulfonyl)isoindolin-2-yl)butyl)phenol mono-fumarate salt, crystal form D.

In some aspects, 2-(t-butoxy)-4-(3-methyl-3-(5-(methylsulfonyl)isoindolin-2-yl)butyl)phenol mono-fumarate salt, crystal form D shows a mass loss of about 1.0% at about 145.0° C. by thermogravimetric analysis (TGA). In some aspects, the TGA of crystal form D is substantially as shown in FIG. 27.

In some aspects, 2-(t-butoxy)-4-(3-methyl-3-(5-(methylsulfonyl)isoindolin-2-yl)butyl)phenol mono-fumarate salt, crystal form D is described by an XRPD as described in any aspect of paragraphs [0130]-[0131] in combination with any aspect of DSC, as described in paragraph [0132], and/or TGA as described in paragraph [0133].

In some aspects, 2-(t-butoxy)-4-(3-methyl-3-(5-(methylsulfonyl)isoindolin-2-yl)butyl)phenol mono-fumarate salt, crystal form D according to any aspect described herein has a polymorph purity of at least 50%. In some aspects, crystal form D has a polymorph purity of at least 75%. In some aspects, crystal form D has a polymorph purity of at least 80%. In some aspects, crystal form D has a polymorph purity of at least 85%. In some aspects, crystal form D has a polymorph purity of at least 90%. In some aspects, crystal form D has a polymorph purity of at least 95%. In some aspects, crystal form D has a polymorph purity of at least 96%. In some aspects, crystal form D has a polymorph purity of at least 97%. In some aspects, crystal form D has a polymorph purity of at least 98%. In some aspects, crystal form D has a polymorph purity of at least 99%. In some aspects, crystal form D has a polymorph purity of about 95%. In some aspects, crystal form D has a polymorph purity of about 96%. In some aspects, crystal form D has a polymorph purity of about 97%. In some aspects, crystal form D has a pglymorph purity of about 98%. In some aspects, crystal form D has a polymorph purity of about 99%.

In some aspects, 2-(t-butoxy)-4-(3-methyl-3-(5-(methylsulfonyl)isoindolin-2-yl)butyl)phenol mono-fumarate salt, crystal form D according to any aspect described herein has a chemical purity of at least 50 A %. In some aspects, crystal form D has a chemical purity of at least 75 A %. In some aspects, crystal form D has a chemical purity of at least 80 A %. In some aspects, crystal form D has a chemical purity of at least 85 A %. In some aspects, crystal form D has a chemical purity of at least 90 A %. In some aspects, crystal form D has a chemical purity of at least 91 A %. In some aspects, crystal form D has a chemical purity of at least 92 A %. In some aspects, crystal form D has a chemical purity of at least 93 A %. In some aspects, crystal form D has a chemical purity of at least 94 A %. In some aspects, crystal form D has a chemical purity of at least 95 A %. In some aspects, crystal form D has a chemical purity of at least 96 A %. In some aspects, crystal form D has a chemical purity of at least 97 A %. In some aspects, crystal form D has a chemical purity of at least 98 A %. In some aspects, crystal form D has a chemical purity of at least 99 A %. In some aspects, crystal form D has a chemical purity of about 90 A %. In some aspects, crystal form D has a chemical purity of about 91 A %. In some aspects, crystal form D has a chemical purity of about 92 A %. In some aspects, crystal form D has a chemical purity of about 93 A %. In some aspects, crystal form D has a chemical purity of about 94 A %. In some aspects, crystal form D has a chemical purity of about 95 A %. In some aspects, crystal form D has a chemical purity of about 96 A %. In some aspects, crystal form D has a chemical purity of about 97 A %. In some aspects, crystal form D has a chemical purity of about 98 A %. In some aspects, crystal form D has a chemical purity of about 99 A %.

Figure 29:
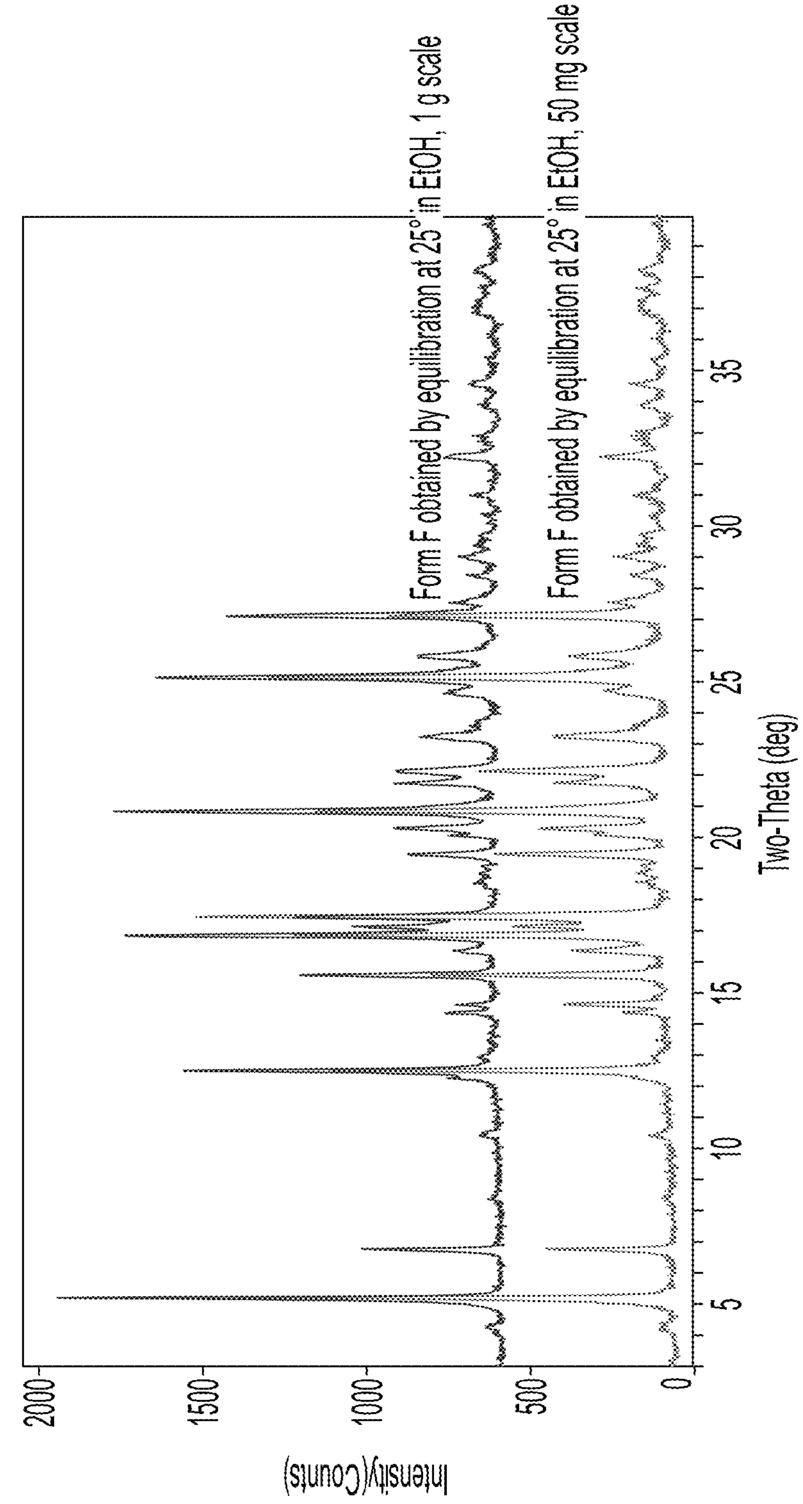
FIG. 29 is an X-ray powder diffraction pattern overlay of 2-(t-butoxy)-4-(3-methyl-3-(5-(methylsulfonyl)isoindolin-2-yl)butyl)phenol mono-fumarate salt, hemi-hydrate, crystal form F. obtained by equilibration of 2-(t-butoxy)-4-(3-methyl-3-(5-(methylsulfonyl)isoindolin-2-yl)butyl)phenol mono-fumarate salt, crystal form A at 25° C. in 1:1 EtOH:water (V/V). The top XRPD is on a 1 g scale of crystal form A, and the bottom XRPD is on a 50 mg scale of form A.

In some aspects, the crystalline form is 2-(t-butoxy)-4-(3-methyl-3-(5-(methylsulfonyl)isoindolin-2-yl)butyl)phenol mono-fumarate salt, hemi-hydrate, crystal form F characterized by an X-ray powder diffraction (XRPD)pattern comprising at least three characteristic 2θ peaks at 5.20, 12.51, 16.84, 20.84, and 25.14° (t 0.2°). In some aspects, the crystalline form is 2-(t-butoxy)-4-(3-methyl-3-(5-(methylsulfonyl)isoindolin-2-yl)butyl)phenol mono-fumarate salt, hemi-hydrate, crystal form F characterized by an X-ray powder diffraction (XRPD) pattern comprising characteristic 2θ peaks at 5.20, 12.51, 16.84, 20.84, and 25.140 (+0.2°). In some aspects, the XRPD of 2-(t-butoxy)-4-(3-methyl-3-(5-(methylsulfonyl)isoindolin-2-yl)butyl)phenol mono-fumarate salt, hemi-hydrate, crystal form F further comprises additional peaks at 15.58, 17.44, and 27.12° (+0.2°). In some aspects, the XRPD of crystal form F further comprises additional peaks at 6.76 and 17.13° (+0.2°). In some aspects, the XRPD of crystal form F further comprises peaks 19.45, 20.30, 21.74, and 22.13° (±0.2°). In some aspects, the XRPD of 2-(t-butoxy)-4-(3-methyl-3-(5-(methylsulfonyl)isoindolin-2-yl)butyl)phenol mono-fumarate salt, hemi-hydrate, crystal form F is substantially as shown in FIG. 29. In some aspects, the XRPD of crystal form F comprises peaks as described in Table 7.

TABLE 7

| XRPD 2-theta values of 2-(t-butoxy)-4-(3-methyl-3-(5-(methylsulfonyl)isoindolin-2-yl)butyl)phenol mono-fumarate salt, hemi-hydrate, crystal form F | |
|---|---|
| Pos. °2θ | Rel. Int. % |
| 4.27 | 3.43 |
| 5.20 | 100 |
| 6.76 | 30.28 |
| 8.43 | 1.83 |
| 10.45 | 3.61 |
| 12.26 | 12.44 |
| 12.51 | 76.81 |
| 12.94 | 4.58 |
| 14.37 | 11.94 |
| 14.63 | 10.12 |
| 15.58 | 47.04 |
| 16.35 | 10.78 |
| 16.84 | 88.36 |
| 17.13 | 31.09 |
| 17.44 | 47.95 |
| 18.56 | 4.33 |
| 19.45 | 21.66 |
| 20.06 | 11.82 |
| 20.30 | 24.49 |
| 20.84 | 88.00 |
| 21.74 | 23.84 |
| 22.13 | 23.37 |
| 23.24 | 16.70 |
| 23.70 | 5.11 |
| 24.59 | 10.68 |
| 25.14 | 80.61 |
| 25.76 | 16.40 |
| 25.85 | 18.73 |
| 27.12 | 60.81 |
| 27.54 | 11.19 |
| 28.41 | 6.29 |
| 29.01 | 8.27 |
| 29.49 | 3.46 |
| 30.98 | 5.70 |
| 32.22 | 12.29 |
| 32.89 | 3.57 |
| 33.88 | 2.69 |
| 34.58 | 5.60 |
| 36.98 | 4.28 |
| 38.22 | 4.47 |

Figure 30:
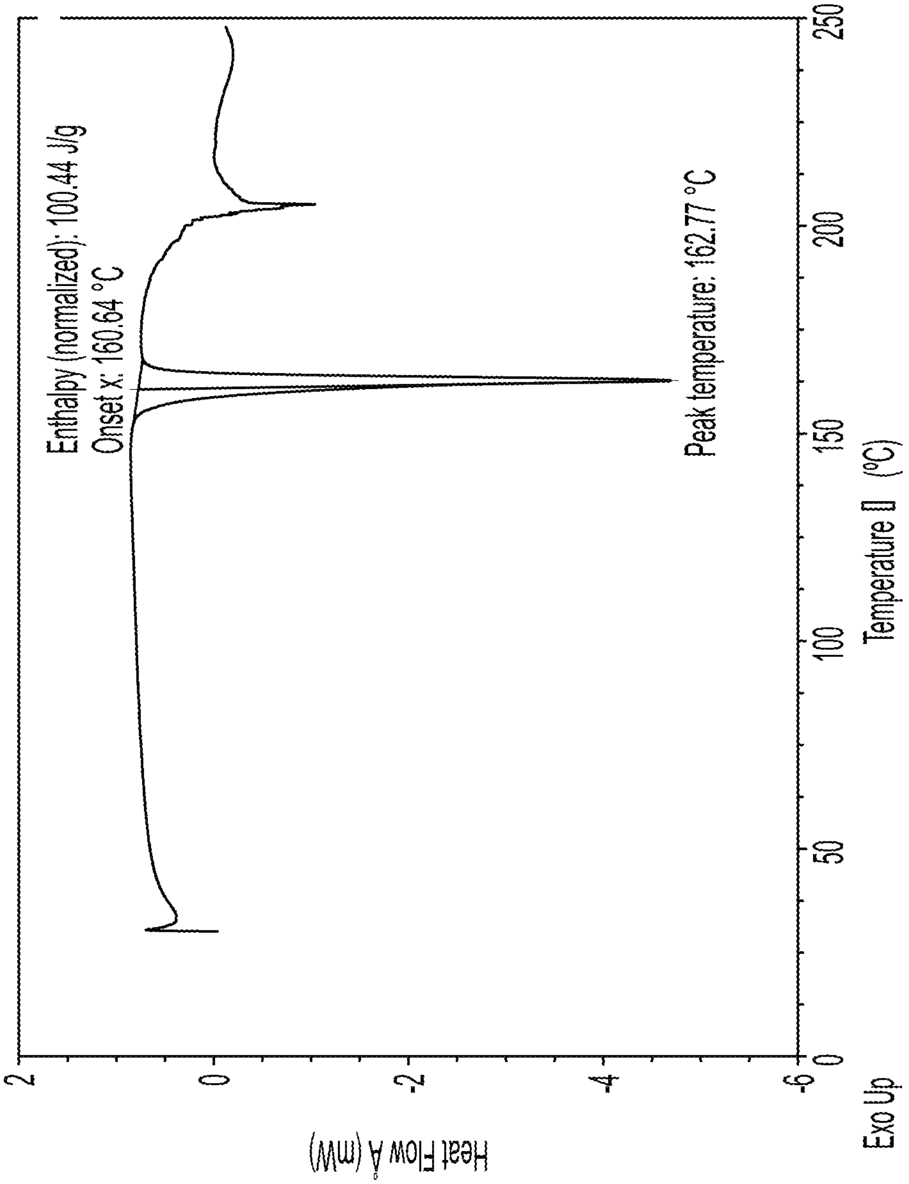
FIG. 30 is a differential scanning calorimetry (DSC) curve of 2-(t-butoxy)-4-(3-methyl-3-(5-(methylsulfonyl)isoindolin-2-yl)butyl)phenol mono-fumarate salt, hemi-hydrate, crystal form F.

In some aspects, 2-(t-butoxy)-4-(3-methyl-3-(5-(methylsulfonyl)isoindolin-2-yl)butyl)phenol mono-fumarate salt, hemi-hydrate, crystal form F is characterized by a differential scanning calorimetry (DSC) curve that comprises. a dehydration onset of about 17.4° C. and an enthalpy of about 13 J/g, followed by a melting peak at T onset of about 160.6° C. with an enthalpy of about 100.4 J/g. In some aspects, the DSC of crystal form F is as shown in FIG. 30.

Figure 31:
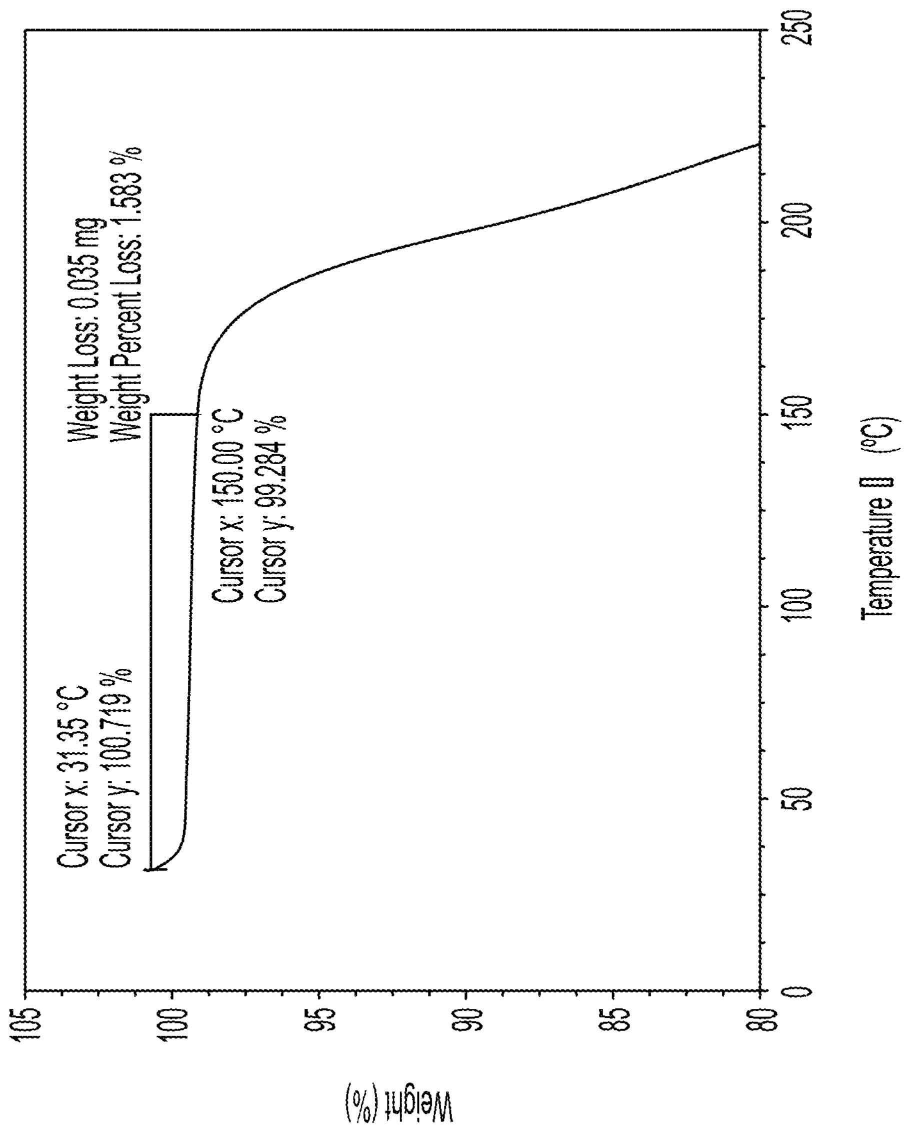
FIG. 31 is a thermogravimetric analysis (TGA) of 2-(t-butoxy)-4-(3-methyl-3-(5-(methylsulfonyl)isoindolin-2-yl)butyl)phenol mono-fumarate salt, hemi-hydrate, crystal form F.

In some aspects, 2-(t-butoxy)-4-(3-methyl-3-(5-(methylsulfonyl)isoindolin-2-yl)butyl)phenol mono-fumarate salt, hemi-hydrate, crystal form F shows a mass loss of about 1.6% at about 150.0° C. In some aspects, the TGA of crystal form F is substantially as shown in FIG. 31.

In some aspects, 2-(t-butoxy)-4-(3-methyl-3-(5-(methylsulfonyl)isoindolin-2-yl)butyl)phenol mono-fumarate salt, hemi-hydrate, crystal form F is described by an XRPD as described in any aspect of paragraphs [0137]-[0138] in combination with any aspect of DSC, as described in paragraph [0139], and/or TGA as described in paragraph [0140].

In some aspects, 2-(t-butoxy)-4-(3-methyl-3-(5-(methylsulfonyl)isoindolin-2-yl)butyl)phenol mono-fumarate salt, hemi-hydrate, crystal form F according to any aspect described herein has a polymorph purity of at least 50%. In some aspects, crystal form F has a polymorph purity of at least 75%. In some aspects, crystal form F has a polymorph purity of at least 80%. In some aspects, crystal form F has a polymorph purity of at least 85%. In some aspects, crystal form F has a polymorph purity of at least 90%. In some aspects, crystal form F has a polymorph purity of at least 95%. In some aspects, crystal form F has a polymorph purity of at least 96%. In some aspects, crystal form F has a polymorph purity of at least 97%. In some aspects, crystal form F has a polymorph purity of at least 98%. In some aspects, crystal form F has a polymorph purity of at least 99%. In some aspects, crystal form F has a polymorph purity of about 95%. In some aspects, crystal form F has a polymorph purity of about 96%. In some aspects, crystal form F has a polymorph purity of about 97%. In some aspects, crystal form F has a polymorph purity of about 98%. In some aspects, crystal form F has a polymorph purity of about 99%.

In some aspects, 2-(t-butoxy)-4-(3-methyl-3-(5-(methylsulfonyl)isoindolin-2-yl)butyl)phenol mono-fumarate salt, hemi-hydrate, crystal form F according to any aspect described herein has a chemical purity of at least 50 A %. In some aspects, crystal form F has a chemical purity of at least 75 A %. In some aspects, crystal form F has a chemical purity of at least 80 A %. In some aspects, crystal form F has a chemical purity of at least 85 A %. In some aspects, crystal form F has a chemical purity of at least 90 A %. In some aspects, crystal form F has a chemical purity of at least 91 A %. In some aspects, crystal form F has a chemical purity of at least 92 A %. In some aspects, crystal form F has a chemical purity of at least 93 A %. In some aspects, crystal form F has a chemical purity of at least 94 A %. In some aspects, crystal form F has a chemical purity of at least 95 A %. In some aspects, crystal form F has a chemical purity of at least 96 A %. In some aspects, crystal form F has a chemical purity of at least 97 A %. In some aspects, crystal form F has a chemical purity of at least 98 A %. In some aspects, crystal form F has a chemical purity of at least 99 A %. In some aspects, crystal form F has a chemical purity of about 90 A %. In some aspects, crystal form F has a chemical purity of about 91 A %. In some aspects, crystal form F has a chemical purity of about 92 A %. In some aspects, crystal form F has a chemical purity of about 93 A %. In some aspects, crystal form F has a chemical purity of about 94 A %. In some aspects, crystal form F has a chemical purity of about 95 A %. In some aspects, crystal form F has a chemical purity of about 96 A %. In some aspects, crystal form F has a chemical purity of about 97 A %. In some aspects, crystal form F has a chemical purity of about 98 A %. In some aspects, crystal form F has a chemical purity of about 99 A %.

Figure 32:
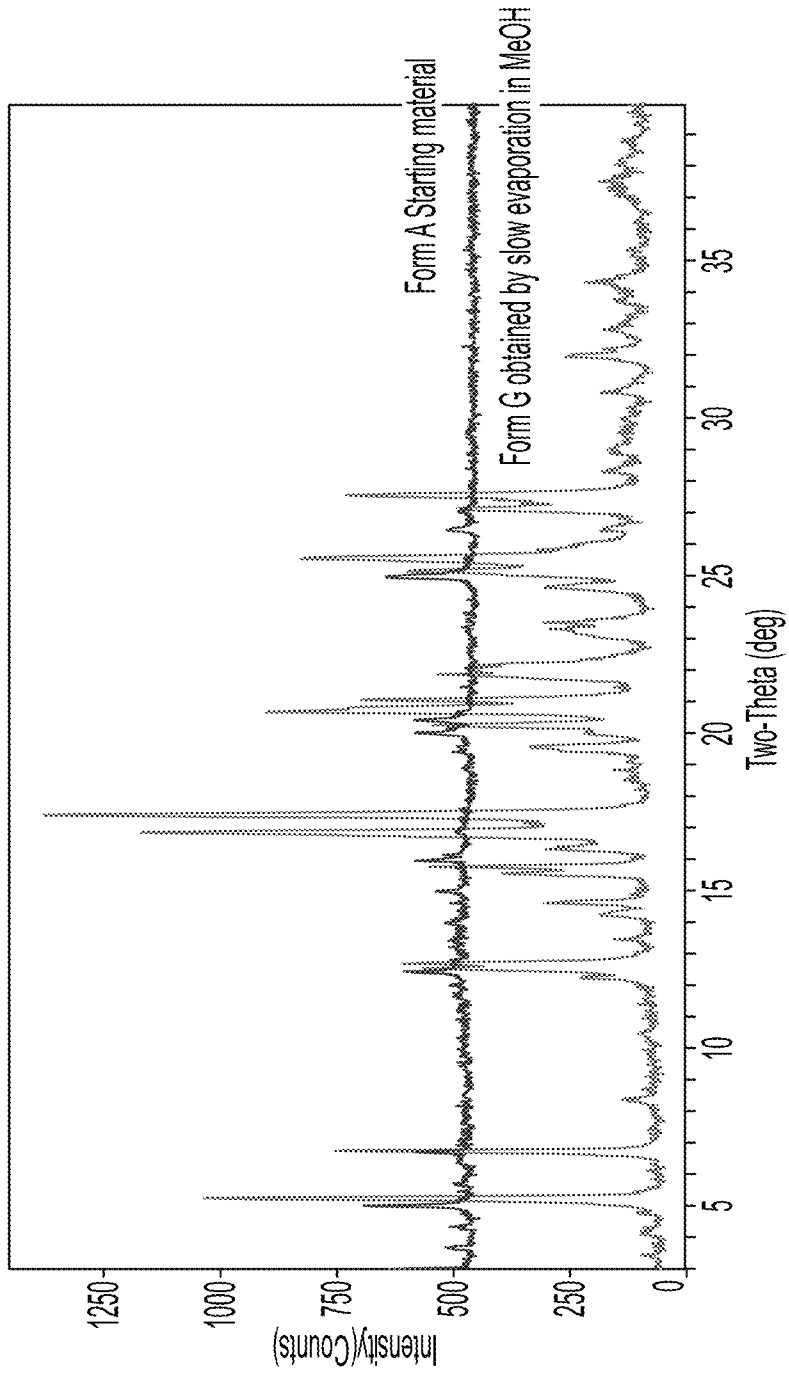
FIG. 32 is an X-ray powder diffraction pattern overlay of 2-(t-butoxy)-4-(3-methyl-3-(5-(methylsulfonyl)isoindolin-2-yl)butyl)phenol mono-fumarate salt, methanol solvate, crystal form G, obtained by slow evaporation of 2-(t-butoxy)-4-(3-methyl-3-(5-(methylsulfonyl)isoindolin-2-yl)butyl)phenol mono-fumarate salt, crystal form A in methanol (bottom XRPD); overlayed with 2-(t-butoxy)-4-(3-methyl-3-(5-(methylsulfonyl)isoindolin-2-yl)butyl)phenol mono-fumarate salt, crystal form A (top XRPD).

In some aspects, the crystalline form is crystal salt 2-(t-butoxy)-4-(3-methyl-3-(5-(methylsulfonyl)isoindolin-2-yl) butyl)phenol mono-fumarate salt, methanol solvate, crystal form G characterized by an X-ray powder diffraction (XRPD) pattern as shown in FIG. 32

In some aspects, 2-(t-butoxy)-4-(3-methyl-3-(5-(methylsulfonyl)isoindolin-2-yl)butyl)phenol mono-fumarate salt, methanol solvate, crystal form G according to any aspect described herein has a polymorph purity of at least 50%. In some aspects, crystal form G has a polymorph purity of at least 75%. In some aspects, crystal form G has a polymorph purity of at least 80%. In some aspects, crystal form G has a polymorph purity of at least 85%. In some aspects, crystal form G has a polymorph purity of at least 90%. In some aspects, crystal form G has a polymorph purity of at least 95%. In some aspects, crystal form G has a polymorph purity of at least 96%. In some aspects, crystal form G has a polymorph purity of at least 97%. In some aspects, crystal form G has a polymorph purity of at least 98 A %. In some aspects, crystal form G has a polymorph purity of at least 99%. In some aspects, crystal form G has a polymorph purity of about 95%. In some aspects, crystal form G has a polymorph purity of about 96%. In some aspects, crystal form G has a polymorph purity of about 97%. In some aspects, crystal form G has a polymorph purity of about 98%. In some aspects, crystal form G has a polymorph purity of about 99%.

In some aspects, 2-(t-butoxy)-4-(3-methyl-3-(5-(methylsulfonyl)isoindolin-2-yl)butyl)phenol mono-fumarate salt, methanol solvate, crystal form G according to any aspect described herein has a chemical purity of at least 50 A %. In some aspects, crystal form G has a chemical purity of at least 75 A %. In some aspects, crystal form G has a chemical purity of at least 80 A %. In some aspects, crystal form G has a chemical purity of at least 85 A %. In some aspects, crystal form G has a chemical purity of at least 90 A %. In some aspects, crystal form G has a chemical purity of at least 91 A %. In some aspects, crystal form G has a chemical purity of at least 92 A %. In some aspects, crystal form G has a chemical purity of at least 93 A %. In some aspects, crystal form G has a chemical purity of at least 94 A %. In some aspects, crystal form G has a chemical purity of at least 95 A %. In some aspects, crystal form G has a chemical purity of at least 96 A %. In some aspects, crystal form G has a chemical purity of at least 97 A %. In some aspects, crystal form G has a chemical purity of at least 98 A %. In some aspects, crystal form G has a chemical purity of at least 99 A %. In some aspects, crystal form G has a chemical purity of about 90 A %. In some aspects, crystal form G has a chemical purity of about 91 A %. In some aspects, crystal form G has a chemical purity of about 92 A %. In some aspects, crystal form G has a chemical purity of about 93 A %. In some aspects, crystal form G has a chemical purity of about 94 A %. In some aspects, crystal form G has a chemical purity of about 95 A %. In some aspects, crystal form G has a chemical purity of about 96 A %. In some aspects, crystal form G has a chemical purity of about 97 A %. In some aspects, crystal form G has a chemical purity of about 98 A %. In some aspects, crystal form G has a chemical purity of about 99 A %.

Several attributes are typically considered in selecting the ideal polymorph including intrinsic dissolution, solubility in biorelevant media, bioavailability, solid-state stability (physical and chemical), solution stability, hygroscopicity, downstream processibility (flowability, compressibility), morphology and synthetic accessibility. Different polymorphs can have different stabilities under different physical conditions.

Figure 33:
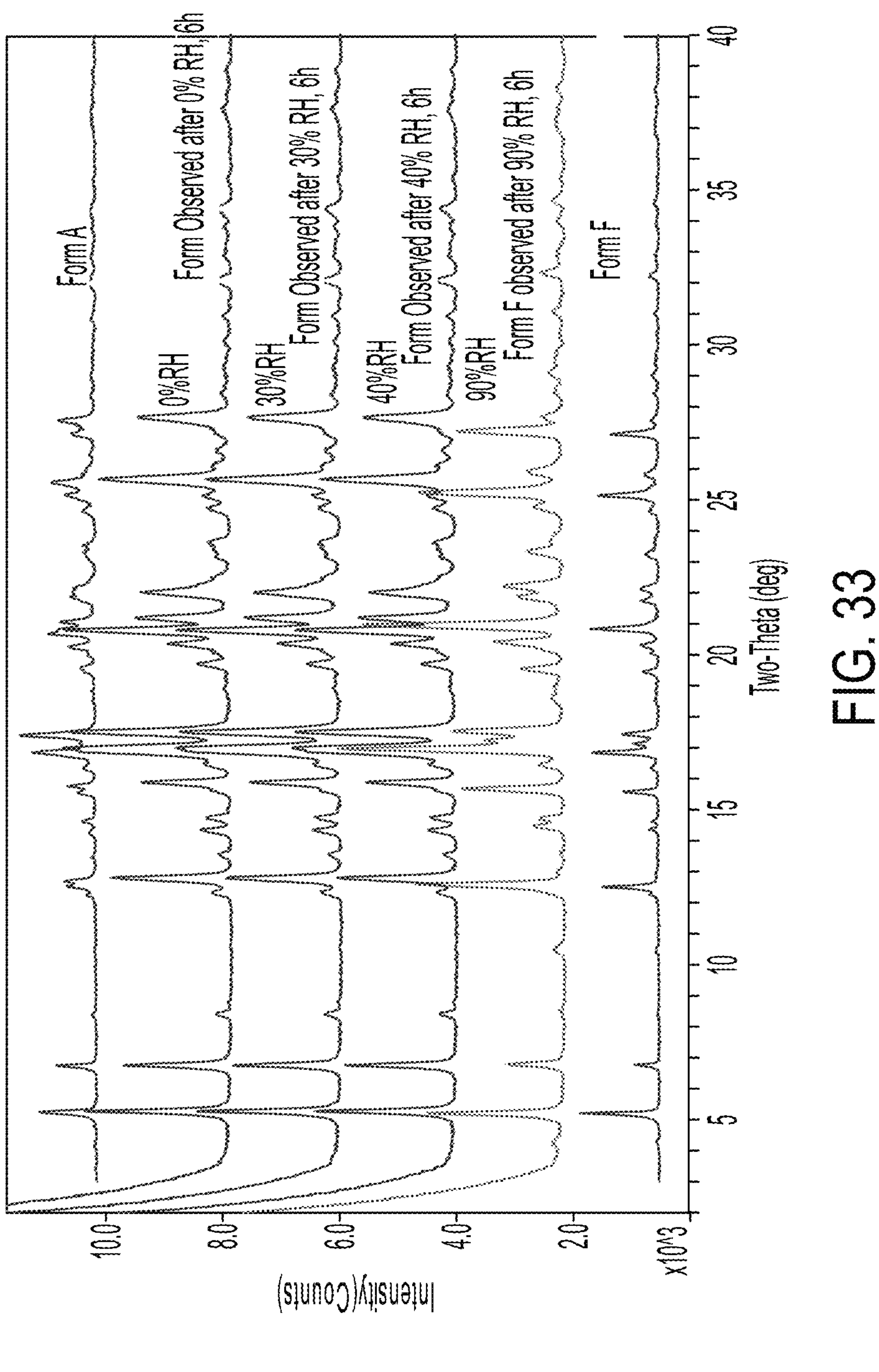
FIG. 33 is an X-ray powder diffraction pattern overlay of samples of 2-(t-butoxy)-4-(3-methyl-3-(5-(methylsulfonyl)isoindolin-2-yl)butyl)phenol mono-fumarate salt, hemi-hydrate, crystal form F to humidity control from 90% relative humidity to 0% relative humidity. The top XRPD is 2-(t-butoxy)-4-(3-methyl-3-(5-(methylsulfonyl)isoindolin-2-yl)butyl)phenol mono-fumarate salt, crystal form A (reference). The second from the top XRPD is the result to 0% relative humidity for 6 hours. The third from the top XRPD is the result of exposure to 30% relative humidity for 6 hours. The third from the bottom XRPD is the result of exposure to 40% relative humidity for 6 hours. The second from the bottom XRPD is the result of exposure to 90% relative humidity for 6 hours. The bottom XRPD is form F.
Figure 34:
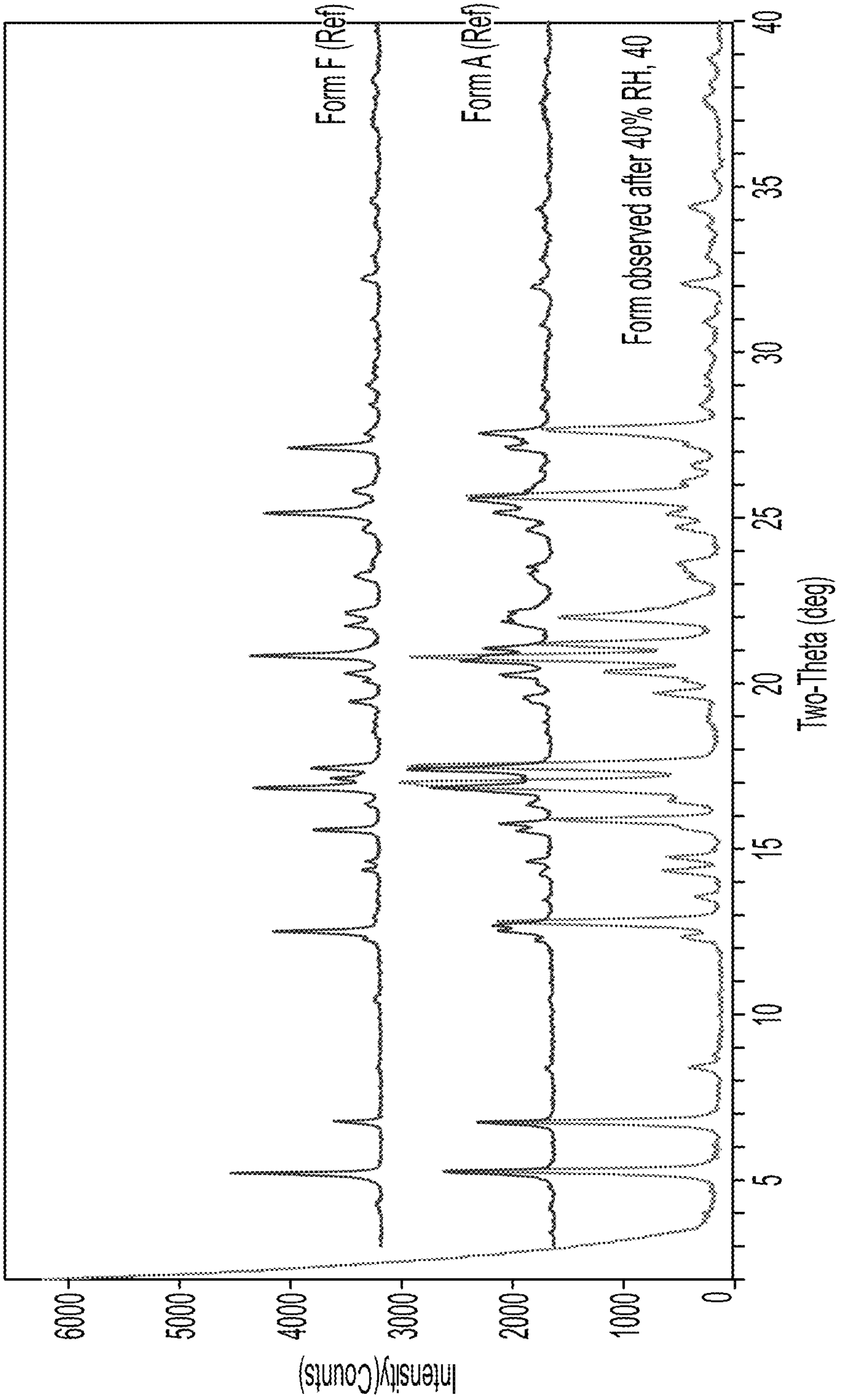
FIG. 34 is an X-ray powder diffraction pattern overlay of 2-(t-butoxy)-4-(3-methyl-3-(5-(methylsulfonyl)isoindolin-2-yl)butyl)phenol mono-fumarate salt, hemi-hydrate, crystal form F after humidity control at 0% relative humidity for 40 hours (bottom XRPD), overlayed with XRPDS of crystal form A (middle) and crystal form F (top).
Figure 35:
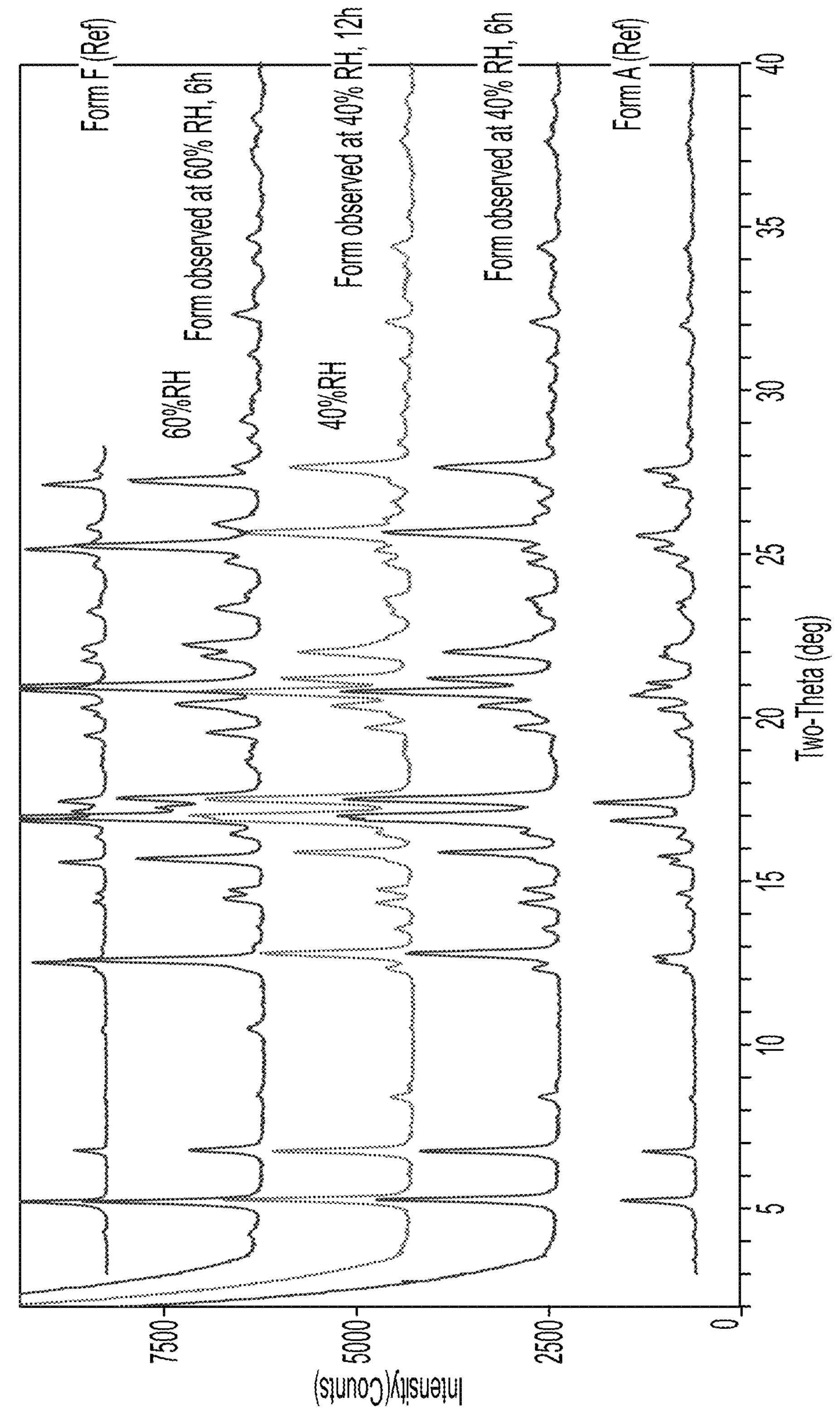
FIG. 35 is an X-ray powder diffraction pattern overlay of 2-(t-butoxy)-4-(3-methyl-3-(5-(methylsulfonyl)isoindolin-2-yl)butyl)phenol mono-fumarate salt, hemi-hydrate, crystal form F after humidity control from 40% relative humidity to 60% relative humidity. The top XRPD is 2-(t-butoxy)-4-(3-methyl-3-(5-(methylsulfonyl)isoindolin-2-yl)butyl)phenol mono-fumarate salt, hemi-hydrate, crystal form F (reference). The second from the top XRPD is the result of exposure of crystal form F to 60% relative humidity for 6 hours. The third from the top XRPD is the result of exposure of crystal form F to 40% relative humidity for 12 hours. The second from the bottom XRPD is the result of exposure of crystal form F to 40% relative humidity for 6 hours. The bottom XRPD is the form A.
Figure 36:
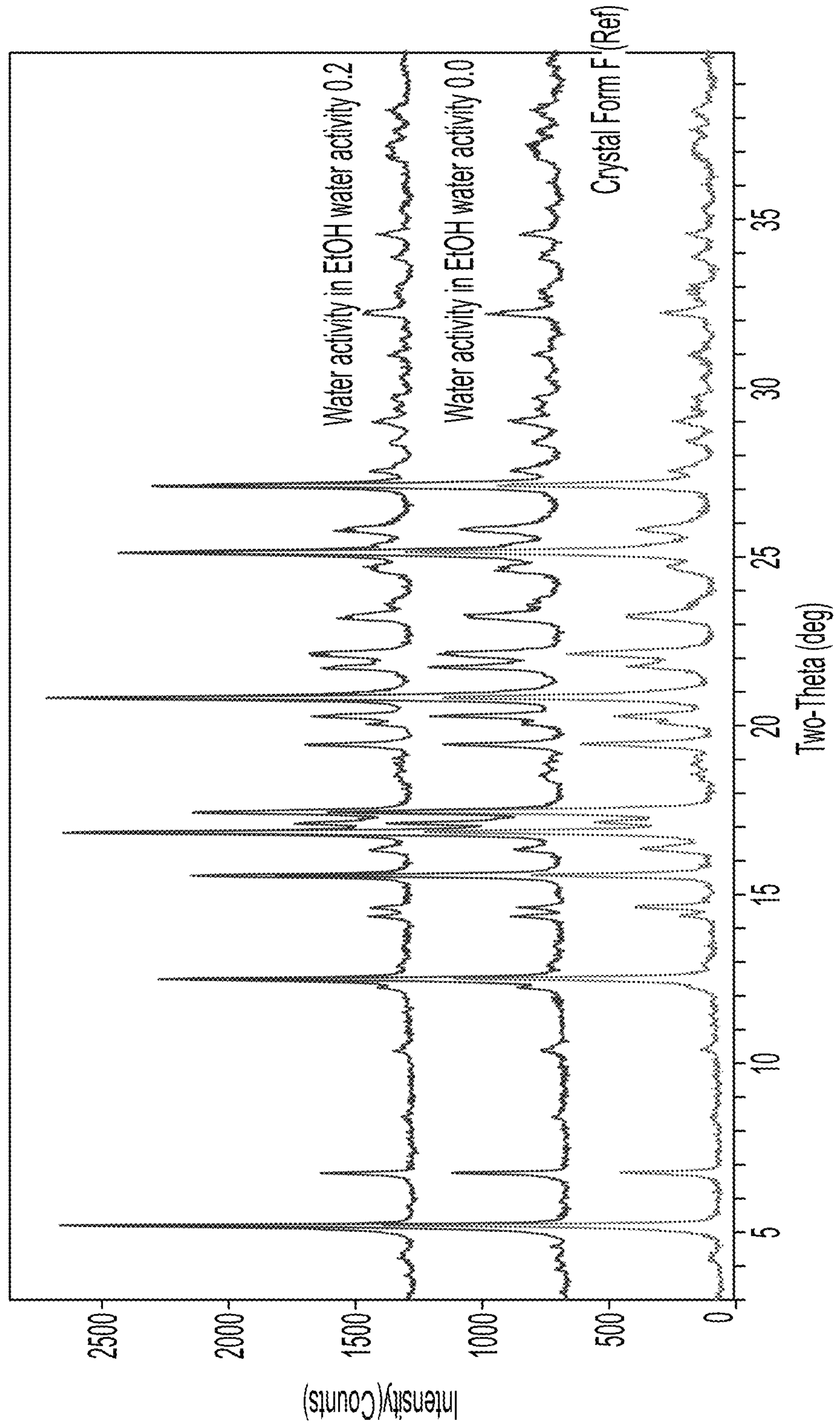
FIG. 36 is an XRPD overlay of samples after equilibration of 2-(t-butoxy)-4-(3-methyl-3-(5-(methylsulfonyl)isoindolin-2-yl)butyl)phenol mono-fumarate salt, crystal form A in different water activities in ethanol. The top XRPD is the result of equilibration at 0.2 water activity (crystal form F observed). The middle XRPD is the result of equilibration at 0.0 water activity (crystal form F observed). The bottom XRPD is crystal form F (reference).
Figure 37:
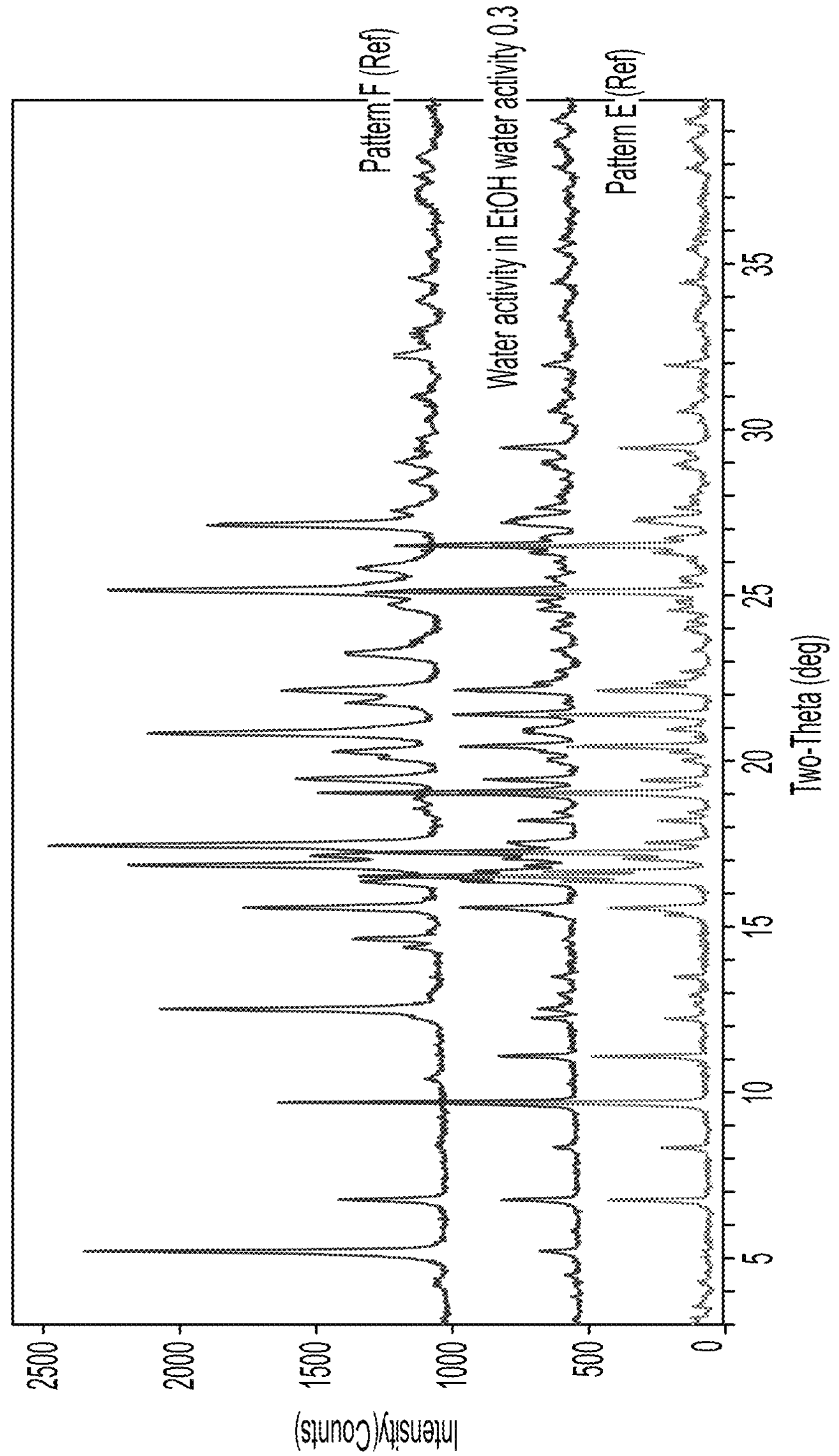
FIG. 37 is an XRPD overlay of samples after equilibration of 2-(t-butoxy)-4-(3-methyl-3-(5-(methylsulfonyl)isoindolin-2-yl)butyl)phenol mono-fumarate salt, crystal form A in 0.3 water activity in ethanol (middle XRPD, a mixture of form E and form F observed), overlayed with crystal form F (top, reference) and crystal form E (bottom, reference).
Figure 38:
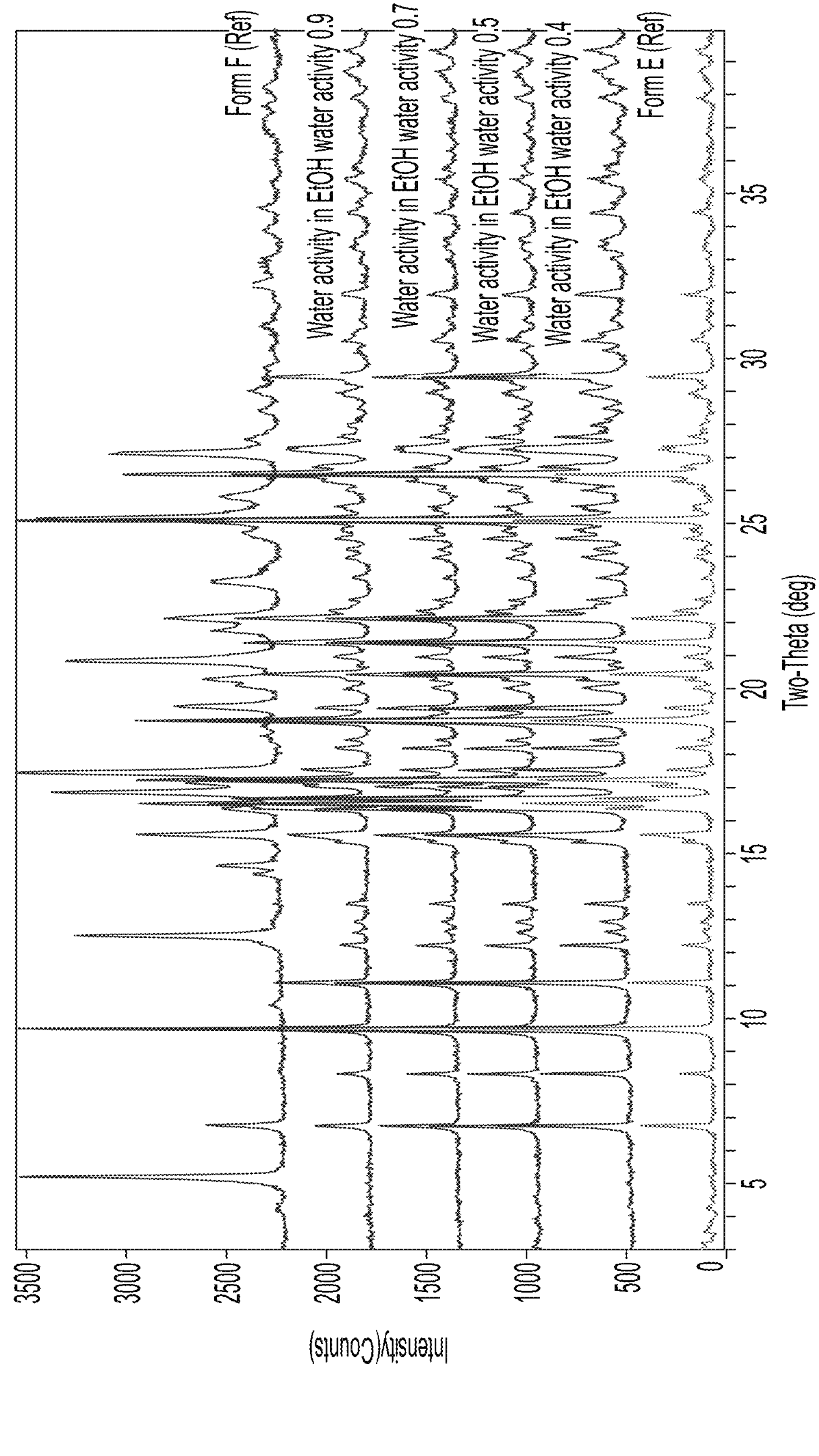
FIG. 38 is an XRPD overlay of samples after equilibration of 2-(t-butoxy)-4-(3-methyl-3-(5-(methylsulfonyl)isoindolin-2-yl)butyl)phenol mono-fumarate salt, crystal form A in different water activities in ethanol. The top XRPD is crystal form F (reference). The second from the top XRPD is the result of equilibration at 0.9 water activity (crystal form E observed). The third from the top XRPD is the result of equilibration at 0.7 water activity (crystal form E observed). The third from the bottom XRPD is the result of equilibration at 0.5 water activity (crystal form E observed). The second from the bottom XRPD is the result of equilibration at 0.4 water activity (crystal form E observed). The bottom XRPD is crystal form E (reference).

Crystal form A was initially developed; however, crystal form A was found to have (1) sub-optimal flowability/processability, arising from its sticky needle-like (acicular) crystals, (2) propensity to undergo oxidative degradation in oral solid dosage forms, (3) reversable formation to its isostructural hemihydrate (form F) upon exposure to RH>40%, (Example 8 and FIGS. 33-35) (4) disproportionation to form E in water or solutions with a water activity ($a_w$)>0.4, (Example 10 and FIGS. 36-38) and (5) inferior impurity rejection compared to form E (See preparation of form A (Example 1) vs. preparation of form E (Example 2, Method K)). Additionally, the relative stability of Forms A, E, and F was assessed by a competitive slurry study that showed: (1) at $a_w$>0.4, only form E, which presented a cubic morphology, was observed (by PLM, XPRD); (2) at $a_w$<0.3, only form A was observed (See Example 11). Form E was also shown to be stable in the solid state (Example 9). Thus, form E was assessed to be the most thermodynamically stable polymorph in solutions such as aqueous alcohol mixtures used to isolate the API.

Pharmaceutical Compositions

In some aspects, the present disclosure is directed to a pharmaceutical composition comprising one or more crystalline forms of 2-(t-butoxy)-4-(3-methyl-3-(5-(methylsulfonyl)isoindolin-2-yl)butyl)phenol fumarate salt, and at least one pharmaceutically acceptable excipient. In particular, the disclosure provides a pharmaceutical composition comprising a therapeutically effective amount of one or more crystalline forms of 2-(t-butoxy)-4-(3-methyl-3-(5-(methylsulfonyl)isoindolin-2-yl)butyl)phenol fumarate salt, and at least one pharmaceutically acceptable excipient. In some aspects, the salt is a mono fumarate salt. In some aspects, the salt is a hemi-fumarate salt.

While it is possible that a compound as described in any embodiment herein, may be administered as the bulk substance, it is preferable to present the compound in a pharmaceutical formulation, e.g., wherein the active agent is in an admixture with a pharmaceutically acceptable excipient selected with regard to the intended route of administration and standard pharmaceutical practice.

In one aspect, the pharmaceutical composition comprises a crystal form selected from selected from the group consisting of: 2-(t-butoxy)-4-(3-methyl-3-(5-(methylsulfonyl)isoindolin-2-yl)butyl)phenol hemi-fumarate dihydrate salt crystal form E, 2-(t-butoxy)-4-(3-methyl-3-(5-(methylsulfonyl)isoindolin-2-yl)butyl)phenol mono-fumarate salt crystal form A, 2-(t-butoxy)-4-(3-methyl-3-(5-(methylsulfonyl)isoindolin-2-yl)butyl)phenol mono-fumarate salt, acetone solvate crystal form B, 2-(t-butoxy)-4-(3-methyl-3-(5-(methylsulfonyl)isoindolin-2-yl)butyl)phenol mono-fumarate salt, acetonitrile solvate crystal form C, 2-(t-butoxy)-4-(3-methyl-3-(5-(methylsulfonyl)isoindolin-2-yl)butyl)phenol mono-fumarate salt crystal form D, 2-(t-butoxy)-4-(3-methyl-3-(5-(methylsulfonyl)isoindolin-2-yl)butyl)phenol mono-fumarate salt, hemi-hydrate crystal form F, and 2-(t-butoxy)-4-(3-methyl-3-(5-(methylsulfonyl)isoindolin-2-yl)butyl)phenol mono-fumarate salt, methanol solvate, crystal form G; as described generally above, and at least one pharmaceutically acceptable excipient.

In one aspect, the pharmaceutical composition comprises 2-(t-butoxy)-4-(3-methyl-3-(5-(methylsulfonyl)isoindolin-2-yl)butyl)phenol hemi-fumarate dihydrate salt crystal form E according to any aspect described herein and a pharmaceutically acceptable excipient.

In one aspect, the pharmaceutical composition comprises 2-(t-butoxy)-4-(3-methyl-3-(5-(methylsulfonyl)isoindolin-2-yl)butyl)phenol mono-fumarate salt crystal form A according to any aspect described herein and a pharmaceutically acceptable excipient.

In one aspect, the pharmaceutical composition comprises: 2-(t-butoxy)-4-(3-methyl-3-(5-(methylsulfonyl)isoindolin-2-yl)butyl)phenol mono-fumarate salt, acetone solvate crystal form B according to any aspect described herein and a pharmaceutically acceptable excipient.

In one aspect, the pharmaceutical composition comprises 2-(t-butoxy)-4-(3-methyl-3-(5-(methylsulfonyl)isoindolin-2-yl)butyl)phenol mono-fumarate salt, acetonitrile solvate crystal form C according to any aspect described herein and a pharmaceutically acceptable excipient.

In one aspect, the pharmaceutical composition 2-(t-butoxy)-4-(3-methyl-3-(5-(methylsulfonyl)isoindolin-2-yl)butyl)phenol mono-fumarate salt crystal form D according to any aspect described herein and a pharmaceutically acceptable excipient.

In one aspect, the pharmaceutical composition 2-(t-butoxy)-4-(3-methyl-3-(5-(methylsulfonyl)isoindolin-2-yl) butyl)phenol mono-fumarate salt, hemi-hydrate crystal form F according to any aspect described herein and a pharmaceutically acceptable excipient.

In one aspect, the pharmaceutical composition 22-(t-butoxy)-4-(3-methyl-3-(5-(methylsulfonyl)isoindolin-2-yl) butyl)phenol mono-fumarate salt, methanol solvate, crystal form G according to any aspect described herein and a pharmaceutically acceptable excipient.

For the pharmaceutical compositions and methods of the disclosure, a crystalline forms of 2-(t-butoxy)-4-(3-methyl-3-(5-(methylsulfonyl)isoindolin-2-yl)butyl)phenol fumarate salt according to any aspect described herein, may be used in combination with other therapies and/or active agents.

In some embodiments, the compound according to any embodiment described herein, can be combined with one or more of an anti-vascular endothelial growth factor (VEGF) treatment, vessel occlusion, and glaucoma treatments. In some embodiments, the compound is combined with a VEGF inhibitor selected from brolucizumab (BEOVU®; Novartis), aflibercept (Eylea@; Regeron), ranibizumab (Lucentis®, Genentech), bevacizumab (Avastin®, Genentech), and pegaptanib (Macugen®, Bausch+Lomb). In some embodiments, the compound is combined with a treatment for vessel occlusion selected from verteporfin (Visudyne®, Bausch+Lomb) and laser treatment. In some embodiments, the compound is combined with a complement cascade therapeutic selected from POT-4 (Compstatin®, Alcon), ARC 1905 (Ophthotech), Eculizumab (Soliris®, Alexion Pharmaceuticals), FCFD4514S (Genentech), TA106 (Taligen Therapeutics and Alexion Pharmaceuticals), JSM-7717 (EvaluatePharma), CR2-fH, and C1INH (ViroPharma). In some embodiments the compound is combined with a treatment for glaucoma selected from brimonidine (Alpagan®; Allergan), apraclonidine (Iopidine®; Novartis), netarsudil (Rhopressa®, Aerie Pharmaceuticals). In some embodiments, the compound is combined with a treatment for glaucoma selected from beta blockers, carbonic anhydrase inhibitors, cholinergics, and prostaglandins.

In some embodiments, the compound according to any embodiment described herein, can be combined with one or more of a cholinesterase inhibitor, an N-methyl-D-aspartate (NMDA) glutamate receptor antagonist, a beta-amyloid specific antibody, a beta-secretase 1 (BACE1, beta-site amyloid precursor protein cleaving enzyme 1) inhibitor, a tumor necrosis factor alpha (TNF alpha) modulator, an intravenous immunoglobulin (IVIG), or a prion protein antagonist. In some embodiments the compound is combined with a cholinesterase inhibitor selected from tacrine (COGNEX®; Sciele), donepezil (ARICEPT®; Pfizer), rivastigmine (EXELON®; Novartis), or galantamine (RAZADYNE®; Ortho-McNeil-Janssen). In some embodiments, the compound is combined with a TNFalpha modulator that is perispinal etanercept (ENBREL®, Amgen/Pfizer). In some embodiments, the compound is combined with a beta-amyloid specific antibody selected from bapineuzumab (Pfizer), solanezumab (Lilly), PF-04360365 (Pfizer), GSK933776(GlaxoSmithKline), Gammagard (Baxter) or Octagam (Octapharma). In some embodiments, the compound is combined with an NMDA receptor antagonist that is memantine (NAMENDA®; Forest). In some embodiments, the BACE1 inhibitor is MK-8931 (Merck). In some embodiments, the compound is combined with IVIG as described in Magga et al., J Neuroinflam 2010, 7:90, Human intravenous immunoglobulin provides protection against Ab toxicity by multiple mechanisms in a mouse model of Alzheimer's disease, and Whaley et al., 2011, Human Vaccines 7:3, 349-356, Emerging antibody products and *Nicotiana* manufacturing; each of which is incorporated herein by reference. In some embodiments, the compound is combined with a prion protein antagonist as disclosed in Strittmatter et al., US 2010/0291090, which is incorporated herein by reference.

Accordingly, the disclosure provides, in a further aspect, a pharmaceutical composition comprising at least one compound according to any embodiment described herein, or pharmaceutically acceptable derivative thereof; a second active agent; and optionally, a pharmaceutically acceptable excipient.

When combined in the same formulation it will be appreciated that the two or more compounds must be stable and compatible with each other and the other components of the formulation. When formulated separately they may be provided in any convenient formulation, in such manner as are known for such compounds in the art.

Preservatives, stabilizers, dyes and flavoring agents may be provided in any pharmaceutical composition described herein. Examples of preservatives include sodium benzoate, ascorbic acid and esters of p-hydroxybenzoic acid. Antioxidants and suspending agents may be also used.

With respect to combinations including biologics such as monoclonal antibodies or fragments, suitable excipients will be employed to prevent aggregation and stabilize the antibody or fragment in solution with low endotoxin, generally for parenteral administration, for example, intravenous, administration. For example, see Formulation and Delivery Issues for Monoclonal Antibody Therapeutics, Daugherty et al., in Current Trends in Monoclonal Antibody Development and Manufacturing, Part 4, 2010, Springer, New York pp 103-129.

The compounds according to any embodiment described herein, may be milled using known milling procedures such as wet milling to obtain a particle size appropriate for tablet formation and for other formulation types. Finely divided (nanoparticulate) preparations of the compounds may be prepared by processes known in the art, for example see WO 02/00196 (SmithKline Beecham).

Compounds according to any embodiment described herein can be formulated for any route of administration.

The pharmaceutical compositions can be prepared in a manner well known in the pharmaceutical art, and can be administered by a variety of routes, depending upon whether local or systemic treatment is desired and upon the area to be treated.

Routes of Administration and Unit Dosage Forms

The routes for administration (delivery) include, but are not limited to, one or more of: local ocular (e.g. subconjunctival, intravitreal, retrobulbar, intracameral), oral (e.g., as a tablet, capsule, or as an ingestible solution), topical, mucosal (e.g., as a nasal spray or aerosol for inhalation), parenteral (e.g., by an injectable form), gastrointestinal, intraspinal, intraperitoneal, intramuscular, intravenous, intracerebroventricular, or other depot administration etc.

Therefore, the pharmaceutical compositions according to any embodiment described herein, include those in a form especially formulated for the mode of administration. In certain embodiments, the pharmaceutical compositions of the disclosure are formulated in a form that is suitable for oral delivery. In some embodiments, the compound is an orally bioavailable compound, suitable for oral delivery. In other embodiments, the pharmaceutical compositions of the disclosure are formulated in a form that is suitable for parenteral delivery. In other embodiments, the pharmaceutical compositions of the disclosure are formulated in a form that is suitable for ocular delivery.

The compounds according to any embodiment described herein, may be formulated for administration in any convenient way for use in human or veterinary medicine and the disclosure therefore includes within its scope pharmaceutical compositions comprising a compound according to any embodiment described herein, adapted for use in human or veterinary medicine. Such pharmaceutical compositions may be presented for use in a conventional manner with the aid of one or more suitable excipients. Acceptable excipients for therapeutic use are well-known in the pharmaceutical art, and are described, for example, in Remington's Pharmaceutical Sciences, Mack Publishing Co. (A. R. Gennaro edit. 1985). The choice of pharmaceutical excipient can be selected with regard to the intended route of administration and standard pharmaceutical practice. The pharmaceutical compositions may comprise as, in addition to, the excipient any suitable binder(s), lubricant(s), suspending agent(s), coating agent(s), and/or solubilizing agent(s).

There may be different pharmaceutical composition/formulation requirements depending on the different delivery systems. It is to be understood that not all of the compounds need to be administered by the same route. Likewise, if the pharmaceutical composition comprises more than one active component, then those components may be administered by different routes. By way of example, the pharmaceutical composition of the disclosure may be formulated to be delivered using for oral delivery, for example via a tablet or capsule. The pharmaceutical composition of the disclosure may be formulated to be delivered via a local ocular route, for example, as a subconjunctival ocular injection or intravitreal ocular injection, in which the pharmaceutical composition is formulated for delivery for injection into the eye.

The combination of a compound according to any embodiment described herein, and an antibody or antibody fragment molecule can be formulated and administered by any of a number of routes and are administered at a concentration that is therapeutically effective in the indication or for the purpose sought. To accomplish this goal, the antibodies may be formulated using a variety of acceptable excipients known in the art. Typically, the antibodies are administered by injection, for example, intravenous injection. Methods to accomplish this administration are known to those of ordinary skill in the art. For example, Gokarn et al., 2008, J Pharm Sci 97(8):3051-3066, incorporated herein by reference, describe various high concentration antibody self-buffered formulations. For example, monoclonal antibodies in self-buffered formulation at e.g., 50 mg/mL mAb in 5.25% sorbitol, pH 5.0; or 60 mg/mL mAb in 5% sorbitol, 0.01% polysorbate 20, pH 5.2; or conventional buffered formulations, for example, 50 mg/mL mAb1 in 5.25% sorbitol, 25 or 50 mM acetate, glutamate or succinate, at pH 5.0; or 60 mg/mL in 10 mM acetate or glutamate, 5.25% sorbitol, 0.01% polysorbate 20, pH 5.2; other lower concentration formulations can be employed as known in the art.

Because some compounds of the disclosure cross the blood brain barrier, they can be administered by a variety of methods including for example systemic (e.g., by iv, SC, oral, mucosal, transdermal route) or localized methods (e.g., intracranially).

Where the compound according to any embodiment described herein, is to be administered directly to the eye, the compound may be administered topically to the eye or eye lid, for example, using drops, an ointment, a cream, a gel, a suspension, etc. The compound(s) may be formulated with excipients such as methylcellulose, hydroxypropyl methylcellulose, hydroxypropyl cellulose, polyvinyl pyrrolidine, neutral poly(meth)acrylate esters, and other viscosity-enhancing agents. The compounds(s) may be injected into the eye, for example, injection under the conjunctiva or tenon capsule, intravitreal injection, or retrobulbar injection. The compounds(s) may be administered with a slow-release drug delivery system, such as polymers, matrices, microcapsules, or other delivery systems formulated from, for example, glycolic acid, lactic acid, combinations of glycolic and lactic acid, liposomes, silicone, polyanhydride polyvinyl acetate alone or in combination with polyethylene glycol, etc. The delivery device can be implanted intraocularly, for example, implanted under the conjunctiva, implanted in the wall of the eye, sutured to the sclera, for long-term drug delivery.

Pharmaceutically acceptable excipients and additives for ophthalmic use are known to the person skilled in the art, (carriers, stabilizers, solubilizers, tonicity enhancing agents, buffer substances, preservatives, thickeners, complexing agents and other excipients). Examples of such additives and excipients can be found in U.S. Pat. Nos. 5,891,913, 5,134,124 and 4,906,613. Pharmaceutical compositions of the present invention in some embodiments are prepared, for example by mixing the active agent with the corresponding excipients and/or additives to form corresponding ophthalmic compositions. The compound according to any embodiment described herein can be administered in the form of eye drops, the active agent being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic formulation of the invention.

Where the compound according to any embodiment described herein, is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, compounds according to any embodiment described herein, prepared for oral administration may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). In some embodiments, the aqueous enteric coating layer is a methacrylic acid copolymer.

Where appropriate, the pharmaceutical compositions according to any embodiment described herein, can be administered by inhalation, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For buccal or sublingual administration, the pharmaceutical compositions according to any embodiment described herein, may be administered in the form of tablets or lozenges, which can be formulated in a conventional manner.

Where the pharmaceutical composition according to any embodiment described herein, is to be administered parenterally, such administration includes without limitation: intravenously, intraarterially, intrathecally, intraventricularly, intracranially, intramuscularly or subcutaneously administering the compound of the disclosure; and/or by using infusion techniques. Antibodies or fragments are typically administered parenterally, for example, intravenously.

Pharmaceutical compositions according to any embodiment described herein, suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or ascorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminum monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerin esters and suitable mixtures thereof. Suitable flowability may be maintained, by generation of liposomes, administration of a suitable particle size in the case of dispersions, or by the addition of surfactants.

For parenteral administration, the compound according to any embodiment described herein, is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound according to any embodiment described herein, with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the compounds and desired excipients for subsequent preparation of sterile solutions.

The compounds according to any embodiment described herein, may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary, with an added preservative. The pharmaceutical compositions for injection may be in the form of suspensions, solutions, or emulsions, in oily or aqueous vehicles, and may contain formulatory agents such as suspending, stabilizing, solubilizing and/or dispersing agents. Alternatively, the active ingredient may be in sterile powder form for reconstitution with a suitable vehicle, e.g., sterile, pyrogen-free water, before use.

The compounds according to any embodiment described herein, can be administered in the form of tablets, capsules, troches, ovules, elixirs, solutions or suspensions, for immediate-, delayed-, modified-, sustained-, pulsed- or controlled-release applications.

The compounds according to any embodiment described herein, may also be presented for human or veterinary use in a form suitable for oral or buccal administration, for example in the form of solutions, gels, syrups, or suspensions, or a dry powder for reconstitution with water or other suitable vehicle before use. Solid pharmaceutical compositions such as tablets, capsules, lozenges, troches, pastilles, pills, boluses, powder, pastes, granules, bullets or premix preparations may also be used. Solid and liquid pharmaceutical compositions for oral use may be prepared according to methods well-known in the art. Such pharmaceutical compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The pharmaceutical compositions according to any embodiment described herein, may be administered orally, in the form of rapid or controlled release tablets, microparticles, mini tablets, capsules, sachets, and oral solutions or suspensions, or powders for the preparation thereof. Oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the pharmaceutical compositions, e.g., act as both binders and disintegrants.

Examples of pharmaceutically acceptable disintegrants for oral pharmaceutical compositions according to any embodiment described herein, include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral pharmaceutical compositions according to any embodiment described herein, include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthine resin, alginates, magnesium aluminum silicate, polyethylene glycol or bentonite.

Examples of pharmaceutically acceptable fillers for oral pharmaceutical compositions according to any embodiment described herein, include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the pharmaceutical compositions according to any embodiment described herein, include, but are not limited to, magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odorants for the oral pharmaceutical compositions according to any embodiment described herein, include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral pharmaceutical compositions according to any embodiment described herein, include, but are not limited to, synthetic and natural dyes such as titanium dioxide, beta-carotene and extracts of grapefruit peel.

Examples of useful pharmaceutically acceptable coatings for the oral pharmaceutical compositions according to any embodiment described herein, typically used to facilitate swallowing, modify the release properties, improve the appearance, and/or mask the taste of the pharmaceutical compositions include, but are not limited to, hydroxypropylmethylcellulose, hydroxypropylcellulose and acrylate-methacrylate copolymers.

Suitable examples of pharmaceutically acceptable sweeteners for the oral pharmaceutical compositions according to any embodiment described herein, include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

As indicated, a compounds according to any embodiment described herein, can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of a compound according to any embodiment described herein, and a suitable powder base such as lactose or starch.

For topical administration by inhalation a compound according to any embodiment described herein, may be delivered for use in human or veterinary medicine via a nebulizer.

The pharmaceutical compositions of the disclosure may contain from 0.01 to 99% weight per volume of the active material. For topical administration, for example, the pharmaceutical composition will generally contain from 0.01-10%, more preferably 0.01-1% of the active material.

A compound according to any embodiment described herein, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form, according to any embodiment described herein, may be administered according to a dosage and administration regimen defined by routine testing in the light of the guidelines given above in order to obtain optimal activity while minimizing toxicity or side effects for a particular patient. The dosage of the compounds or unit dosage form may vary according to a variety of factors such as underlying disease conditions, the individual's condition, weight, sex and age, and the mode of administration. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter is within the scope of the disclosure. Clinically significant attenuation or amelioration means perceptible to the patient and/or to the physician.

In some embodiments, the amount of the compound to be administered can range between about 0.01 and about 25 mg/kg/day. Generally, dosage levels of between 0.01 to 25 mg/kg of body weight daily are administered to the patient, e.g., humans. In some embodiments the therapeutically effective amount is between a lower limit of about 0.01 mg/kg of body weight, about 0.1 mg/kg of body weight, about 0.2 mg/kg of body weight, about 0.3 mg/kg of body weight, about 0.4 mg/kg of body weight, about 0.5 mg/kg of body weight, about 0.60 mg/kg of body weight, about 0.70 mg/kg of body weight, about 0.80 mg/kg of body weight, about 0.90 mg/kg of body weight, about 1 mg/kg of body weight, about 2.5 mg/kg of body weight, about 5 mg/kg of body weight, about 7.5 mg/kg of body weight, about 10 mg/kg of body weight, about 12.5 mg/kg of body weight, about 15 mg/kg of body weight, about 17.5 mg/kg of body weight, about 20 mg/kg of body weight, about 22.5 mg/kg of body weight, and about 25 mg/kg of body weight; and an upper limit of 25 mg/kg of body weight, about 22.5 mg/kg of body weight, about 20 mg/kg of body weight, about 17.5 mg/kg of body weight, about 15 mg/kg of body weight, about 12.5 mg/kg of body weight, about 10 mg/kg of body weight, about 7.5 mg/kg of body weight, about 5 mg/kg of body weight, about 2.5 mg/kg of body weight, about 1 mg/kg of body weight, about 0.9 mg/kg of body weight, about 0.8 mg/kg of body weight, about 0.7 mg/kg of body weight, about 0.6 mg/kg of body weight, about 0.5 mg/kg of body weight, about 0.4 mg/kg of body weight, about 0.3 mg/kg of body weight, about 0.2 mg/kg of body weight, about 0.1 mg/kg of body weight, and about 0.01 mg/kg of body weight. In some embodiments, the therapeutically effective amount is about 0.1 mg/kg/day to about 10 mg/kg/day; in some embodiments the therapeutically effective amount is about 0.2 and about 5 mg/kg/day. It will be understood that the pharmaceutical formulations of the disclosure need not necessarily contain the entire amount of the compound that is effective in treating the disorder, as such effective amounts can be reached by administration of a plurality of divided doses of such pharmaceutical formulations. The compounds may be administered on a regimen of 1 to 4 times per day, such as once, twice, three times or four times per day.

In some embodiments of the disclosure, a compound according to any embodiment described herein, is formulated in capsules or tablets, usually containing about 10 to about 200 mg of the compounds. In some embodiments the capsule or tablet contains between a lower limit of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg; about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, and about 200 mg, and an upper limit of about 200 mg, about 195 mg, about 190 mg, about 185 mg, about 180 mg, about 175 mg, about 170 mg, about 165 mg, about 160 mg, about 155 mg, about 150 mg, about 145 mg, about 140 mg, about 135 mg, about 130 mg, about 125 mg, about 120 mg, about 115 mg, about 110 mg, about 105 mg, about 100 mg, about 95 mg, about 90 mg; about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, and about 10 mg of a compound according to any embodiment herein.

In some embodiments, a compound according to any embodiment herein is administered to a patient at a total daily dose of 50 mg to 500 mg. In some embodiments, the daily dose is between a lower limit of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg; about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg; about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, 300 mg, about 305 mg, about 310 mg, about 315 mg; about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395, about 400 mg, about 405 mg, about 410 mg, about 415 mg; about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, and about 500 mg and an upper limit of about 500 mg, about 495 mg, about 490 mg, about 485 mg, about 480 mg, about 475 mg, about 470 mg, about 465 mg, about 460 mg, about 455 mg, about 450 mg, about 445 mg, about 440 mg, about 435 mg, about 430 mg, about 425 mg, about 420 mg, about 415 mg, about 410 mg, about 405 mg, about 400 mg, about 395 mg, about 390 mg, about 385 mg, about 380 mg, about 375 mg, about 370 mg, about 365 mg, about 360 mg, about 355 mg, about 350 mg, about 345 mg, about 340 mg, about 335 mg, about 330 mg, about 325 mg, about 320 mg, about 315 mg, about 310 mg, about 305 mg about 300 mg, about 295 mg, about 290 mg, about 285 mg, about 280 mg, about 275 mg, about 270 mg, about 265 mg, about 260 mg, about 255 mg, about 250 mg, about 245 mg, about 240 mg, about 235 mg, about 230 mg, about 225 mg, about 220 mg, about 215 mg, about 210 mg, about 205 mg 200 mg, about 195 mg, about 190 mg, about 185 mg, about 180 mg, about 175 mg, about 170 mg, about 165 mg, about 160 mg, about 155 mg, about 150 mg, about 145 mg, about 140 mg, about 135 mg, about 130 mg, about 125 mg, about 120 mg, about 115 mg, about 110 mg, about 105 mg, about 100 mg, about 95 mg, about 90 mg; about 85 mg, about 80 mg, about 75 mg, about 70 mg, about 65 mg, about 60 mg, about 55 mg, and about 50 mg of a compound according to any embodiment herein. In some embodiments, the total daily dose is about 50 mg to 150 mg. In some embodiments, the total daily dose is about 50 mg to 250 mg. In some embodiments, the total daily dose is about 50 mg to 350 mg. In some embodiments, the total daily dose is about 50 mg to 450 mg. In some embodiments, the total daily dose is about 50 mg. In some embodiments the total daily dose is 100 mg. In some embodiments the total daily dose is 300 mg.

In some embodiments 2-(t-butoxy)-4-(3-methyl-3-(5-(methylsulfonyl)isoindolin-2-yl)butyl)phenol hemi-fumarate dihydrate salt crystal form E is administered at total daily dose of 100 mg. In some embodiments 2-(t-butoxy)-4-(3-methyl-3-(5-(methylsulfonyl)isoindolin-2-yl)butyl) phenol hemi-fumarate dihydrate salt crystal form E is administered at a total daily dose of 300 mg.

In some embodiments 2-(t-butoxy)-4-(3-methyl-3-(5-(methylsulfonyl)isoindolin-2-yl)butyl)phenol mono-fumarate salt crystal form A is administered at total daily dose is 100 mg. In some embodiments 2-(t-butoxy)-4-(3-methyl-3-(5-(methylsulfonyl)isoindolin-2-yl)butyl)phenol mono-fumarate salt crystal form A is administered at a total daily dose is 300 mg.

A pharmaceutical composition for parenteral administration contains from about 0.01% to about 100% of the active compound according to any embodiment described herein, based upon 100% weight of total pharmaceutical composition.

Generally, transdermal dosage forms contain from about 0.01% to about 100% of the active compound according to any embodiment described herein, versus 100% total weight of the dosage form.

The pharmaceutical composition or unit dosage form may be administered in a single daily dose, or the total daily dosage may be administered in divided doses. In addition, co administration or sequential administration of another compound for the treatment of the disorder may be desirable. To this purpose, the combined active principles are formulated into a simple dosage unit.

In some embodiments the total daily dose of a compound according to any embodiment described herein is 100 mg administered in a single daily dose. In some embodiments the total daily dose of a compound according to any embodiment described herein is 300 mg administered in a single daily dose. In some embodiments the total daily dose of a compound according to any embodiment described herein is 100 mg administered in divided doses. In some embodiments the total daily dose of a compound according to any embodiment described herein is 300 mg administered in divided doses.

In some embodiments a total daily dose of 100 mg of 2-(t-butoxy)-4-(3-methyl-3-(5-(methylsulfonyl)isoindolin-2-yl)butyl)phenol hemi-fumarate dihydrate salt crystal form E is administered in a single daily dose. In some embodiments a total daily dose of 300 mg of 2-(t-butoxy)-4-(3-methyl-3-(5-(methylsulfonyl)isoindolin-2-yl)butyl)phenol hemi-fumarate dihydrate salt crystal form E is administered in a single daily dose. In some embodiments a total daily dose of 100 mg of 2-(t-butoxy)-4-(3-methyl-3-(5-(methylsulfonyl)isoindolin-2-yl)butyl)phenol hemi-fumarate dihydrate salt crystal form E is administered in divided doses. In some embodiments a total daily dose of 300 mg of 2-(t-butoxy)-4-(3-methyl-3-(5-(methylsulfonyl)isoindolin-2-yl)butyl)phenol hemi-fumarate dihydrate salt crystal form E is administered in divided doses.

In some embodiments a total daily dose of 100 mg of 2-(t-butoxy)-4-(3-methyl-3-(5-(methylsulfonyl)isoindolin-2-yl)butyl)phenol mono-fumarate salt crystal form A is administered in a single daily dose. In some embodiments a total daily dose of 300 mg of 2-(t-butoxy)-4-(3-methyl-3-(5-(methylsulfonyl)isoindolin-2-yl)butyl)phenol mono-fumarate salt crystal form A is administered in a single daily dose. In some embodiments a total daily dose of 100 mg of 2-(t-butoxy)-4-(3-methyl-3-(5-(methylsulfonyl)isoindolin-2-yl)butyl)phenol mono-fumarate salt crystal form A is administered in divided doses. In some embodiments a total daily dose of 300 mg of 2-(t-butoxy)-4-(3-methyl-3-(5-(methylsulfonyl)isoindolin-2-yl)butyl)phenol mono-fumarate salt crystal form A is administered in divided doses.

Process for Preparing Crystalline forms of 2-(t-butoxy)-4-(3-methyl-3-(5-(methylsulfonyl)isoindolin-2-yl)butyl)phenol fumarate Salts Compounds of the present invention can be prepared according to the examples disclosed herein an as detailed below Additional Aspects Aspect 1. 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) comprising characteristic 2θ peaks at 9.69, 16.51, 17.23, 19.02, 25.10, and 26.49° (±0.2°).

Aspect 2. The crystal form E of aspect 1, wherein the XRPD further comprises peaks at 6.75, 11.09, 15.56, 16.35, 16.67, 20.43, 21.39, and 22.12° (±0.2°).

Aspect 3. The crystal form E of either of aspects 1 or 2, wherein the XRPD further comprises peaks at 17.04, 17.54, 19.41, and 29.45° (±0.2°).

Aspect 4. The crystal form E of any one of aspects 1-3, wherein the XRPD further comprises peaks at 15.34, 22.35, 26.71, 27.17, and 27.29° (±0.2°).

Aspect 5. The crystal form E of aspect 1, wherein the XRPD is substantially as shown in FIG. 40.

Aspect 6. The crystal form E of aspect 1, wherein the XRPD comprises peaks at 6.75, 8.33, 9.69, 11.09, 12.22, 12.62, 12.93, 13.49, 15.34, 15.56, 16.35, 16.51, 16.67, 17.04, 17.23, 17.54, 18.19, 18.44, 19.02, 19.41, 20.00, 20.26, 20.43, 20.71, 20.97, 21.39, 22.12, 22.35, 22.68, 23.35, 23.95, 24.23, 24.55, 24.82, 25.10, 25.51, 26.02, 26.28, 26.49, 26.71, 27.17, 27.29, 27.64, 27.98, 28.49, 28.95, 29.45, 30.25, 30.54, 31.24, 31.95, 33.39, 34.40, 35.41, 35.82, 36.33, 36.75, 37.89, 38.72, and 39.30° (±0.2°).

Aspect 7. The crystal form E of any one of aspects 1-6, characterized by a differential scanning calorimetry (DSC) curve that comprises a broad dehydration peak at T onset of about 90.8° C.

Aspect 8. The crystal form E of aspect 1, characterized by a differential scanning calorimetry curve substantially as shown in FIG. 41.

Aspect 9. The crystal form E of any one of aspects 1-8, which has a polymorph purity of at least 90% form E.

Aspect 10. The crystal form E of any one of aspects 1-8, which has a polymorph purity of at least 95% form E.

Aspect 11. The crystal form E of any one of aspects 1-8, which has a polymorph purity of at least 97% form E.

Aspect 12. The crystal form E of any one of aspects 1-8, which has a polymorph purity of at least 99% form E.

Aspect 13. The crystal form E of any one of aspects 1-12, which has a chemical purity of at least 95 A %.

Aspect 14. The crystal form E of any one of aspects 1-12, which has a chemical purity of at least 97 A %.

Aspect 15. The crystal form E of any one of aspects 1-12, which has a chemical purity of at least 99 A %.

Aspect 16. The crystal form E of aspect 1, which has a unit crystal that shows, in single-crystal analysis, the following crystal data:

| | |
|---|---|
| Crystal dimension (mm) | 0.15 × 0.12 × 0.08 |
| Temperature (K) | 170 |
| a (Å) | 32.5801(12) |
| b (Å) | 9.7212(4) |
| c (Å) | 21.2820(7) |
| α (°) | 90 |
| β (°) | 126.4700(10) |
| γ (°) | 90 |
| V (Å$^3$) | 5420.4(4) |
| Space Group | C2/c |
| Z | 8 |
| Chemical formula/ asymmetric unit | $C_{24}H_{34}NO_4S \cdot 0.5C_4H_2O_4 \cdot 2H_2O$ |
| Crystal density (g/cm$^3$) | 1.288 |

Aspect 17. 2-(t-butoxy)-4-(3-methyl-3-(5-(methylsulfonyl)isoindolin-2-yl)butyl)phenol mono-fumarate salt crystal form A characterized by an X-ray powder diffraction (XRPD) pattern comprising characteristic 2θ peaks at 5.23, 16.84, 17.41, 20.72 and 25.55° (±0.2°).

Aspect 18. The crystal form A of aspect 17, wherein the XRPD further comprises peaks at 6.73, 12.65, 21.06, 25.15 and 27.55° (+0.2°).

Aspect 19. The crystal form A of either of aspects 17 or 18, wherein the XRPD further comprises peaks at 12.51, 15.75, 20.25, 21.90, 22.15 and 27.12° (+0.2°).

Aspect 20. The crystal form A of any one of aspects 17-19, wherein the XRPD further comprises peaks at 15.55 and 19.55° (f 0.2°).

Aspect 21. The crystal form A of any one of aspects 17-20, wherein the XRPD further comprises peaks at 14.63, 23.28, 23.51, 24.65, and 31.98° (f 0.2°).

Aspect 22. The crystal form A of aspect 17, wherein the XRPD is substantially as shown in FIG. 1.

Aspect 23. The crystal form A of aspect 17 wherein the XRPD comprises peaks at 4.15, 5.23, 6.73, 8.36, 12.51, 12.65, 13.46, 14.26, 14.63, 15.55, 15.75, 16.36, 16.84, 17.41, 19.55, 20.25, 20.72, 21.06, 21.90, 22.15, 23.28, 23.51, 24.65, 25.15, 25.55, 26.49, 27.12, 27.55, 28.33, 28.99, 30.84, 31.98, 32.83, 34.32, 37.39, and 38.11° (±0.2°).

Aspect 24. The crystal form A of any one of aspects 17-23, characterized by a differential scanning calorimetry (DSC) curve that comprises a melting peak at T onset of about 161.3° C.

Aspect 25. The crystal form A of aspect 17, characterized by a differential scanning calorimetry substantially as shown in FIG. 2.

Aspect 26. The crystal form A of any one of aspects 17-25, which has a polymorph purity of at least 90% form A.

Aspect 27. The crystal form A of any one of aspects 17-25, which has a polymorph purity of at least 95% form A.

Aspect 28. The crystal form A of any one of aspects 17-25, which has a polymorph purity of at least 97% form A.

Aspect 29. The crystal form A of any one of aspects 17-25, which has a polymorph purity of at least 99% form A.

Aspect 30. The crystal form A of any one of aspects 17-29, which has a chemical purity of at least 95 A %.

Aspect 31. The crystal form A of any one of aspects 17-29, which has a chemical purity of at least 97 A %.

Aspect 32. The crystal form A of any one of aspects 17-29, which has a chemical purity of at least 99 A %.

Aspect 33. 2-(t-butoxy)-4-(3-methyl-3-(5-(methylsulfonyl)isoindolin-2-yl)butyl)phenol mono-fumarate salt, acetone solvate crystal form B characterized by an X-ray powder diffraction pattern (XRPD) comprising characteristic 2θ peaks at 6.09, 20.79, 21.05, 25.24, and 25.86° (+0.20).

Aspect 34. The crystal form B of aspect 33, wherein the XRPD further comprises peaks at 5.42, 12.55, 16.22, 16.83, and 20.08° (±0.2°).

Aspect 35. The crystal form B of aspects 33 or 34, wherein the XRPD further comprises peaks at 5.20, 11.13, 18.18, 19.29, 19.55, and 27.10° (±0.2°).

Aspect 36. The crystal form B of any one of aspects 33-35, wherein the XRPD further comprises peaks at 6.30, 10.81, 14.82, 15.18, 15.56, 17.08, 17.44, 18.50, 18.80, 21.68, 22.24, 22.89, and 24.38° (±0.2°).

Aspect 37. The crystal form B of aspect 33, wherein the XRPD is substantially as shown in FIG. 16.

Aspect 38. The crystal form B of aspect 33, wherein the XRPD comprises peaks at 3.51, 5.20, 5.42' 6.09' 6.30, 6.73, 10.02, 10.81, 11.13, 12.55, 14.39, 14.82, 15.18, 15.56, 16.22, 16.83, 17.08, 17.44, 18.18, 18.50, 18.80, 19.29, 19.55, 20.08, 20.79, 21.05, 21.68, 22.24, 22.89, 24.38, 25.24, 25.86, 27.10, 27.96, 28.95, 30.07, 31.11, 32.19, 33.77, 34.58, 35.06, 35.60, 36.83, and 38.020 (+0.2°).

Aspect 39. The crystal form B of any one of aspects 33-38, characterized by a differential scanning calorimetry (DSC) curve that comprises multiple thermal events including an endothermic peak at about 161.3° C.

Aspect 40. The crystal form B of aspect 33, characterized by a differential scanning calorimetry substantially as shown in FIG. 17.

Aspect 41. The crystal form B of any one of aspects 33-40, which has a polymorph purity of at least 90% form B.

Aspect 42. The crystal form B of any one of aspects 33-40, which has a polymorph purity of at least 95% form B.

Aspect 43. The crystal form B of any one of aspects 33-40, which has a polymorph purity of at least 97% form B.

Aspect 44. The crystal form B of any one of aspects 33-40, which has a polymorph purity of at least 99% form B.

Aspect 45. The crystal form B of any one of aspects 33-44, which has a chemical purity of at least 95 A %.

Aspect 46. The crystal form B of any one of aspects 33-44, which has a chemical purity of at least 97 A %.

Aspect 47. The 2-(t-butoxy)-4-(3-methyl-3-(5-(methylsulfonyl)isoindolin-2-yl)butyl)phenol mono-fumarate salt, acetone solvate of any one of aspects 33-44, which has a chemical purity of at least 99 A %.

Aspect 48. 2-(t-butoxy)-4-(3-methyl-3-(5-(methylsulfonyl)isoindolin-2-yl)butyl)phenol mono-fumarate salt, acetonitrile solvate crystal form C characterized by an X-ray powder diffraction pattern (XRPD) comprising characteristic 2θ peaks at 5.27, 16.47, 17.65, 19.36, and 21.09° (±0.2°).

Aspect 49. The crystal form C of aspect 48, wherein the XRPD further comprises peaks at 10.95, 12.71, 15.74, 20.79, 21.82, 25.53, and 27.37° (±0.2°).

Aspect 50. The crystal form C of aspects 48 or 49, wherein the XRPD further comprises peaks at 11.09, 16.22, 17.36, and 24.80° (+0.2°).

Aspect 51. The crystal form C of any one of aspects 48-50, wherein the XRPD further comprises peaks at 6.73, 18.42, 22.71, 22.88, 23.16, 23.79 and 26.43° (±0.2°).

Aspect 52. The crystal form C of aspect 48, wherein the XRPD is substantially as shown in FIG. 24.

Aspect 53. The crystal form C of aspect 48, wherein the XRPD comprises peaks at 5.27, 5.53, 6.73, 6.90, 8.32, 10.95, 11.09, 12.71, 13.10, 13.78, 15.10, 15.74, 16.22, 16.47, 17.36, 17.65, 18.42, 19.36, 20.26, 20.79, 21.09, 21.82, 22.71, 22.88, 23.16, 23.79, 24.32, 24.80, 25.53, 26.12, 26.43, 27.37, 29.70, 30.08, 31.39, 31.76, 32.57, 34.45. 35.01, 36.22, 37.00, 37.49, 38.46, 39.27° (±0.2°).

Aspect 54. The crystal form C of any one of aspects 48-53, characterized by a differential scanning calorimetry (DSC) curve that comprises thermal events at onset of about 101.2° C. and about 157.3° C.

Aspect 55. The crystal form C of aspect 48, characterized by a differential scanning calorimetry substantially as shown in FIG. 22.

Aspect 56. The crystal form C of any one of aspects 48-55, which has a polymorph purity of at least 90% form C.

Aspect 57. The crystal form C of any one of aspects 48-55, which has a polymorph purity of at least 95% form C.

Aspect 58. The crystal form C of any one of aspects 48-55, which has a polymorph purity of at least 97% form C.

Aspect 59. The crystal form C of any one of aspects 48-55, which has a polymorph purity of at least 99% form C.

Aspect 60. The crystal form C of any one of aspects 48-59, which has a chemical purity of at least 95 A %.

Aspect 61. The crystal form C of any one of aspects 48-59, which has a chemical purity of at least 97 A %.

Aspect 62. The crystal form C of any one of aspects 48-59, which has a chemical purity of at least 99 A %.

Aspect 63. 2-(t-butoxy)-4-(3-methyl-3-(5-(methylsulfonyl)isoindolin-2-yl)butyl)phenol mono-fumarate salt crystal form D characterized by an X-ray powder diffraction pattern (XRPD) comprising characteristic 2θ peaks at 5.24, 17.06, 17.49, and 27.12° (±0.2°).

Aspect 64. The crystal form D of aspect 63, wherein the XRPD further comprises peaks at 12.44, 15.70, 20.95, 24.87, and 25.12° (±0.2°).

Aspect 65. The crystal form D of aspects 63 or 64, wherein the XRPD further comprises peaks at 19.48, 22.14, and 24.70° (±0.2°).

Aspect 66. The crystal form D of aspects 63-65, wherein the XRPD further comprises peaks at 14.63, 16.44, 20.26, and 23.37° (±0.2°).

Aspect 67. The crystal form D of aspect 63, wherein the XRPD is substantially as shown in FIG. 25.

Aspect 68. The crystal form D of aspect 63, wherein the XRPD comprises peaks at 5.24, 6.74, 12.44, 14.63, 15.70, 16.44, 17.06, 17.49, 19.48, 20.26, 20.95, 22.14, 23.37, 24.70, 24.87, 25.12, 27.12, 32.21, and 37.63° (±0.2°).

Aspect 69. The crystal form D of any one of aspects 63-68, characterized by a differential scanning calorimetry (DSC) curve that comprises a melting onset of about 152.2° C.

Aspect 70. The crystal form D of aspect 63, characterized by a differential scanning calorimetry curve substantially as shown in FIG. 26.

Aspect 71. The crystal form D of any one of aspects 63-70, which has a polymorph purity of at least 90% form D.

Aspect 72. The crystal form D of any one of aspects 63-70, which has a polymorph purity of at least 95% form D.

Aspect 73. The crystal form D of any one of aspects 63-70, which has a polymorph purity of at least 97% form D.

Aspect 74. The crystal form D of any one of aspects 63-70, which has a polymorph purity of at least 99% form D.

Aspect 75. The crystal form D of any one of aspects 63-74, which has a chemical purity of at least 95 A %.

Aspect 76. The crystal form D of any one of aspects 63-74, which has a chemical purity of at least 97 A %.

Aspect 77. The crystal form D of any one of aspects 63-74, which has a chemical purity of at least 99 A %.

Aspect 78. 2-(t-butoxy)-4-(3-methyl-3-(5-(methylsulfonyl)isoindolin-2-yl)butyl)phenol mono-fumarate salt, hemi-hydrate crystal form F characterized by an X-ray powder diffraction pattern (XRPD) comprising characteristic 2θ peaks at 5.20, 12.51, 16.84, 20.84, and 25.14° (±0.2°).

Aspect 79. The crystal form F of aspect 78, wherein the XRPD further comprises peaks at 15.58, 17.44, and 27.12° (±0.2°).

Aspect 80. The crystal form F of aspects 78 or 79, wherein the XRPD further comprises peaks at 6.76 and 17.13° (±0.2°).

Aspect 81. The crystal form F of any one of aspects 78-80, wherein the XRPD further comprises peaks at 19.45, 20.30, 21.74, and 22.13° (±0.2°).

Aspect 82. The crystal form F of aspect 78, wherein the XRPD is substantially as shown in FIG. 29.

Aspect 83. The crystal form F of aspect 78, wherein the XRPD comprises peaks at 4.27, 5.20, 6.76, 8.43, 10.45, 12.26, 12.51, 12.94, 14.37, 14.63, 15.58, 16.35, 16.84, 17.13, 17.44, 18.56, 19.45, 20.06, 20.30, 20.84, 21.74, 22.13, 23.24, 23.70, 24.59, 25.14, 25.76, 25.85, 27.12, 27.54, 28.41, 29.01, 29.49, 30.98, 32.22, 32.89, 33.88, 34.58, 36.98, and 38.22° (±0.2°).

Aspect 84. The crystal form F of any one of aspects 78-83, characterized by a differential scanning calorimetry (DSC) curve that comprises a low dehydration onset of about 17.4° C. followed by a melting onset at about 160.6° C.

Aspect 85. The crystal form F of aspect 78, characterized by a differential scanning calorimetry curve substantially as shown in FIG. 30.

Aspect 86. The crystal form F of any one of aspects 78-85, which has a polymorph purity of at least 90% form F.

Aspect 87. The crystal form F of any one of aspects 78-85, which has a polymorph purity of at least 95% form F.

Aspect 88. The crystal form F of any one of aspects 78-85, which has a polymorph purity of at least 97% form F.

Aspect 89. The crystal form F of any one of aspects 78-85, which has a polymorph purity of at least 99% form F.

Aspect 90. The crystal form F of any one of aspects 78-89, which has a chemical purity of at least 95 A %.

Aspect 91. The crystal form F of any one of aspects 78-89, which has a chemical purity of at least 97 A %.

Aspect 92. The crystal form F of any one of aspects 78-89, which has a chemical purity of at least 99 A %.

Aspect 93. A pharmaceutical composition comprising 2-(t-butoxy)-4-(3-methyl-3-(5-(methylsulfonyl)isoindolin-2-yl)butyl)phenol hemi-fumarate dihydrate salt crystal form E according to aspect 1, and a pharmaceutically acceptable excipient.

Aspect 94. A pharmaceutical composition comprising 2-(t-butoxy)-4-(3-methyl-3-(5-(methylsulfonyl)isoindolin-2-yl)butyl)phenol hemi-fumarate dihydrate salt crystal form E according to any one of aspects 2-16, and a pharmaceutically acceptable excipient.

Aspect 95. A pharmaceutical composition comprising 2-(t-butoxy)-4-(3-methyl-3-(5-(methylsulfonyl)isoindolin-2-yl)butyl)phenol mono-fumarate salt crystal form A according to aspect 17, and a pharmaceutically acceptable excipient.

Aspect 96. A pharmaceutical composition comprising 2-(t-butoxy)-4-(3-methyl-3-(5-(methylsulfonyl)isoindolin-2-yl)butyl)phenol mono-fumarate salt crystal form A according to any one of aspects 18-32, and a pharmaceutically acceptable excipient.

Aspect 97. A pharmaceutical composition comprising 2-(t-butoxy)-4-(3-methyl-3-(5-(methylsulfonyl)isoindolin-2-yl)butyl)phenol mono-fumarate salt, acetone solvate crystal form B according to aspect 33, and a pharmaceutically acceptable excipient.

Aspect 98. A pharmaceutical composition comprising 2-(t-butoxy)-4-(3-methyl-3-(5-(methylsulfonyl)isoindolin-2-yl)butyl)phenol mono-fumarate salt, acetone solvate crystal form B according to any one of aspects 34-47, and a pharmaceutically acceptable excipient.

Aspect 99. A pharmaceutical composition comprising 2-(t-butoxy)-4-(3-methyl-3-(5-(methylsulfonyl)isoindolin-2-yl)butyl)phenol mono-fumarate salt, acetonitrile solvate crystal form C according to aspect 48, and a pharmaceutically acceptable excipient.

Aspect 100. A pharmaceutical composition comprising 2-(t-butoxy)-4-(3-methyl-3-(5-(methylsulfonyl)isoindolin-2-yl)butyl)phenol mono-fumarate salt crystal form C according to any one of aspects 49-62, and a pharmaceutically acceptable excipient.

Aspect 101. A pharmaceutical composition comprising 2-(t-butoxy)-4-(3-methyl-3-(5-(methylsulfonyl)isoindolin-2-yl)butyl)phenol mono-fumarate salt crystal form D according to aspect 63, and a pharmaceutically acceptable excipient.

Aspect 102. A pharmaceutical composition comprising 2-(t-butoxy)-4-(3-methyl-3-(5-(methylsulfonyl)isoindolin-2-yl)butyl)phenol mono-fumarate salt crystal form D according to any one of aspects 64-77, and a pharmaceutically acceptable excipient.

Aspect 103. A pharmaceutical composition comprising 2-(t-butoxy)-4-(3-methyl-3-(5-(methylsulfonyl)isoindolin-2-yl)butyl)phenol mono-fumarate salt hemi-hydrate crystal form F of according to aspect 78, and a pharmaceutically acceptable excipient.

Aspect 104. A pharmaceutical composition comprising 2-(t-butoxy)-4-(3-methyl-3-(5-(methylsulfonyl)isoindolin-2-yl)butyl)phenol mono-fumarate salt hemi-hydrate the crystal form F of according to any one of aspects 79-92, and a pharmaceutically acceptable excipient.

Aspect 105. Use of a pharmaceutical composition according to any one of aspects 93-104, in treating a disease selected from the group consisting of Alzheimer's Disease, Dementia with Lewy Bodies and Dry age-related macular degeneration.

Aspect 106. Use of a compound according to any one of aspects 1-92, in the manufacture of a medicament for treating a disease selected from the group consisting of Alzheimer's Disease, Dementia with Lewy Bodies and Dry age-related macular degeneration.

Aspect 107. A pharmaceutical composition according to any one of aspects 93-104, for use in treating a disease selected from the group consisting of Alzheimer's Disease, Dementia with Lewy Bodies and Dry age-related macular degeneration.

Aspect 108. A method of treating a disease selected from the group consisting of Alzheimer's Disease, Dementia with Lewy Bodies and Dry age-related macular degeneration in a subject in need thereof, comprising treating the subject with a compound according to any one of aspects 1-92, or a pharmaceutical composition according to any one of aspects 93-104.

Aspect 109. A process for preparing the 2-(t-butoxy)-4-(3-methyl-3-(5-(methylsulfonyl)isoindolin-2-yl)butyl) phenol hemi-fumarate dihydrate salt crystal form E according to any one of aspects 1-16 comprising: a) heating 2-(t-butoxy)-4-(3-methyl-3-(5-(methylsulfonyl)isoindolin-2-yl)butyl)phenol, and fumaric acid in ethanol to form a solution; b) slowly adding water to the solution of step a) to form a slurry and c) slowly cooling the slurry to obtain the 2-(t-butoxy)-4-(3-methyl-3-(5-(methylsulfonyl)isoindolin-2-yl)butyl) phenol hemi-fumarate dihydrate salt crystal form E.

Aspect 110. The process of either of aspects 109, wherein the heating in step a) is a temperature of about 55° C.

Aspect 111. The process of either of aspects 109-110, wherein the fumaric acid is 0.5 equivalents (moles) to 1 equivalent (moles) of 2-(t-butoxy)-4-(3-methyl-3-(5-(methylsulfonyl)isoindolin-2-yl)butyl)phenol.

Aspect 112. The process of any one of aspects 109-111, wherein the solution of step a) is filtered through a cartridge and the solution temperature readjusted to about 50° C. prior to step b).

Aspect 113. The process of any one of aspects 109-112, wherein the water in step b) is added over a period of about 1 hour.

Aspect 114. The process of any one of aspects 109-113, wherein the volume of ethanol in step a) to water in step b) is about 90/10 v/v.

Aspect 115. The process of any one of aspects 109-114, wherein seed crystals of 2-(t-butoxy)-4-(3-methyl-3-(5-(methylsulfonyl)isoindolin-2-yl)butyl)phenol hemi-fumarate dihydrate salt crystal form E are added after addition of water in step b) and prior to step c).

Aspect 116. The process of aspects 115, wherein the seed crystals are added at an amount of about 1% by weight relative to the 2-(t-butoxy)-4-(3-methyl-3-(5-(methylsulfonyl)isoindolin-2-yl)butyl)phenol.

Aspect 117. The process of any one of aspects 109-116, wherein the slurry is aged at 50° C. for about 90 minutes prior to step c).

Aspect 118. The process of any one of aspects 109-117, wherein the cooling in step c) is a temperature of about 20° C.

Aspect 119. The process of any one of aspects 109-118 wherein the slowly cooling takes place over a period of about 11 hours.

Aspect 120. The process of any one of aspects 109-119, further comprising isolating the 2-(t-butoxy)-4-(3-methyl-3-(5-(methylsulfonyl)isoindolin-2-yl)butyl) phenol hemi-fumarate dihydrate salt crystal form E.

Aspect 121. The process of aspect 120, wherein the isolating comprises filtering the slurry of step c).

Aspect 122. A process for preparing the 2-(t-butoxy)-4-(3-methyl-3-(5-(methylsulfonyl)isoindolin-2-yl)butyl) phenol hemi-fumarate dihydrate salt crystal form E according to any one of aspects 1-16 comprising: a) heating 1 equivalent (moles) of 2-(t-butoxy)-4-(3-methyl-3-(5-(methylsulfonyl)isoindolin-2-yl)butyl) phenol, and 0.5 equivalents (moles) of fumaric acid in ethanol at about 55° C. to form a solution; b) clarifying the solution through a cartridge, collecting the solution and readjusting the temperature of the solution to about 50° C.; c) adding water to the solution in step b) over a period of about 1 hour, followed by the addition of about 1% of seed crystals to form a slurry, wherein the amount of water added achieves about a 90/10 v/v ethanol to water; d) aging the slurry of step c) for about 90 minutes at about 50° C.; e) cooling the slurry of step d) to 20° C. over about 11 hours; to obtain the 2-(t-butoxy)-4-(3-methyl-3-(5-(methylsulfonyl)isoindolin-2-yl)butyl)phenol hemi-fumarate dihydrate salt crystal form E.

Aspect 123. The process of aspect 122, wherein the process further comprises f) isolating the 2-(t-butoxy)-4-(3-methyl-3-(5-(methylsulfonyl)isoindolin-2-yl) butyl)phenol hemi-fumarate dihydrate salt crystal form E.

Aspect 124. The process of aspect 123, wherein the isolating comprises filtering the slurry of step e).

Aspect 125. A polymorph of 2-(t-butoxy)-4-(3-methyl-3-(5-(methylsulfonyl)isoindolin-2-yl)butyl)phenol fumarate salt, wherein at least 95% (add w/w etc.) of the polymorph is 2-(t-butoxy)-4-(3-methyl-3-(5-(methylsulfonyl)isoindolin-2-yl)butyl)phenol hemi-fumarate dihydrate salt of crystal form E characterized by an X-ray powder diffraction pattern (XRPD) comprising characteristic 2θ peaks at 9.69, 16.51, 17.23, 19.02, 25.10, and 26.49° (±0.2°).

Aspect 126. The polymorph of aspect 125, wherein the XRPD further comprises peaks at 6.75, 11.09, 15.56, 16.35, 16.67, 20.43, 21.39, and 22.120 (+0.2°).

Aspect 127. The polymorph of either of aspects 125 or 126, wherein the XRPD further comprises peaks at 17.04, 17.54, 19.41, and 29.45° (±0.2°).

Aspect 128. The polymorph of any one of aspects 125-127, wherein the XRPD further comprises peaks at 15.34, 22.35, 26.71, 27.17, and 27.29° (+0.2°).

Aspect 129. The polymorph of aspect 125, wherein the XRPD is substantially as shown in FIG. 40

Aspect 130. The polymorph of aspect 125, wherein the XRPD comprises peaks at 6.75, 8.33, 9.69, 11.09, 12.22, 12.62, 12.93, 13.49, 15.34, 15.56, 16.35, 16.51, 16.67, 17.04, 17.23, 17.54, 18.19, 18.44, 19.02, 19.41, 20.00, 20.26, 20.43, 20.71, 20.97, 21.39, 22.12, 22.35, 22.68, 23.35, 23.95, 24.23, 24.55, 24.82, 25.10, 25.51, 26.02, 26.28, 26.49, 26.71, 27.17, 27.29, 27.64, 27.98, 28.49, 28.95, 29.45, 30.25, 30.54, 31.24, 31.95, 33.39, 34.40, 35.41, 35.82, 36.33, 36.75, 37.89, 38.72, and 39.30° (±0.2°).

Aspect 131. The polymorph of any one of aspects 125-130, characterized by a differential scanning calorimetry (DSC) curve that comprises a broad dehydration peak at T onset of about 90.8° C.

Aspect 132. The polymorph of aspect 125, characterized by a differential scanning calorimetry curve substantially as shown in FIG. 41.

Aspect 133. The polymorph of any one of aspects 125-132, which has a polymorph purity of at least 97% crystal form E.

Aspect 134. The polymorph of any one of aspects 125-132, which has a polymorph purity of at least 99% crystal form E.

Aspect 135. The polymorph of any one of aspects 125-134, which has a chemical purity of at least 95 A %.

Aspect 136. The polymorph of any one of aspects 125-134, which has a chemical purity of at least 97 A %.

Aspect 137. The polymorph of any one of aspects 125-134, which has a chemical purity of at least 99 A %.

Aspect 138. The polymorph of aspect 125, the unit crystal of which shows, in single-crystal analysis, the following crystal data:

| | |
|---|---|
| Crystal dimension (mm) | 0.15 × 0.12 × 0.08 |
| Temperature (K) | 170 |
| a (Å) | 32.5801(12) |
| b (Å) | 9.7212(4;) |
| c (Å) | 21.2820(7) |
| α (°) | 90 |
| β (°) | 126.4700(10) |
| γ (°) | 90 |
| V (Å3) | 5420.4(4) |
| Space Group | C2/c |
| Z | 8 |
| Chemical formula/ asymmetric unit | $C_{24}H_{34}NO_4S•0.5C_4H_2O_4•2H_2O$ |
| Crystal density (g/cm$^3$) | 1.288 |

Aspect 139. A polymorph of 2-(t-butoxy)-4-(3-methyl-3-(5-(methylsulfonyl)isoindolin-2-yl)butyl)phenol fumarate salt, wherein the polymorph has a polymorph purity of at least 95% (add w/w etc.) of 2-(t-butoxy)-4-(3-methyl-3-(5-(methylsulfonyl)isoindolin-2-yl) butyl)phenol mono-fumarate salt crystal form A, characterized by an X-ray powder diffraction (XRPD) pattern comprising characteristic 2θ peaks at 5.23, 16.84, 17.41, 20.72 and 25.55° (±0.2°).

Aspect 140. The polymorph of aspect 139, wherein the XRPD further comprises peaks at 6.73, 12.65, 21.06, 25.15 and 27.55° (+0.2°).

Aspect 141. The polymorph of either of aspects 139 or 140, wherein the XRPD further comprises peaks at 12.51, 15.75, 20.25, 21.90, 22.15 and 27.12° (±0.2°).

Aspect 142. The polymorph of any one of aspects 139-141, wherein the XRPD further comprises peaks at 15.55 and 19.55° (±0.2°).

Aspect 143. The polymorph of any one of aspects 139-142, wherein the XRPD further comprises peaks at 14.63, 23.28, 23.51, 24.65, and 31.98° (±0.2°).

Aspect 144. The polymorph of aspect 139, wherein the XRPD is substantially as shown in FIG. 1.

Aspect 145. The polymorph of aspect 139 wherein the XRPD comprises peaks at 4.15, 5.23, 6.73, 8.36, 12.51, 12.65, 13.46, 14.26, 14.63, 15.55, 15.75, 16.36, 16.84, 17.41, 19.55, 20.25, 20.72, 21.06, 21.90, 22.15, 23.28, 23.51, 24.65, 25.15, 25.55, 26.49, 27.12, 27.55, 28.33, 28.99, 30.84, 31.98, 32.83, 34.32, 37.39, and 38.11° (+0.2°).

Aspect 146. The polymorph of any one of aspects 139-145, characterized by a differential scanning calorimetry (DSC) curve that comprises a melting peak at T onset of about 161.3° C.

Aspect 147. The polymorph of aspect 139, characterized by a differential scanning calorimetry curve substantially as shown in FIG. 2.

Aspect 148. The polymorph of any one of aspects 139-147, which has a polymorph purity of at least 97% crystal form A.

Aspect 149. The polymorph of any one of aspects 139-147, which has a polymorph purity of at least 99% crystal form A.

Aspect 150. The polymorph of t of any one of aspects 139-149, which has a chemical purity of at least 95 A %.

Aspect 151. The polymorph of any one of aspects 139-149, which has a chemical purity of at least 97 A %.

Aspect 152. The polymorph of any one of aspects 139-149, which has a chemical purity of at least 99 A %.

Aspect 153. A polymorph of 2-(t-butoxy)-4-(3-methyl-3-(5-(methylsulfonyl)isoindolin-2-yl)butyl)phenol fumarate salt, wherein the polymorph has a polymorph purity of at least 95% (add w/w etc.) of 2-(t-butoxy)-4-(3-methyl-3-(5-(methylsulfonyl)isoindolin-2-yl) butyl)phenol mono-fumarate salt, acetone solvate of crystal form B characterized by an X-ray powder diffraction (XRPD) pattern comprising characteristic 2θ peaks at 6.09, 20.79, 21.05, 25.24, and 25.86° (±0.2°).

Aspect 154. The polymorph of aspect 153, wherein the XRPD further comprises peaks at 5.42, 12.55, 16.22, 16.83, and 20.08° (±0.2°).

Aspect 155. The polymorph of either of aspects 153 or 154, wherein the XRPD further comprises peaks at 5.20, 11.13, 18.18, 19.29, 19.55, and 27.10° (±0.2°).

Aspect 156. The polymorph of any one of aspects 153-155, wherein the XRPD further comprises peaks at 6.30, 10.81, 14.82, 15.18, 15.56, 17.08, 17.44, 18.50, 18.80, 21.68, 22.24, 22.89, and 24.38° (±0.2°).

Aspect 157. The polymorph of aspect 153, wherein the XRPD is substantially as shown in FIG. 16.

Aspect 158. The polymorph of aspect 153, wherein the XRPD comprises peaks at 3.51, 5.20, 5.42' 6.09' 6.30, 6.73, 10.02, 10.81, 11.13, 12.55, 14.39, 14.82, 15.18, 15.56, 16.22, 16.83, 17.08, 17.44, 18.18, 18.50, 18.80, 19.29, 19.55, 20.08, 20.79, 21.05, 21.68, 22.24, 22.89, 24.38, 25.24, 25.86, 27.10, 27.96, 28.95, 30.07, 31.11, 32.19, 33.77, 34.58, 35.06, 35.60, 36.83, and 38.02° (±0.2°).

Aspect 159. The polymorph of any one of aspects 153-158, characterized by a differential scanning calorimetry (DSC) curve that comprises multiple thermal events including an endothermic peak at about 161.3° C.

Aspect 160. The polymorph of aspect 153, characterized by a differential scanning calorimetry curve substantially as shown in FIG. 17.

Aspect 161. The polymorph of any one of aspects 153-160, which has a polymorph purity of at least 97% crystal form B.

Aspect 162. The polymorph of any one of aspects 153-160, which has a polymorph purity of at least 99% crystal form B.

Aspect 163. The polymorph of aspects 153-162, which has a chemical purity of at least 95 A %.

Aspect 164. The polymorph of any one of aspects 153-162, which has a chemical purity of at least 97 A %.

Aspect 165. The polymorph of any one of aspects 153-162, which has a chemical purity of at least 99 A %.

Aspect 166. A polymorph of 2-(t-butoxy)-4-(3-methyl-3-(5-(methylsulfonyl)isoindolin-2-yl)butyl)phenol fumarate salt, wherein the polymorph has a polymorph purity of at least 95% (add w/w etc.) of 2-(t-butoxy)-4-(3-methyl-3-(5-(methylsulfonyl)isoindolin-2-yl) butyl)phenol mono-fumarate salt, acetonitrile solvate of crystal form C characterized by an X-ray powder diffraction (XRPD) pattern comprising characteristic 2θ peaks at 5.27, 16.47, 17.65, 19.36, and 21.09° (±0.2°).

Aspect 167. The polymorph of aspect 166, wherein the XRPD further comprises peaks at 10.95, 12.71, 15.74, 20.79, 21.82, 25.53, and 27.37° (±0.2°).

Aspect 168. The polymorph of either of aspects 166 or 167, wherein the XRPD further comprises peaks at 11.09, 16.22, 17.36, and 24.80° (±0.2°).

Aspect 169. The polymorph of any one of aspects 166-168, wherein the XRPD further comprises peaks at 6.73, 18.42, 22.71, 22.88, 23.16, 23.79 and 26.43° (±0.2°).

Aspect 170. The polymorph of aspect 166, wherein the XRPD is substantially as shown in FIG. 24.

Aspect 171. The polymorph of aspect 166, wherein the XRPD comprises peaks at 5.27, 5.53, 6.73, 6.90, 8.32, 10.95, 11.09, 12.71, 13.10, 13.78, 15.10, 15.74, 16.22, 16.47, 17.36, 17.65, 18.42, 19.36, 20.26, 20.79, 21.09, 21.82, 22.71, 22.88, 23.16, 23.79, 24.32, 24.80, 25.53, 26.12, 26.43, 27.37, 29.70, 30.08, 31.39, 31.76, 32.57, 34.45. 35.01, 36.22, 37.00, 37.49, 38.46, 39.27° (±0.2°).

Aspect 172. The polymorph of any one of aspects 166-171, characterized by a differential scanning calorimetry (DSC) curve that comprises thermal events at onset of about 101.2° C. and about 157.3° C.

Aspect 173. The polymorph of aspect 166, characterized by a differential scanning calorimetry curve substantially as shown in FIG. 22.

Aspect 174. The polymorph of any one of aspects 166-173, which has a polymorph purity of at least 97% crystal form C.

Aspect 175. The polymorph of any one of aspects 166-173, which has a polymorph purity of at least 99% crystal form C.

Aspect 176. The polymorph of any one of aspects 166-175, which has a chemical purity of at least 95 A %.

Aspect 177. The polymorph of any one of aspects 166-175, which has a chemical purity of at least 97 A %.

Aspect 178. The polymorph of any one of aspects 166-175, which has a chemical purity of at least 99 A %.

Aspect 179. A polymorph of 2-(t-butoxy)-4-(3-methyl-3-(5-(methylsulfonyl)isoindolin-2-yl)butyl)phenol fumarate salt, wherein the polymorph has a polymorph purity of at least 95% (add w/w etc.) of 2-(t-butoxy)-4-(3-methyl-3-(5-(methylsulfonyl)isoindolin-2-yl) butyl)phenol mono-fumarate salt of crystal form D characterized by an X-ray powder diffraction (XRPD) pattern comprising characteristic 2θ peaks at 5.24, 17.06, 17.49, and 27.12° (±0.2°).

Aspect 180. The polymorph of aspect 179, wherein the XRPD further comprises peaks at 12.44, 15.70, 20.95, 24.87, and 25.12° (±0.2°).

Aspect 181. The polymorph of either of aspect 179 or 180, wherein the XRPD further comprises peaks at 19.48, 22.14, and 24.70° (±0.2°).

Aspect 182. The polymorph of any one of aspects 179-181, wherein the XRPD further comprises peaks at 14.63, 16.44, 20.26, and 23.37° (±0.2°).

Aspect 183. The polymorph of aspect 179, wherein the XRPD is substantially as shown in FIG. 25.

Aspect 184. The polymorph of aspect 179, wherein the XRPD comprises peaks at 5.24, 6.74, 12.44, 14.63, 15.70, 16.44, 17.06, 17.49, 19.48, 20.26, 20.95, 22.14, 23.37, 24.70, 24.87, 25.12, 27.12, 32.21, and 37.63° (±0.2°).

Aspect 185. The polymorph of any one of aspects 179-184, characterized by a differential scanning calorimetry (DSC) curve that comprises a melting onset of about 152.2° C.

Aspect 186. The polymorph of aspect 179, characterized by a differential scanning calorimetry curve substantially as shown in FIG. 26.

Aspect 187. The polymorph of any one of aspects 179-186, which has a polymorph purity of at least 97% crystal form D.

Aspect 188. The polymorph of any one of aspects 179-186, which has a polymorph purity of at least 99% crystal form D.

Aspect 189. The polymorph of any one of aspects 179-188, which has a chemical purity of at least 95 A %.

Aspect 190. The polymorph of any one of aspects 179-188, which has a chemical purity of at least 97 A %.

Aspect 191. The polymorph of any one of aspects 179-188, which has a chemical purity of at least 99 A %.

Aspect 192. A polymorph of 2-(t-butoxy)-4-(3-methyl-3-(5-(methylsulfonyl)isoindolin-2-yl)butyl)phenol fumarate salt, wherein the polymorph has a polymorph purity of at least 95% (add w/w etc.) of 2-(t-butoxy)-4-(3-methyl-3-(5-(methylsulfonyl)isoindolin-2-yl) butyl)phenol mono-fumarate salt, hemi-hydrate of crystal form F characterized by an X-ray powder diffraction (XRPD) pattern comprising characteristic 2θ peaks at 5.20, 12.51, 16.84, 20.84, and 25.14° (±0.2°).

Aspect 193. The polymorph of aspect 192, wherein the XRPD further comprises peaks at 15.58, 17.44, and 27.12° (±0.2°).

Aspect 194. The polymorph of either of aspects 192 or 193, wherein the XRPD further comprises peaks at 6.76 and 17.13° (±0.2°).

Aspect 195. The polymorph of any one of aspects 192-194, wherein the XRPD further comprises peaks at 19.45, 20.30, 21.74, and 22.13° (±0.2°).

Aspect 196. The polymorph of aspect 192, wherein the XRPD is substantially as shown in FIG. 29.

Aspect 197. The polymorph of aspect 192, wherein the XRPD comprises peaks at 4.27, 5.20, 6.76, 8.43, 10.45, 12.26, 12.51, 12.94, 14.37, 14.63, 15.58, 16.35, 16.84, 17.13, 17.44, 18.56, 19.45, 20.06, 20.30, 20.84, 21.74, 22.13, 23.24, 23.70, 24.59, 25.14, 25.76, 25.85, 27.12, 27.54, 28.41, 29.01, 29.49, 30.98, 32.22, 32.89, 33.88, 34.58, 36.98, and 38.22° (±0.2°).

Aspect 198. The polymorph of any one of aspects 192-197, characterized by a differential scanning calorimetry (DSC) curve that comprises a low dehydration onset of about 17.4° C. followed by a melting onset at about 160.6° C.

Aspect 199. The polymorph of aspect 192, characterized by a differential scanning calorimetry curve substantially as shown in FIG. 30.

Aspect 200. The polymorph of any one of aspects 192-199, which has a polymorph purity of at least 97% crystal form F.

Aspect 201. The polymorph of any one of aspects 192-199, which has a polymorph purity of at least 99% crystal form F.

Aspect 202. The polymorph of any one of aspects 192-201, which has a chemical purity of at least 95 A %.

Aspect 203. The polymorph of any one of aspects 192-201, which has a chemical purity of at least 97 A %.

Aspect 204. The polymorph of any one of aspects 192-201, which has a chemical purity of at least 99 A %.

Aspect 205. A pharmaceutical composition comprising a polymorph according to aspect 125, and a pharmaceutically acceptable excipient.

Aspect 206. A pharmaceutical composition comprising a polymorph according to any one of aspects 126-138, and a pharmaceutically acceptable excipient.

Aspect 207. A pharmaceutical composition comprising a polymorph according to aspect 139, and a pharmaceutically acceptable excipient.

Aspect 208. A pharmaceutical composition comprising a polymorph according to any one of aspects 140-152, and a pharmaceutically acceptable excipient.

Aspect 209. A pharmaceutical composition comprising a polymorph, according to aspect 153, and a pharmaceutically acceptable excipient.

Aspect 210. A pharmaceutical composition comprising a polymorph according to any one of aspects 154-165, and a pharmaceutically acceptable excipient.

Aspect 211. A pharmaceutical composition comprising a polymorph according to aspect 166, and a pharmaceutically acceptable excipient.

Aspect 212. A pharmaceutical composition comprising a polymorph according to any one of aspects 167-178, and a pharmaceutically acceptable excipient.

Aspect 213. A pharmaceutical composition comprising a polymorph according to aspect 179, and a pharmaceutically acceptable excipient.

Aspect 214. A pharmaceutical composition comprising a polymorph according to any one of aspects 180-191, and a pharmaceutically acceptable excipient.

Aspect 215. A pharmaceutical composition comprising a polymorph according to aspect 192, and a pharmaceutically acceptable excipient.

Aspect 216. A pharmaceutical composition comprising a polymorph according to any one of aspects 193-204, and a pharmaceutically acceptable excipient.

Aspect 217. Use of a pharmaceutical composition according to any one of aspects 205-216, in treating a disease selected from the group consisting of Alzheimer's Disease, Dementia with Lewy Bodies and Dry age-related macular degeneration.

Aspect 218. Use of a polymorph according to any one of aspects 125-204, in the manufacture of a medicament for treating a disease selected from the group consisting of Alzheimer's Disease, Dementia with Lewy Bodies and Dry age-related macular degeneration.

Aspect 219. A pharmaceutical composition according to any one of aspects 205-216, for use in treating a disease selected from the group consisting of Alzheimer's Disease, Dementia with Lewy Bodies and Dry age-related macular degeneration.

Aspect 220. A method of treating a disease selected from the group consisting of Alzheimer's Disease, Dementia with Lewy Bodies and Dry age-related macular degeneration in a subject in need thereof, comprising treating the subject with a polymorph according to any one of aspects 125-204, or a pharmaceutical composition according to any one of aspects 205-216.

Although the present invention has been described in considerable detail with reference to certain preferred embodiments thereof, other versions are possible. Therefore, the spirit and scope of the appended claims should not be limited to the description and the preferred versions contained within this specification. Various embodiments of the present invention will be illustrated with reference to the following non-limiting examples. The following examples are for illustrative purposes only and are not to be construed as limiting the invention in any manner.

As used herein the symbols and conventions used in these processes, schemes and examples are consistent with those used in the contemporary scientific literature. Unless otherwise noted, all starting materials were obtained from commercial suppliers and used without further purification. Specifically, the following abbreviations may be used in the examples and throughout the specification:

EXAMPLES

| Abbreviations | |
|---|---|
| 2-MeTHF | 2-methyl tetrahydrofuran |
| A % | area % (HPLC or GC) |
| A | ampere |
| AcOH | acetic acid |
| AIBN | Azobisisobutyronitrile |
| API | active pharmaceutical ingredient |
| aq | aqueous |
| DBU | 1,8-diazabicyclo[5.4.0]undec-7-ene |
| DCE | dichloroethane |
| DCM | dichloromethane |
| DIPEA | diisopropyl ethylamine |
| DMF | dimethylformamide |
| DMSO | dimethylsulfoxide |
| equiv | equivalents |
| EtOAc | ethyl acetate |
| EtOH | ethanol |
| g | gram |
| h | hour/hours |
| IPA | isopropyl alcohol or 2-propanol |
| IpAc | isopropyl acetate |
| kg | kilograms |

-continued

| Abbreviations | |
|---|---|
| L | liter(s) |
| LC | liquid chromatography |
| LED | light emitting diode |
| m.p. | melting point |
| MeCN | acetonitrile |
| MeOH | methanol |
| mm | millimeter |
| MsOH | methane sulfonic acid |
| MTBE | methyl tert-butyl ether |
| NaOH | sodium hydroxide |
| NBS | N-bromosuccinimide |
| nm | nanometer |
| NMR | nuclear magnetic resonance |
| NMT | not more than |
| OD | outer diameter |
| P | phosphorus |
| Ph | phase |
| ppm | parts per million |
| psi | pounds per square inch |
| RH | Relative humidity |
| RT | room temperature |
| TEA | triethyl amine |
| THF | tetrahydrofuran |
| V | volumes |
| wt % | weight % |
| XRPD | x-ray powder diffraction |

XRPD Method

XRPD was performed on a Bruker D8 Advance using a LYNXEYE_XE_T(1D mode) detector, an open angle of 2.94°, a continuous PSD fast scan mode, and Cu/K-alpha1 radiation with a wavelength of λ=1.5418 Å. The X-ray generator power was 40 kV/40 mA. A step size of 0.020 at 0.12 seconds per step was used, with a scan range of 3° to 40°. Primary beam path slits were Twin Primary motorized slits of 10.0 mm by sample length with a SollerMount axial soller of 2.5°. Secondary beam path slits were Twin_Secondary motorized slit of 5.2 mm with a Detector Optics Mount soller slit at 2.5°. The sample rotation speed was 15 rpm.

DSC Method

DSC was performed on a TA Discovery 2500 or Q2000 using a Tzero pan and Tzero hermetic lid with a pin hole for the sample. The mass of the sample was approximately 1 to 2 mg. A temperature range of 0 to 250° C. was evaluated with a heating rate of 10° C./min and 50 mL/min of nitrogen flow.

TGA Method

TGA was performed on a TA Discovery 5500 or Q5000 using an aluminum sample pan. Nitrogen flow was 10 mL/min to the balance and 25 mL/min to the sample. The mass of the sample was approximately 2 to 10 mg. Starting temperature was roughly ambient condition (below 35° C.) with a heating rate of 10° C./min. The final temperature was 300° C., provided the weight loss of the compound did not exceed 20% (w/w). If weight loss of the sample exceeded 20% (w/w), the following segment was aborted.

Karl Fischer

Karl Fischer titration was performed on a Mettler Toledo Coulometric KF Titrator C30 using a coulometric method.

$^1$H NMR Method $^1$H NMR was performed on a Bruker Advance AV 400M using a frequency of 400 MHz and a 5 mm PABBO BB-1H/D probe. A temperature of 297.6 K was used for 8 scans with a 1 second relaxation delay.

HPLC Method

HPLC was performed on a Shimadzu LC-20ADXR. The method used a Zorbax SB-C 18, 150×4.6 mm, 5 μm column with a 220 nm UV detector. The column temperature was 40° C. with a flow rate of 1.2 mL/min. Mobile phase A was 0.1% TFA in water and mobile phase B was acetonitrile. The injection volume was 5 μL. A gradient of mobile phase A and mobile phase B was used as follows: 0.0 min (95% A, 5% B), 0.01 min (95% A, 5% B), 9.0 min (5% A, 95% B), 13.0 min (5% A, 95% B), 13.1 min (95% A, 5% B), 17.0 min (95% A, 5% B).

Example 1: Preparation of 2-(t-butoxy)-4-(3-methyl-3-(5-(methylsulfonyl)isoindolin-2-yl)butyl) phenol mono-fumarate Salt Crystal Form A

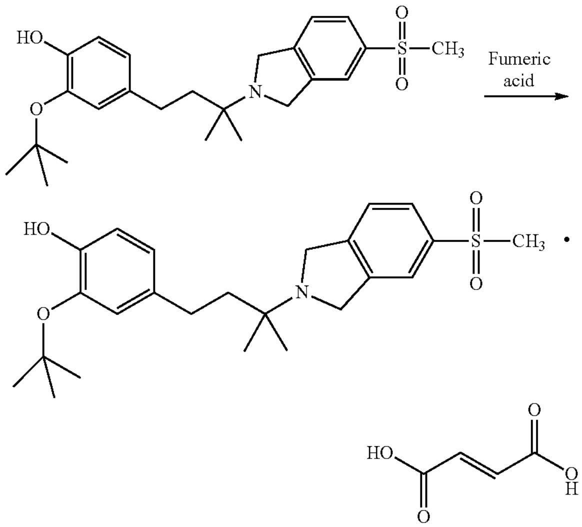

2-(t-butoxy)-4-(3-methyl-3-(5-(methylsulfonyl)isoindolin-2-yl)butyl)phenol (CT1812 free base, 100.00 kg) was charged to a reactor with THF (892.9 kg) and fumaric acid (27.00 kg). The mixture was heated to 45° C. for 35 min and the resulting solution filtered through a 0.2 μm cartridge. The filtrate was concentrated in vacuo at <45° C. to about 150 L. The solution temperature was adjusted to 40° C. and ethyl acetate (901.2 kg) was added over 4 h. The mixture was cooled to about 20° C. and the resulting slurry aged for 16 h, followed by cooling to 5° C. and aging for 1 h. The product was isolated by filtration and the cake washed with chilled ethyl acetate (150 kg). The product was dried at 40° C. to constant weight to provide 89.1 kg of CT1812 fumarate (97.3 A % (LC)). The product was recrystallized by dissolving it in ethanol (668.5 kg) at 75-80° C. The solution was cooled to 20-25° C. and aged for 1 h, followed by cooling to 5° C. for 2 h. The CT1812 fumarate was isolated by filtration and washed with chilled ethanol (133.6 kg). The product was dried in vacuo at 35-40° C. to constant weight to provide 81.55 kg 2-(t-butoxy)-4-(3-methyl-3-(5-(methylsulfonyl)isoindolin-2-yl)butyl)phenol mono-fumarate salt crystal form A (64% yield overall, 99.8 A % (LC) purity).

XRPD of form A is shown in FIG. 1. DSC and TGA of form A are shown in FIGS. 2 and 3, respectively. Form A has a melting peak at T onset of about 161.3° C. and an enthalpy of about 87 J/g. The peak temperature of melting is about 163.2° C. It shows about 0.3% weight loss at about 155° C. by TGA. The $^1$H-NMR confirmed the free base to fumarate was about 1:0.95, with no residual solvent. The water content was 0.2% by KF. FTIR was consistent with the mono fumarate as shown in FIG. 4.

Example 2: Preparation of 2-(t-butoxy)-4-(3-methyl-3-(5-(methylsulfonyl)isoindolin-2-yl)butyl) phenol hemi-fumarate dihydrate Salt Crystal Form E 2-(t-butoxy)-4-(3-methyl-3-(5-(methylsulfonyl)isoindolin-2-yl)butyl)phenol hemi-fumarate dihydrate salt crystal form E was obtained from crystal form A by equilibration experiments in water, EtOH/water, acetone/water, ACN/water and slow evaporation experiments in EtOH, MEK and IPA. In addition, form A was also obtained from 2-(t-butoxy)-4-(3-methyl-3-(5-(methylsulfonyl)isoindolin-2-yl) butyl)phenol as detailed below:

Method a, Equilibration at 25° C., Water

Figure 5:
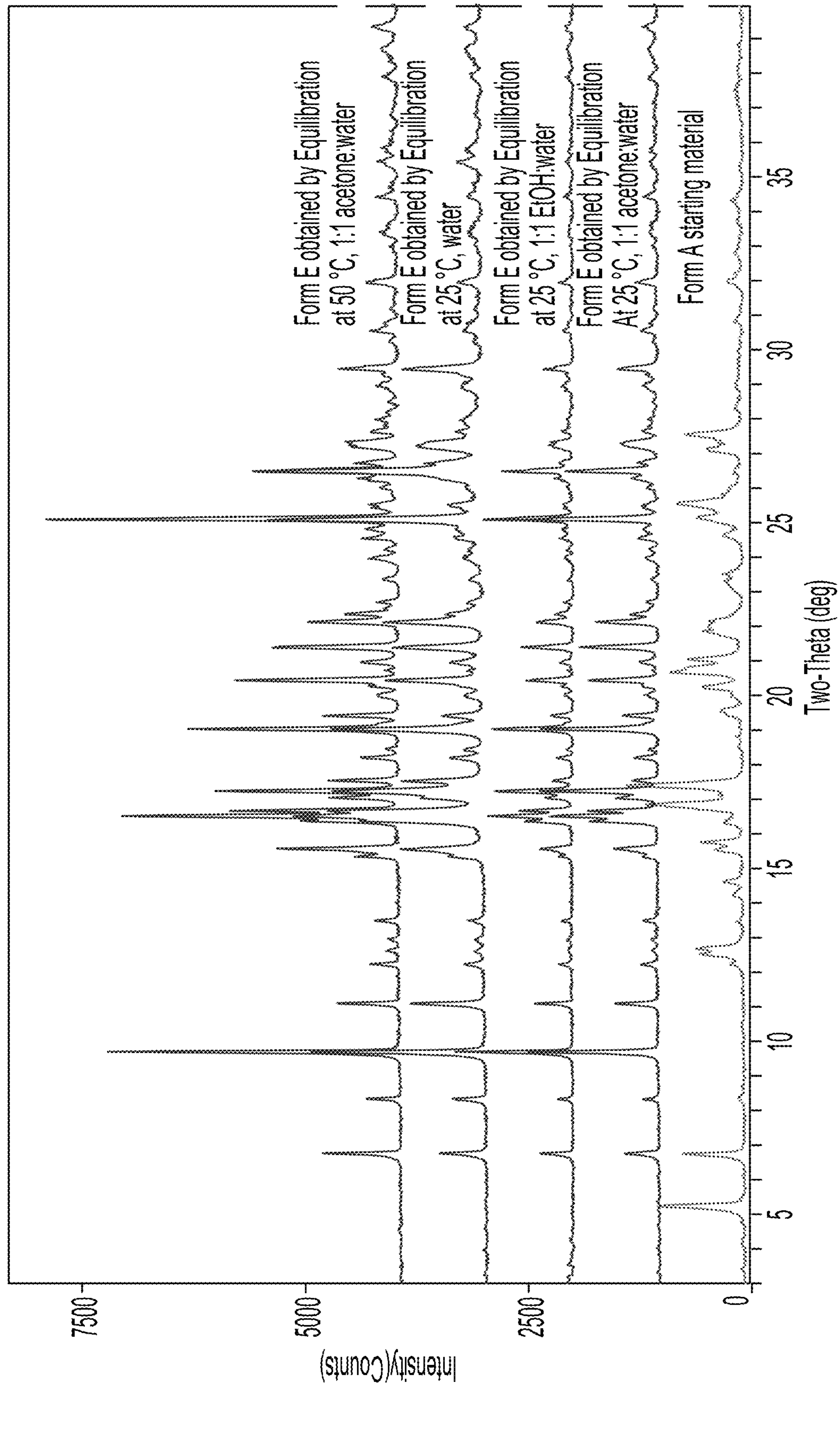
FIG. 5 is an X-ray powder diffraction pattern overlay of polymorphs obtained from equilibration of 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 50° C. in 1:1 acetone:water (V/V). The second from the top XRPD is of 2-(t-butoxy)-4-(3-methyl-3-(5-(methylsulfonyl)isoindolin-2-yl)butyl)phenol hemi-fumarate dihydrate, crystal form E obtained by equilibration at 25° C. in water. The third from the top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 25° C. in 1:1 EtOH:water (V/V). The second from the bottom XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 25° C. in 1:1 acetone:water (V/V). The bottom XRPD is 2-(t-butoxy)-4-(3-methyl-3-(5-(methylsulfonyl)isoindolin-2-yl)butyl)phenol mono-fumarate salt, crystal form A.

Approximately 50 mg of 2-(t-butoxy)-4-(3-methyl-3-(5-(methylsulfonyl)-isoindoline-2-yl)butyl)phenol mono-fumarate salt crystal form A was equilibrated in 63 mg/mL water at 25° C. for 1 week with a stirring plate. The solution was filtered to collect the solid which was analyzed by XRPD as shown in FIG. 5. The XRPD pattern was identified as form E.

Method B, Equilibration at 25° C., 1:1 EtOH:Water

Approximately 50 mg of 2-(t-butoxy)-4-(3-methyl-3-(5-(methylsulfonyl)isoindolin-2-yl)butyl)phenol mono-fumarate salt crystal form A was equilibrated in 61 mg/mL ethanol/water (1:1, V/V) at 25° C. for 1 week with a stirring plate. The solution was filtered to collect the solid which was analyzed by XRPD as shown in FIG. 5. The XRPD pattern was identified as form E.

Method C, Equilibration at 25° C., 1:1 Acetone:Water

Approximately 50 mg of 2-(t-butoxy)-4-(3-methyl-3-(5-(methylsulfonyl)isoindolin-2-yl)butyl)phenol mono-fumarate salt crystal form A was equilibrated in 63 mg/mL acetone/water (1:1, V/V) at 25° C. for 1 week with a stirring plate. The solution was filtered to collect the solid which was analyzed by XRPD as shown in FIG. 5. The XRPD pattern was identified as form E. NMR of the solid obtained in this experiment showed a ratio of free base to fumaric acid of 1:0.48.

Method D, Equilibration at 50° C., Water

Figure 6:
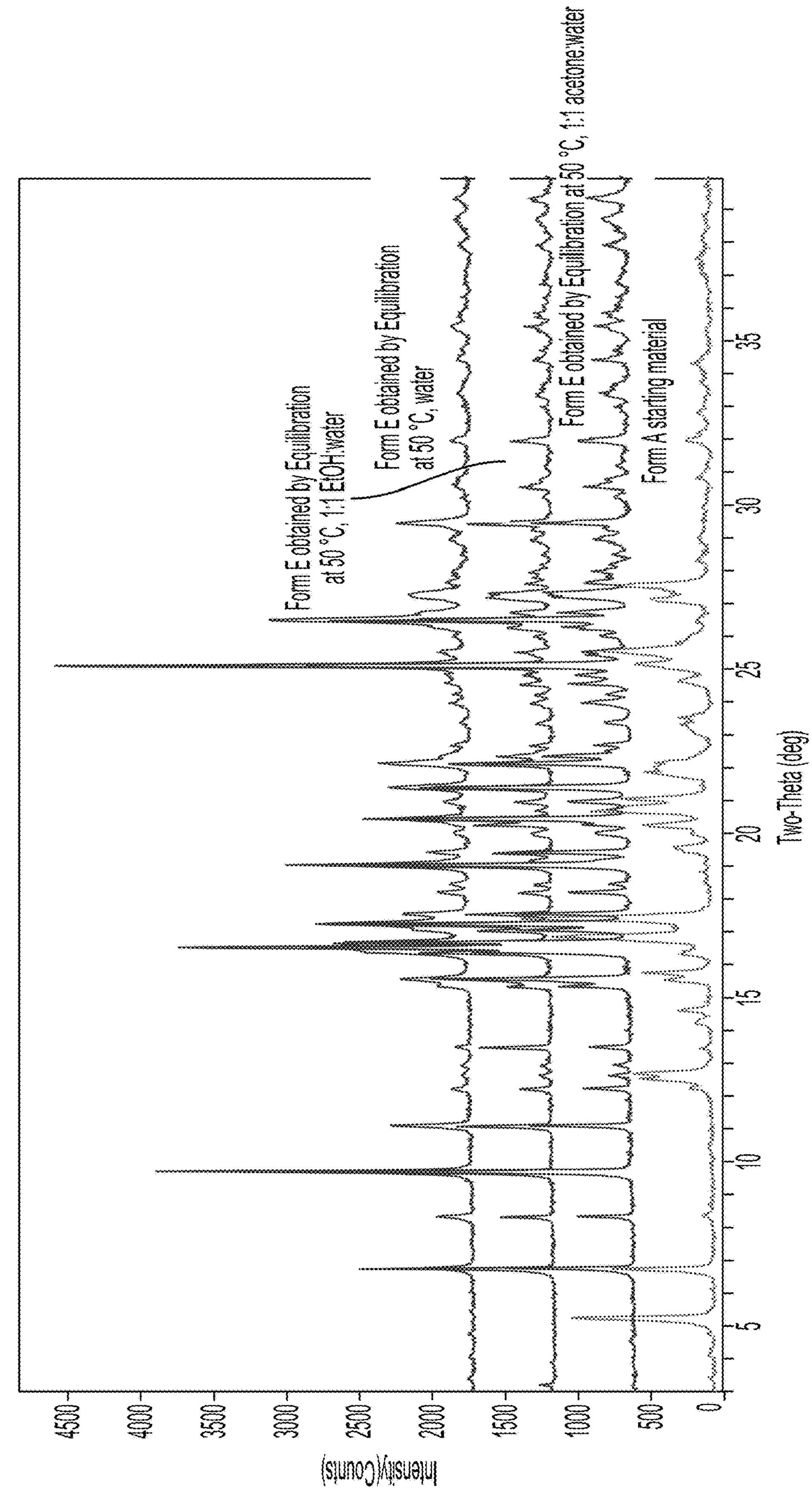
FIG. 6 is an X-ray powder diffraction pattern overlay of polymorphs obtained from equilibration of 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 50° C. in water. The second from the top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 50° C. in 1:1 EtOH:water (V/V). The second from the bottom XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 50° C. in 1:1 acetone:water (V/V). The bottom XRPD is 2-(t-butoxy)-4-(3-methyl-3-(5-(methylsulfonyl)isoindolin-2-yl)butyl)phenol mono-fumarate salt, crystal form A.

Approximately 50 mg of 2-(t-butoxy)-4-(3-methyl-3-(5-(methylsulfonyl)isoindolin-2-yl)butyl)phenol mono-fumarate salt crystal form A was equilibrated in 63 mg/mL water at 50° C. for 4 days with a stirring plate. The solution was filtered to collect the solid which was analyzed by XRPD as shown in FIG. 6. The XRPD pattern was identified as form E.

Method E, Equilibration at 50° C., 1:1 EtOH:Water

Approximately 50 mg of 2-(t-butoxy)-4-(3-methyl-3-(5-(methylsulfonyl)isoindolin-2-yl)butyl)phenol mono-fumarate salt crystal form A was equilibrated in 104 mg/mL ethanol/water (1:1, V/V) at 50° C. for 4 days with a stirring plate. The solution was filtered to collect the solid which was analyzed by XRPD as shown in FIG. 6. The XRPD pattern was identified as form E. NMR of the solid obtained in this experiment showed a ratio of free base to fumaric acid of 1:0.47. Water content was 6.7% by Karl Fischer.

Method F, Equilibration at 50° C., 1:1 Acetone:Water

Approximately 50 mg of 2-(t-butoxy)-4-(3-methyl-3-(5-(methylsulfonyl)isoindolin-2-yl)butyl)phenol mono-fumarate salt crystal form A was equilibrated in 250 mg/mL acetone/water (1:1, V/V) at 50° C. for 4 days with a stirring plate. The solution was filtered to collect the solid which was analyzed by XRPD as shown in FIG. 6. The XRPD pattern was identified as form E.

Method G, Slow Evaporation RT, EtOH

Figure 7:
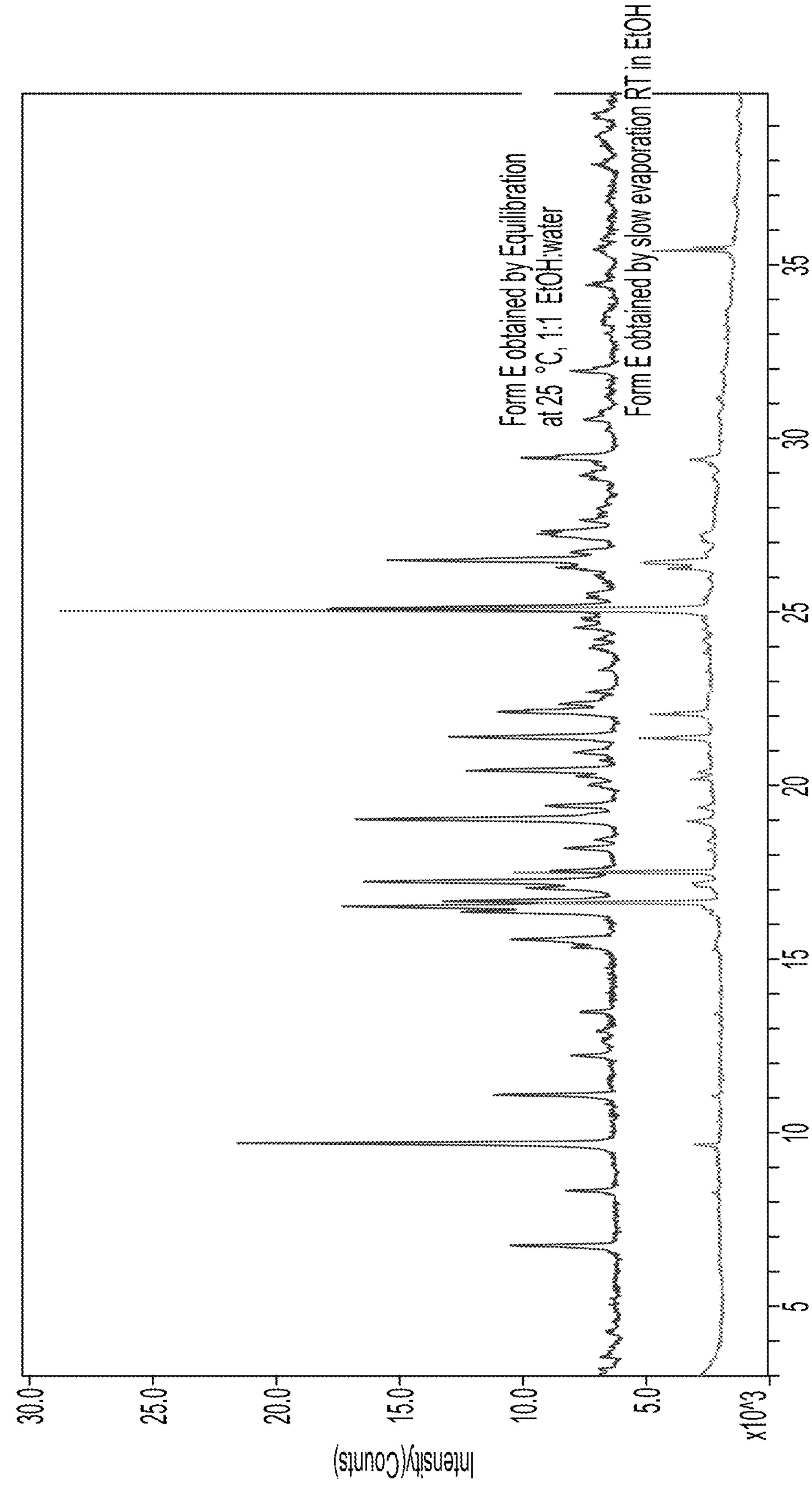
FIG. 7 is an X-ray powder diffraction pattern overlay of polymorphs obtained from 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 25° C. in 1:1 EtOH:water (V/N). The bottom XRPD is 2-(t-butoxy)-4-(3-methyl-3-(5-(methylsulfonyl)isoindolin-2-yl)butyl)phenol hemi-fumarate dihydrate salt, crystal form E obtained by slow evaporation at room temperature in EtOH.

Approximately 5 mg of 2-(t-butoxy)-4-(3-methyl-3-(5-(methylsulfonyl)-isoindolin-2-yl)butyl)phenol mono-fumarate salt crystal form A was suspended in 20 μL of ethanol. The solution was filtered through a 0.45 μm nylon filter and the filtrate (approximately 9 mg/mL) was allowed to evaporate under ambient conditions. The solid obtained after evaporation was in the form of crystals which were analyzed by XRPD, as shown in FIG. 7. The XRPD was identified as form E.

Method H, Slow Evaporation RT, MEK

Figure 8:
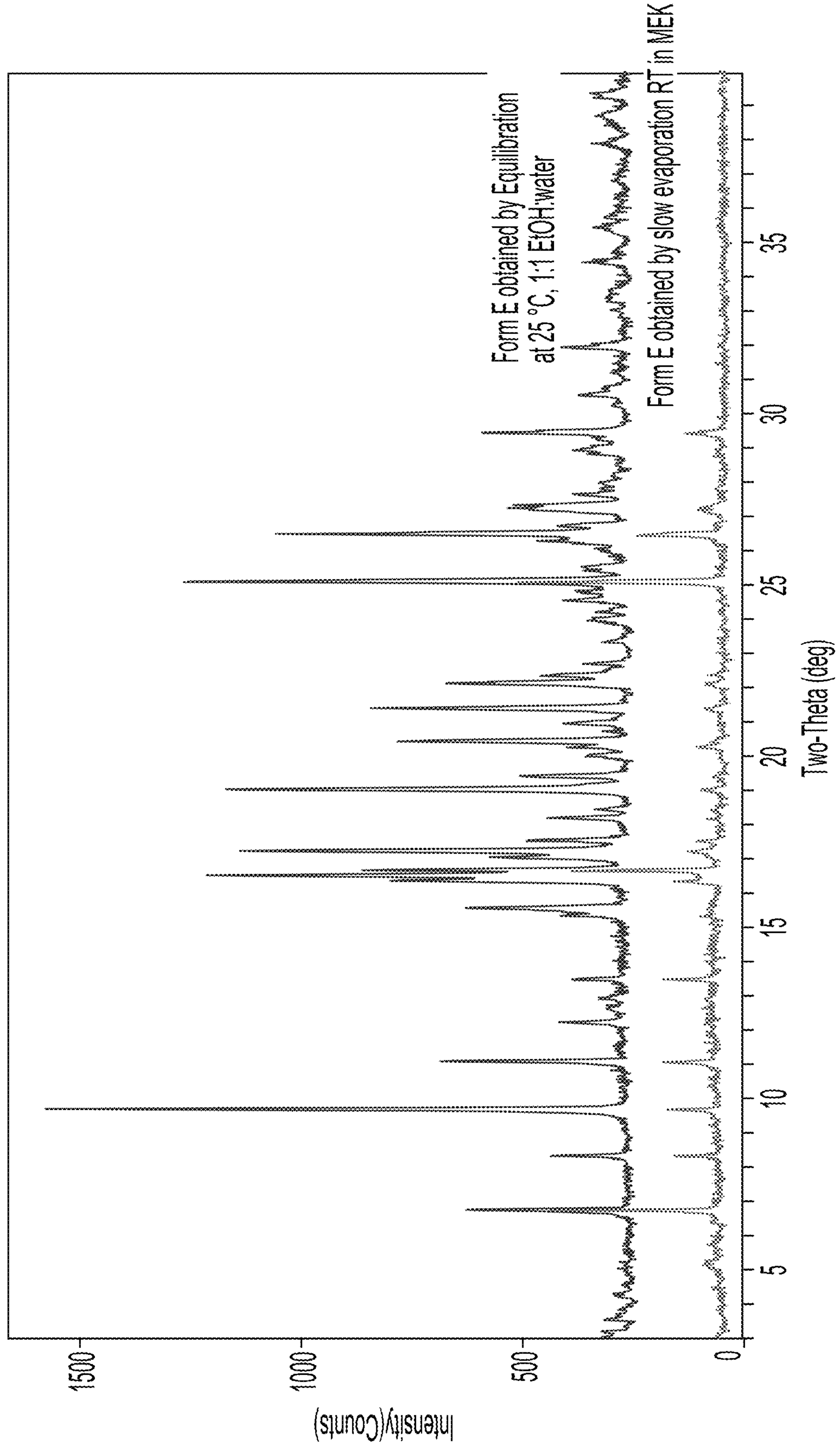
FIG. 8 is an X-ray powder diffraction pattern overlay of polymorphs obtained from 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 25° C. in 1:1 EtOH:water (V/N). The bottom XRPD is 2-(t-butoxy)-4-(3-methyl-3-(5-(methylsulfonyl)isoindolin-2-yl)butyl)phenol hemi-fumarate dihydrate salt, crystal form E obtained by slow evaporation at room temperature in MEK.

Approximately 5 mg of 2-(t-butoxy)-4-(3-methyl-3-(5-(methylsulfonyl)isoindolin-2-yl)butyl)phenol mono-fumarate salt crystal form A was suspended in 20 μL of methyl ethyl ketone. The solution was filtered through a 0.45 μm nylon filter and the filtrate (approximately 7 mg/mL) was allowed to evaporate under ambient conditions. The solid obtained after evaporation was in the form of irregular particles which were analyzed by XRPD, as shown in FIG. 8. The XRPD was identified as form E.

Method I, Slow Evaporation RT, 2-propanol

Figure 9:
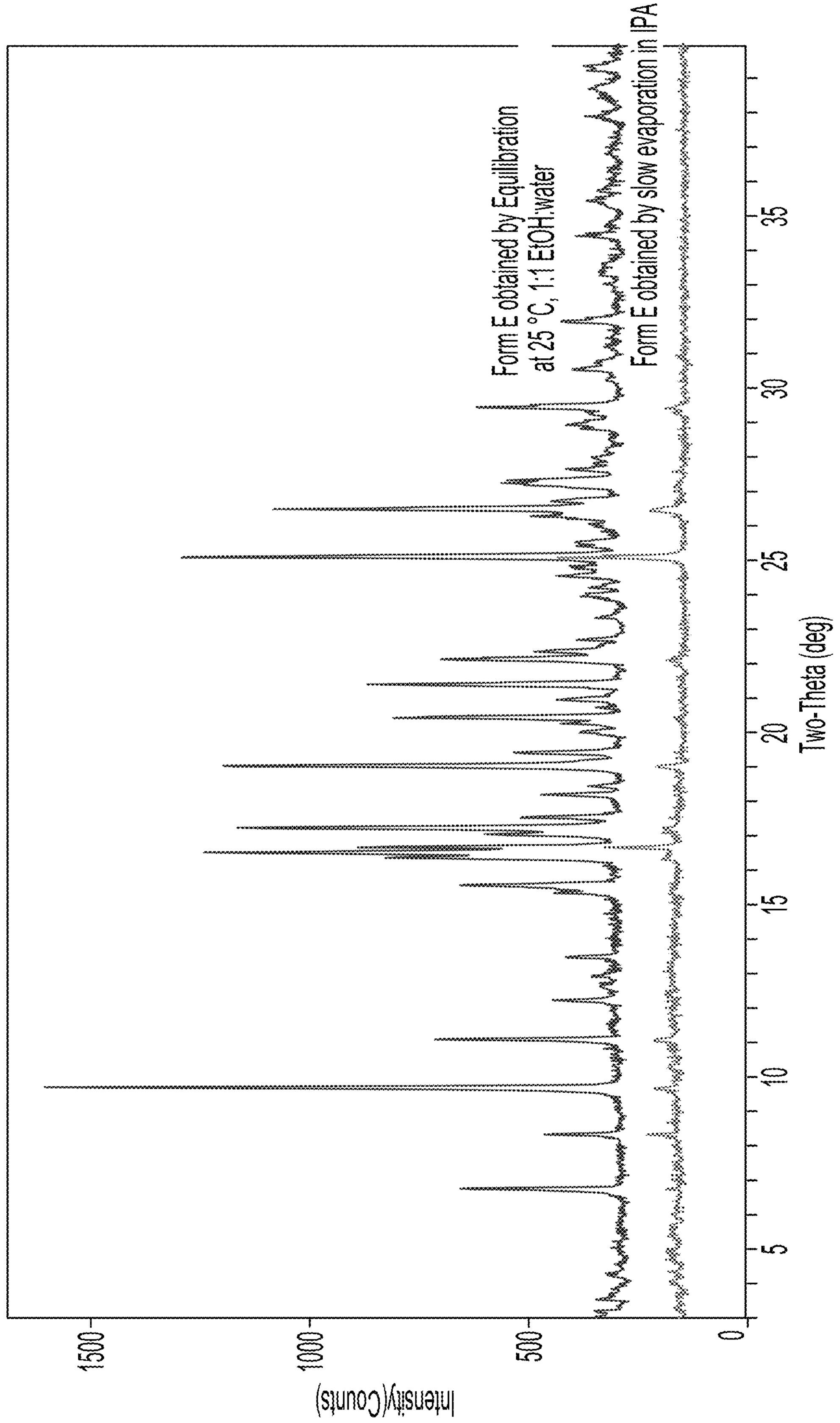
FIG. 9 is an X-ray powder diffraction pattern overlay of polymorphs obtained from 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol hemi-fumarate dihydrate salt, crystal form E obtained by equilibration at 25° C. in 1:1 EtOH:water (V/N). The bottom XRPD is 2-(t-butoxy)-4-(3-methyl-3-(5-(methylsulfonyl)isoindolin-2-yl)butyl)phenol hemi-fumarate dihydrate salt, crystal form E obtained by slow evaporation at room temperature in IPA.

Approximately 5 mg of 2-(t-butoxy)-4-(3-methyl-3-(5-(methylsulfonyl)isoindolin-2-yl)butyl)phenol mono-fumarate salt crystal form A was suspended in 20 μL of 2-propanol. The solution was filtered through a 0.45 μm nylon filter and the filtrate (approximately 5 mg/mL) was allowed to evaporate under ambient conditions. The solid obtained after evaporation was in the form of needle-like particles which were analyzed by XRPD, as shown in FIG. 9. The XRPD was identified as form E.

Method J, 700 mg Scale Up

About 700 mg of 2-(t-butoxy)-4-(3-methyl-3-(5-(methylsulfonyl)isoindolin-2-yl)butyl)phenol mono-fumarate salt crystal form A was equilibrated in 10 mL of ethanol/water (1:1, V/V) with magnetic stirring at 50° C. for about 6 hours. The solution was then cooled to 25° C. naturally and stirred at 25° C. for 46 hours. The obtained suspension was placed into a freezer at 5° C. for about 2 days. A precipitate formed and was filtered and dried at room temperature for about 22 hours. 495.6 mg of white solids in the form of irregular particles were obtained in 70.8% yield. Chemical purity was found to be 99.9% by HPLC. XRPD analysis identified the solid as form E as shown in FIG. 10. DSC showed a broad dehydration peak at T onset of about 90.8° C. with an enthalpy of about 251 J/g. Since the enthalpy value is very high, the dehydration should be complexed with melting of the salt. (FIG. 11). TGA showed a mass loss of about 7.0% at about 150.0° C. as shown in FIG. 12. NMR showed the ratio of free base to fumaric acid was 1:0.51, and water content was 6.9% by Karl Fischer.

Method K, Preparation from 2-(t-butoxy)-4-(3-methyl-3-(5-(methylsulfonyl)isoindolin-2-yl)butyl)phenol (Free Base)

Ethanol (429 kg), 2-(t-butoxy)-4-(3-methyl-3-(5-(methylsulfonyl)isoindolin-2-yl)butyl)phenol (free base 86.3 assay kg; 200.0 moles, 1.0 equiv., 93 A %) and fumaric acid (11.61 kg, 100.0 moles, 0.50 equiv.) were combined at RT. The mixture was warmed to 55° C. and aged for 30 min to dissolve the solids. The resulting solution was clarified through a 0.2 μm cartridge, and the vessel and filter were rinsed with warm EtOH (61.3 kg). The filtrate temperature was re-adjusted to 50° C., and water (69.0 kg) was added over 1 h followed by seed crystals (0.86 kg). The resulting slurry was aged for 90 min at 50° C. followed by cooling to 20° C. over 11 h. The slurry was aged for 3 h, filtered, and the cake was washed with cold (5° C.) aq. EtOH (140 kg; 9:1 wt/wt EtOH/water). The wet cake was dried in vacuo at 30° C. to constant weight to provide 2-(t-butoxy)-4-(3-methyl-3-(5-(methylsulfonyl)isoindolin-2-yl)butyl)phenol hemi-fumarate dihydrate salt crystal form E (94.1 kg) in 88% assay yield (99.7 A %). Unlike the preparation of Form A, high purity was obtained without the need for recrystallization. This is a preferred method for making form E. DSC: 115.7° C. (peak, FIG. 41). $^{1}H$ NMR (400 MHz, DMSO-$d_6$): δ 7.81 (d, J=1.65 Hz, 1H), 7.78 (dd, J=1.65, 7.78 Hz, 111), 7.51 (d, J=7.78 Hz, 1H), 6.78-6.72 (m, 3H), 6.62 (s, LH), 4.09 (hr s, 4H), 3.18 (s, 3H), 2.51 (m, 2H), 1.70-1.64 (hr in, 2H), 1.29 (s, 9H), 1.12 (s, 6H) ppm. $^{13}C$ NMR (101 MHz, DMSO-$d_6$): δ 166.7, 149.6, 146.3, 142.6, 141.5, 139.9, 134.6, 133.5, 126.2, 125.5, 124.1, 123.8, 121.6, 116.6, 79.4, 55.4, 51.6, 51.4, 44.3, 43.3, 29.4, 28.9, 22.8 ppm. Elem. anal. for $C_{26}H_{39}NO_8S$: calc.: H=59.36, H=7.42, N=2.67, S=6.10; found: H=59.58, H=7.59, N=2.61, S=6.21.

For this process the following procedures were used:

XRPD Method

XRPD was performed as follows:

Apparatus and Configuration

| Items | Configuration | |
|---|---|---|
| Diffractometer | Bruker D8 Focus | Bruker D8 Advance |
| Vertical goniometer | Theta/2 theta | Theta-theta |
| Sample stage | Rotating | Rotating |
| Filter | Nickel $K_\beta$ filter | N/A |
| Detector | LYNXEYE detector | LYNXEYE_XE-T(1D mode)/XE-T (1D mode) |

Diffraction Conditions are Described in Below

| | Configuration | |
|---|---|---|
| Items | Bruker D8 Focus | Bruker D8 Advance |
| X-ray Generator | Cu, Kα (□ = 1.54056Å) | Cu Kα (□ = 1.54060Å) |
| Tube Voltage | 40 KV | 40 KV |
| Tube Current | 40 mA | 40 mA. |
| Monochromator | Fixed Monochromator | Fixed Monochromator |
| Scan type | Coupled | Coupled Two Theta/Theta |
| Scan mode | Continuous | Continuous PSD fast |
| Scan range | 3°-42°or other range required 2θ using Cu Ka radiation | 3°-42° or other range required 2θ using Cu Ka radiation |
| Scan step | 0.02° or other value required | 0.02° or other value required |
| Step time | 0.2 s or other value required | 0.2 s or other value required |
| Sample stage rotating rate | 15 r/min* | 15 r/min or other value required |

*The stage rotating rate is fixed at 15 r/min, can't be adjusted.

DSC Method

DSC was performed on a Discovery DSC 25 or equivalent instrument using an Tzero aluminum pan. The mass of the sample was approximately 6.967 mg. A temperature range of 30 to 130° C. was evaluated with a heating rate of 10° C./min and 60 mL/min of nitrogen flow.

TGA Method

TGA was performed on a Discovery TGA5500 or equivalent as follows:

For TGA5500: A platinum sample pan was used and nitrogen flow was 50 mL/min to the sample. The mass of the sample was approximately 7.264 mg. Starting temperature was roughly ambient condition (below 35° C.) with a heating rate of 10° C./min. The final temperature was 300° C.

A sample of CT1812 hemi-fumarate dihydrate was analyzed by mass spectrometry to confirm the identity of the free base. Mass spectrometric analysis was performed by Linear Ion Trap Quadrupole Mass Spectrometer equipped with an electrospray ionization (ESI) source. Analysis was performed by a direct infusion of sample solution in 20:80 acetonitrile: water. The molecular ion of CT1812 was observed at 454.2 Da in positive ion mode and was consistent with [CT1812+Na]+. Calc. for $C_{24}H_{33}NO_4S$=431.21 amu.

Figure 19:
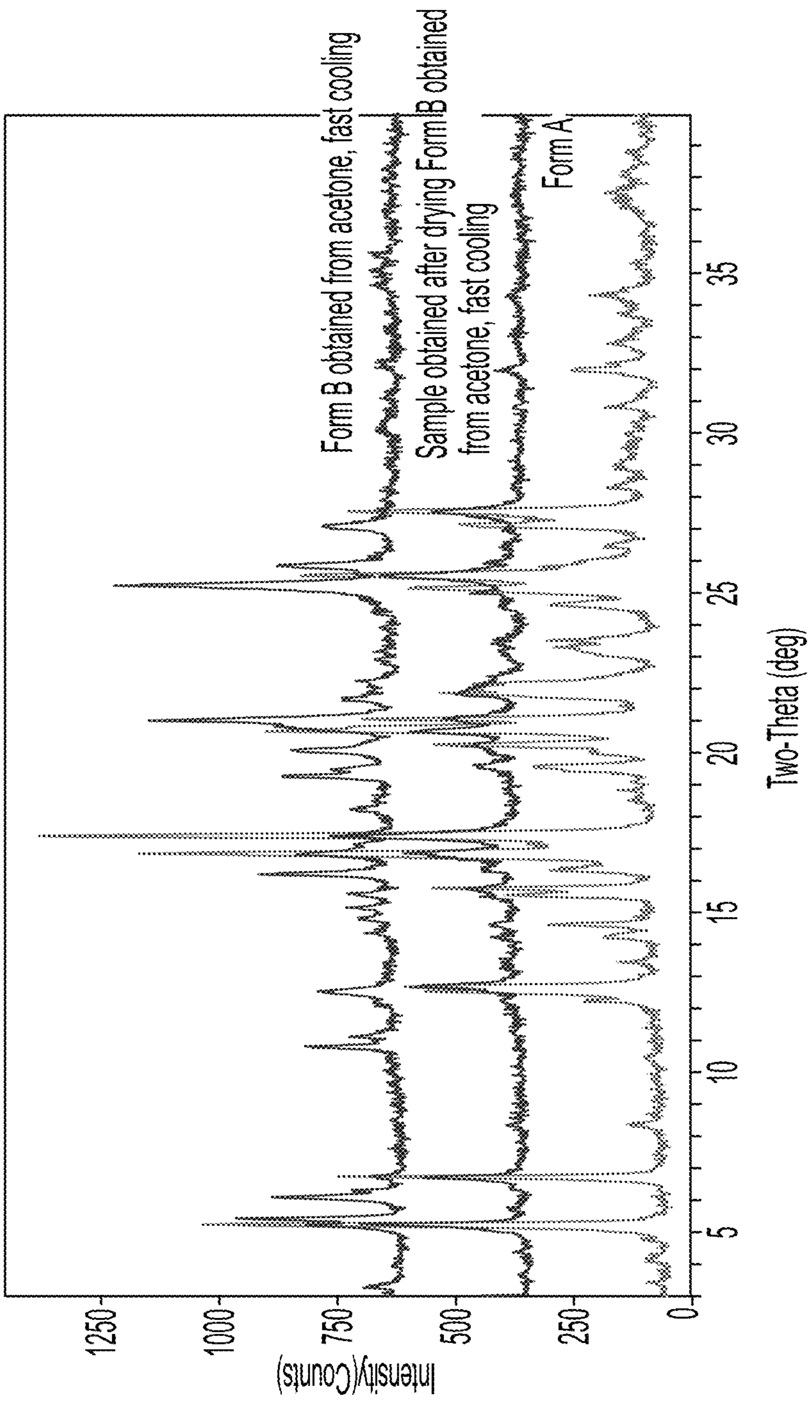
FIG. 19 is an XRPD overlay of 2-(t-butoxy)-4-(3-methyl-3-(5-(methylsulfonyl)isoindolin-2-yl)butyl)phenol mono-fumarate salt, crystal form A starting material (bottom XRPD), 2-(t-butoxy)-4-(3-methyl-3-(5-(methylsulfonyl)isoindolin-2-yl)butyl)phenol mono-fumarate salt, acetone solvate, crystal form B obtained from fast cooling in acetone (top XRPD) and a sample obtained after drying 2-(t-butoxy)-4-(3-methyl-3-(5-(methylsulfonyl)isoindolin-2-yl)butyl)phenol mono-fumarate salt, acetone solvate, crystal form B from fast cooling in acetone (middle XRPD).

Example 3: Preparation of 2-(t-butoxy)-4-(3-methyl-3-(5-(methylsulfonyl)isoindolin-2-yl)butyl) phenol mono-fumarate Salt, acetone Solvate Crystal Form B Method A Fast Cool, Acetone Approximately 50 mg 2-(t-butoxy)-4-(3-methyl-3-(5-(methylsulfonyl)isoindolin-2-yl)butyl)phenol mono-fumarate salt crystal form A was dissolved in acetone at a concentration of approximately 37 mg/mL at a temperature of 50° C. The resulting solution was placed into an ice bath and agitated, after which the precipitate was collected by filtration. The solid obtained was analyzed by XRPD as shown in FIG. 16 and the XRPD pattern was identified as 2-(t-butoxy)-4-(3-methyl-3-(5-(methylsulfonyl)isoindolin-2-yl)butyl)phenol mono-fumarate salt, acetone solvate crystal form B (top, middle). The solid was further analyzed by DSC and TGA as shown in FIGS. 17 and 18, respectively. The DSC showed multiple thermal events (including an endothermic peak at about 161.37° C.) and the TGA showed mass losses of 1.2% at about 42.0° C. followed by 2.1% at about 100.0° C. $^{1}H$ NMR showed the presence of 2.0% residual acetone. After drying the obtained solid at 50° C. for approximately 5 hours and analyzing by XRPD, the XRPD pattern corresponded to that of form A, as shown in FIG. 19.

Method B Slow Cool, Acetone

Figure 20:
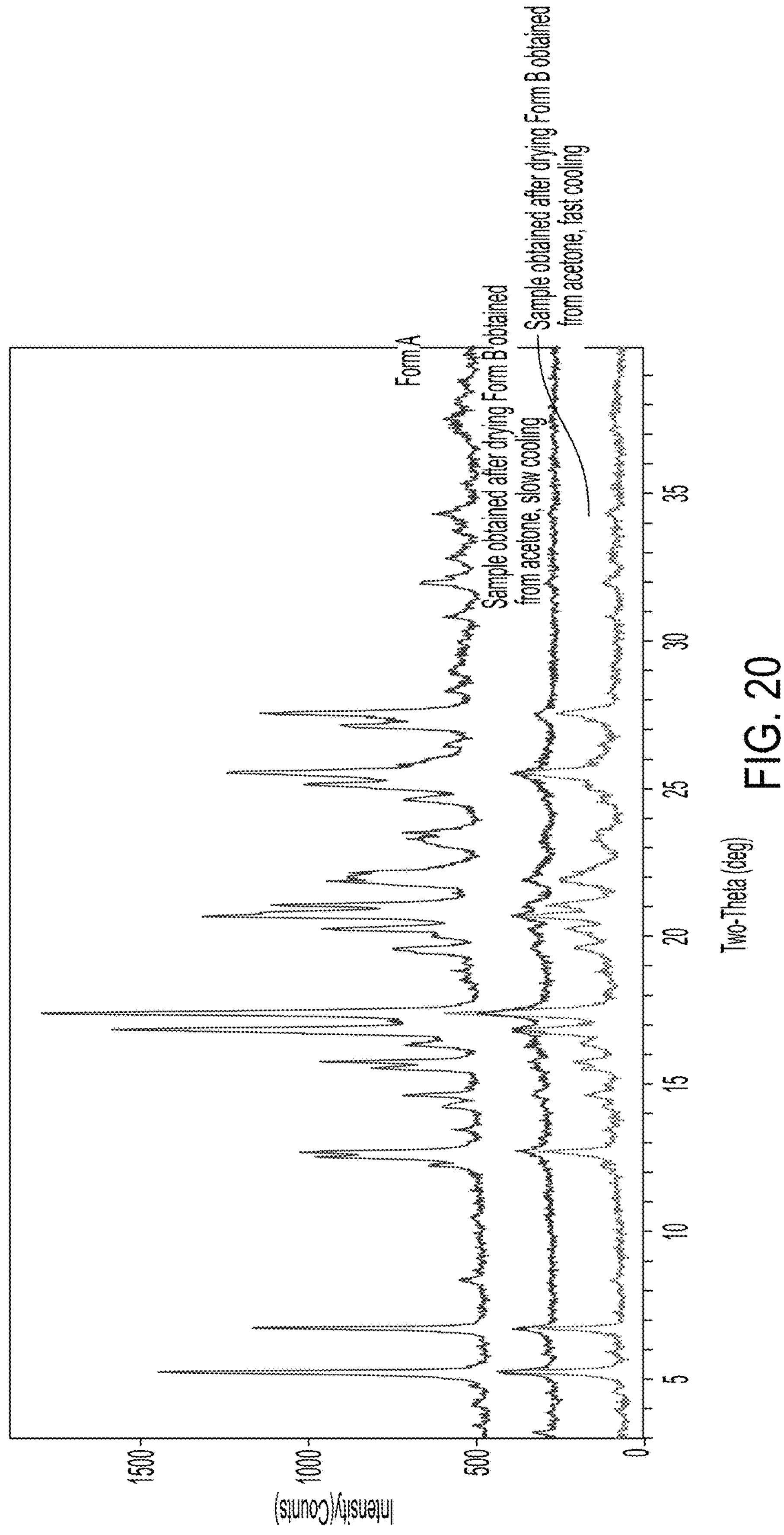
FIG. 20 is an XRPD overlay of 2-(t-butoxy)-4-(3-methyl-3-(5-(methylsulfonyl)isoindolin-2-yl)butyl)phenol mono-fumarate salt, crystal form A starting material (top XRPD); a sample obtained after drying 2-(t-butoxy)-4-(3-methyl-3-(5-(methylsulfonyl)isoindolin-2-yl)butyl)phenol mono-fumarate salt, acetone solvate, crystal form B from slow cooling in acetone (middle XRPD); and a sample obtained after drying 2-(t-butoxy)-4-(3-methyl-3-(5-(methylsulfonyl)isoindolin-2-yl)butyl)phenol mono-fumarate salt, acetone solvate, crystal form B from fast cooling in acetone (bottom XRPD).

Approximately 50 mg of 2-(t-butoxy)-4-(3-methyl-3-(5-(methylsulfonyl)isoindolin-2-yl)butyl)phenol mono-fumarate salt crystal form A was dissolved in acetone at a concentration of approximately 36 mg/mL at a temperature of 50° C. The resulting solution was cooled to 5° C. at a rate of 0.1° C./min and the precipitate was collected by filtration. The solid obtained was of low crystallinity and was analyzed by XRPD was shown to be that of 2-(t-butoxy)-4-(3-methyl-3-(5-(methylsulfonyl)isoindolin-2-yl)butyl)phenol mono-fumarate salt, acetone solvate crystal form B. The solids obtained from this experiment were dried at 50° C. for approximately 4 hours and reanalyzed by XRPD. The solid after drying appeared to be form A, FIG. 20.

Figure 21:
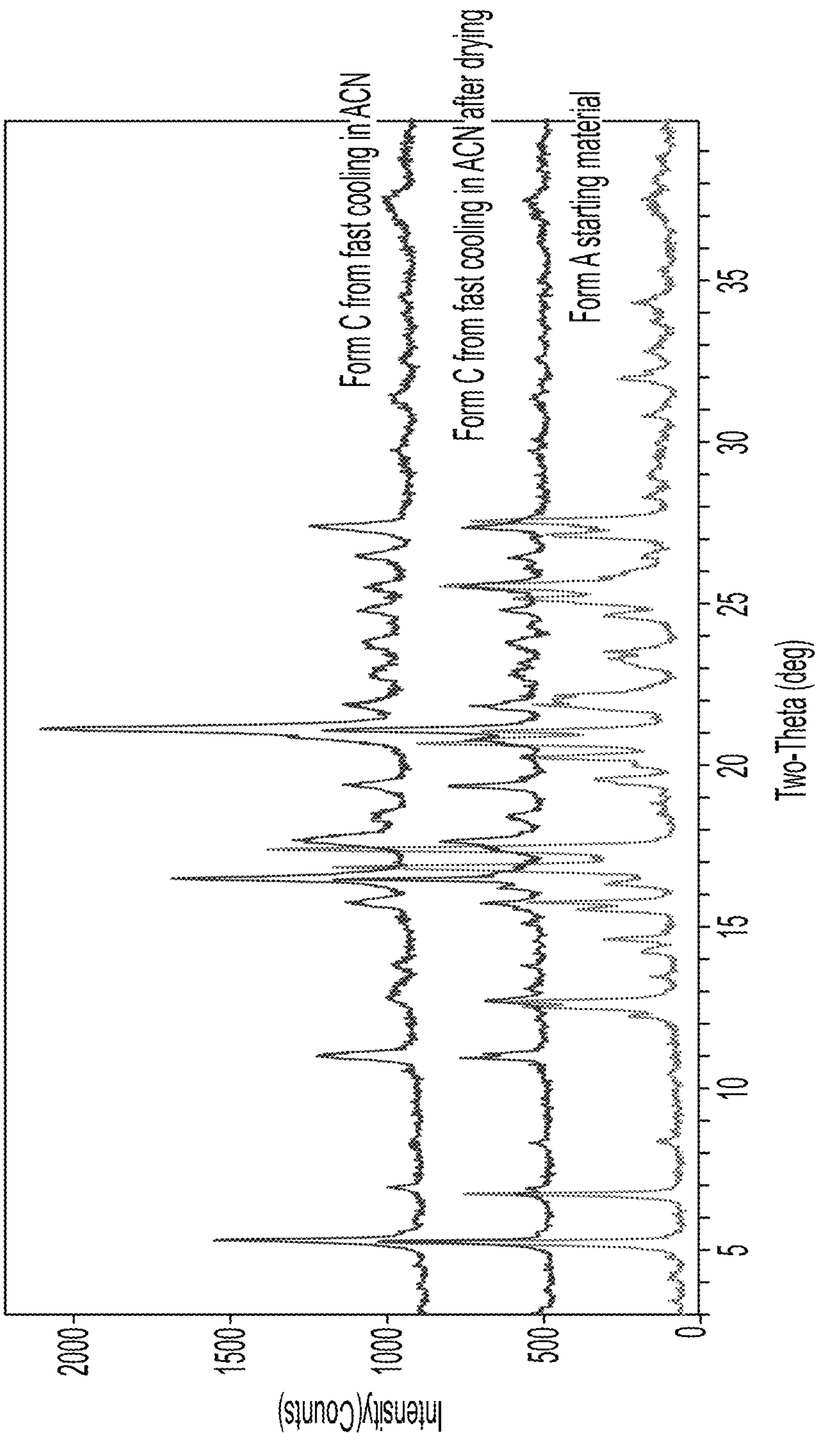
FIG. 21 is an X-ray powder diffraction pattern overlay of 2-(t-butoxy)-4-(3-methyl-3-(5-(methylsulfonyl)isoindolin-2-yl)butyl)phenol mono-fumarate salt, acetonitrile solvate, crystal form C obtained by fast cooling of 2-(t-butoxy)-4-(3-methyl-3-(5-(methylsulfonyl)isoindolin-2-yl)butyl)phenol mono-fumarate salt, crystal form A in ACN (top XRPD); a sample obtained after drying 2-(t-butoxy)-4-(3-methyl-3-(5-(methylsulfonyl)isoindolin-2-yl)butyl)phenol mono-fumarate salt, acetonitrile solvate, crystal form C obtained by fast cooling (middle XRPD); and 2-(t-butoxy)-4-(3-methyl-3-(5-(methylsulfonyl)isoindolin-2-yl)butyl)phenol mono-fumarate salt, crystal form A (bottom XRPD).

Example 4: Preparation of 2-(t-butoxy)-4-(3-methyl-3-(5-(methylsulfonyl)isoindolin-2-yl)butyl) phenol mono-fumarate Salt, acetonitrile Solvate Crystal Form C Method a, Fast Cool, Acetonitrile Approximately 50 mg of 2-(t-butoxy)-4-(3-methyl-3-(5-(methylsulfonyl)isoindolin-2-yl)butyl)phenol mono-fumarate salt crystal form A was dissolved in acetonitrile at a concentration of approximately 11 mg/mL at a temperature of 50° C. The resulting solution was placed into an ice bath and agitated, after which the precipitate was collected by filtration. The solid obtained was analyzed by XRPD as shown in FIG. 21 and the XRPD pattern was identified as form C. The solid was further analyzed by DSC and TGA as shown in FIGS. 22 and 23. The DSC showed two thermal events at about 101.2° C. (47.5 J/g) and about 157.3° C. (23.5 J/g), and the TGA showed a mass loss of about 3.0% at about 112.6° C. NMR of the solid obtained in this experiment showed 2.6% residual acetonitrile.

Method B Slow Evaporation, Acetonitrile

Approximately 5 mg of 2-(t-butoxy)-4-(3-methyl-3-(5-(methylsulfonyl)isoindolin-2-yl)butyl)phenol mono-fumarate salt crystal form A was suspended in 20 μL of acetonitrile. The solution was filtered through a 0.45 μm nylon filter and the filtrate was allowed to evaporate under ambient conditions. The solid obtained after evaporation was in the form of needle-like particles which were analyzed by XRPD, as shown in FIG. 24. The XRPD was identified as form C.

Example 5: Preparation of 2-(t-butoxy)-4-(3-methyl-3-(5-(methylsulfonyl)isoindolin-2-yl)butyl)phenol mono-fumarate Salt Crystal Form D Method A: Fast Cooling in Isopropyl Alcohol, 1 g Scale Approximately 1 g of 2-(t-butoxy)-4-(3-methyl-3-(5-(methylsulfonyl)isoindolin-2-yl)butyl)phenol mono-fumarate salt crystal form A was dissolved in 60 mL isopropyl alcohol while stirring at 50° C. The solution was filtered with a 0.45 μm nylon filter and the filtrate collected. The collected filtrate was placed in an ice bath and agitated for 3.5 hours, forming a precipitate. The precipitate was filtered and dried at room temperature for about 4.5 hours to yield 520.7 mg of a white solid (52.1% yield) in the form of irregularly shaped particles as observed by polarized light microscopy. The chemical purity of the solid was determined to be 99.6% by HPLC. The XPRD is shown in FIG. 25. The solid was further analyzed by DSC and TGA as shown in FIGS. 26 and 27, respectively. The DSC showed a melting onset at about 152.2° C. (97.3 J/g) and the TGA showed a mass loss of about 1.0% at about 145.0° C. $^{1}$H NMR of the solid obtained in this experiment showed 0.5% residual isopropyl alcohol. Water content was 1.2% by Karl Fisher.

Figure 28:
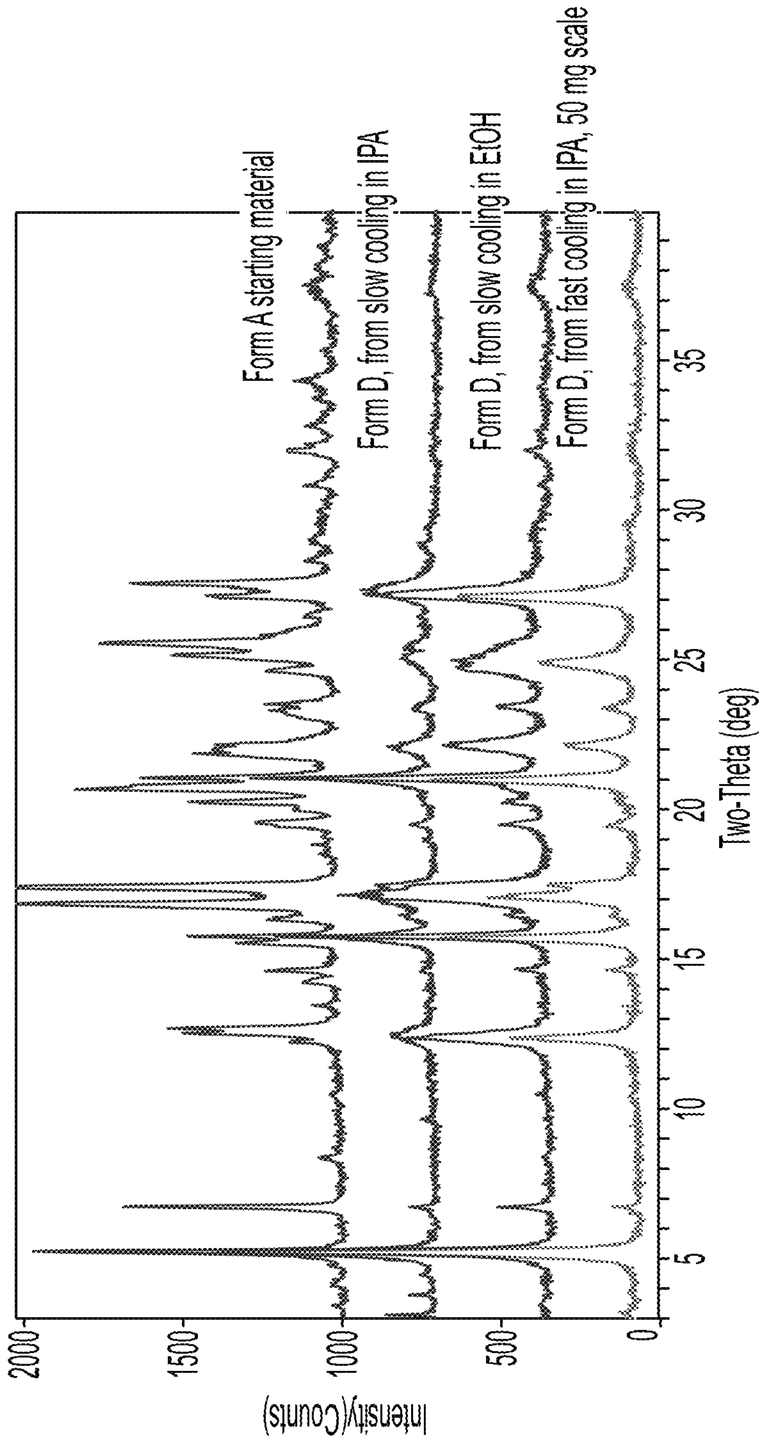
FIG. 28 is an X-ray powder diffraction pattern overlay of polymorphs obtained from 2-(t-butoxy)-4-(3-methyl-3-(5-(methylsulfonyl)isoindolin-2-yl)butyl)phenol mono-fumarate salt, crystal form A under various conditions. The top XRPD is of 2-(t-butoxy)-4-(3-methyl-3-(5-(methylsulfonyl)isoindolin-2-yl)butyl)phenol mono-fumarate salt, crystal form A. The second from the top XRPD is 2-(t-butoxy)-4-(3-methyl-3-(5-(methylsulfonyl)isoindolin-2-yl)butyl)phenol mono-fumarate salt, crystal form D obtained from slow cooling in IPA. The second from the bottom XRPD is 2-(t-butoxy)-4-(3-methyl-3-(5-(methylsulfonyl)isoindolin-2-yl)butyl)phenol mono-fumarate salt, crystal form D obtained from slow cooling in EtOH. The bottom XRPD is 2-(t-butoxy)-4-(3-methyl-3-(5-(methylsulfonyl)isoindolin-2-yl)butyl)phenol mono-fumarate salt, crystal form D obtained from fast cooling in IPA, 50 mg scale.

Form D was initially prepared by slow cooling in ethanol, slow cooling in 2-propanol and fast cooling in isopropyl alcohol on a smaller scale (50 mg). The XRPD of each of these is shown in FIG. 28.

Method B: Fast Cooling in Isopropyl Alcohol, 50 mg Scale

Approximately 50 mg of 2-(t-butoxy)-4-(3-methyl-3-(5-(methylsulfonyl)isoindolin-2-yl)butyl)phenol mono-fumarate salt crystal form A was dissolved in 2-propanol at a concentration of approximately 17 mg/mL at a temperature of 50° C. The resulting solution was placed into an ice bath and agitated, after which the precipitate was collected by filtration. The solid obtained was analyzed by XRPD as shown in FIG. 28 and the XRPD pattern was identified as form D.

Method C: Slow Cooling in EtOH

Approximately 50 mg of 2-(t-butoxy)-4-(3-methyl-3-(5-(methylsulfonyl)isoindolin-2-yl)butyl)phenol mono-fumarate salt crystal form A was dissolved in ethanol at a concentration of approximately 29 mg/mL at a temperature of 50° C. The resulting solution was cooled to 5° C. at a rate of 0.1° C./min and the precipitate was collected by filtration. The solid obtained was analyzed by XRPD as shown in FIG. 28. The XRPD pattern was identified as Form D Method D: Slow Cooling in 2-propanol Approximately 50 mg of 2-(t-butoxy)-4-(3-methyl-3-(5-(methylsulfonyl)isoindolin-2-yl)butyl)phenol mono-fumarate salt crystal form A was dissolved in 2-propanol at a concentration of approximately 17 mg/mL at a temperature of 50° C. The resulting solution was cooled to 5° C. at a rate of 0.1° C./min and the precipitate was collected by filtration. The solid obtained was analyzed by XRPD as shown in FIG. 28. The XRPD pattern was identified as form D.

Example 6: Preparation of 2-(t-butoxy)-4-(3-methyl-3-(5-(methylsulfonyl)isoindolin-2-yl)butyl)phenol mono-fumarate Salt, hemi-hydrate Crystal Form F Approximately 1 g of 2-(t-butoxy)-4-(3-methyl-3-(5-(methylsulfonyl)-isoindolin-2-yl)butyl)phenol mono-fumarate salt crystal form A was dissolved in 15 mL of ethanol while stirring at 25° C. for approximately 54 hours. After stirring, the precipitate was filtered and dried at room temperature for about 64 hours to yield 783.0 mg of a white solid (78.3% yield) in the form of irregularly shaped particles as observed by polarized light microscopy. The chemical purity of the solid was determined to be 99.7% by HPLC. The XPRD pattern was confirmed to be form F, as shown in FIG. 29. The solid was further analyzed by DSC and TGA as shown in FIGS. 30 and 31, respectively. The DSC exhibits a very low dehydration onset of about 17.4° C. and an enthalpy of about 13 J/g, followed by a melting onset at about 160.6° C. (enthalpy of about 100.4 J/g). The TGA showed a mass loss of about 1.6% at about 150.0° C. $^{1}$H NMR of the solid obtained in this experiment showed 0.6% residual ethanol. Water content was 1.6% by Karl Fisher.

2-(t-butoxy)-4-(3-methyl-3-(5-(methylsulfonyl)isoindolin-2-yl)butyl)phenol mono-fumarate salt, hemi-hydrate crystal form F was also obtained by equilibration at 25° C. in methanol, equilibration at 25° C. in ethanol, equilibration at 25° C. in isopropyl acetate, equilibration at 25° C. in acetone, equilibration at 25° C. in MTBE, equilibration at 25° C. in THF, equilibration at 25° C. in DCM, equilibration at 25° C. in ACN, equilibration at 25° C. in EtOAc, equilibration at 25° C. in MEK, equilibration at 25° C. in toluene, equilibration at 25° C. in 2-propanol, equilibration at 25° C. in heptane, equilibration at 50° C. in ethanol, equilibration at 50° C. in isopropyl acetate, equilibration at 50° C. in ACN, equilibration at 50° C. in toluene, equilibration at 50° C. in 2-propanol, equilibration at 50° C. in heptane, and slow evaporation at room temperature in acetone.

2-(t-butoxy)-4-(3-methyl-3-(5-(methylsulfonyl)isoindolin-2-yl)butyl)phenol mono-fumarate salt, hemi-hydrate crystal form F was identified to be the isostructural to crystal form A but in a hydration state. XRPD patterns of crystal form A and crystal form F are very similar except for slight shifts of several peaks, due to enclosed water.

Example 7: Preparation of 2-(t-butoxy)-4-(3-methyl-3-(5-(methylsulfonyl)isoindolin-2-yl)butyl)phenol mono-fumarate Salt, methanol solvate Crystal Form G Approximately 5 mg of 2-(t-butoxy)-4-(3-methyl-3-(5-(methylsulfonyl)isoindolin-2-yl)butyl)phenol mono-fumarate salt crystal form A was suspended in 20 μL of methanol. The solution was filtered through a 0.45 μm nylon filter and the filtrate was allowed to evaporate under ambient conditions. The solid obtained after evaporation was in the form of needle-like particles which were analyzed by XRPD, as shown in FIG. 32. The XRPD was identified as form G. $^{1}$H NMR of the solid obtained in this experiment showed 2.7% residual methanol.

Example 8: Effect of humidity on 2-(t-butoxy)-4-(3-methyl-3-(5-(methylsulfonyl)isoindolin-2-yl) butyl)phenol mono-fumarate Salt Crystal Form A and 2-(t-butoxy)-4-(3-methyl-3-(5-(methylsulfonyl) isoindolin-2-yl)butyl)phenol mono-fumarate Salt, hemi-hydrate Crystal Form F Water sorption and desorption behavior was investigated by humidity control XRPD with two cycles of 60% RH (initial) –90% RH (6 h) –40% RH (6 h) –30% RH (6 h) –0% RH (6 h); 0% RH (40 h) and 40% RH (6 h) –40% RH (12 h) –60% RH (6 h). Results are shown in Table 8 and FIGS. 33-35.

TABLE 8

Humidity Control XRPD

| Humidity cycle | Humidity/ holding time | XRPD |
|---|---|---|
| 60% RH→90% RH→ | 60% RH (initial) | Crystal form F |
| 40% RH→30% RH→ | 90% RH (6 h) | Crystal form F |
| 0% RH→40% RH→ | 40% RH (6 h) | Crystal form A |
| 60% RH | 30% RH (6 h) | Crystal form A |
| | 0% RH (6 h) | Crystal form A |
| | 0% RH (40 h) | Crystal form A |
| | 40% RH (6 h) | Crystal form A |
| | 40% RH (12 h) | Crystal form A |
| | 60% RH (6 h) | Crystal form F |

Crystal form F starts to lose water when humidity is below 40%, and it takes some time to completely dehydrate (more than 6 h) at 30% RH. Crystal form A is the dehydration product of crystal form F according to variable humidity XRPD analysis (above). Crystal form A can absorb the water and convert back to crystal form F in above 40% RH quickly. The critical humidity of the two forms is around 40% RH from DVS results. In high humidity, measured XRPD is always crystal form F regardless of whether the original sample is crystal form A or F, whereas in low humidity, measure XRPD is always crystal form A.

Example 9: Form E Stability

A 12-month stability study of 2-(t-butoxy)-4-(3-methyl-3-(5-(methylsulfonyl)isoindolin-2-yl)butyl)phenol hemi-fumarate dihydrate salt crystal form E was performed at 25° C./60% RH and 40° C./75% RH (6 months data as the accelerated condition). At designated time points the material was tested for appearance, purity by HPLC area % by the HPLC method described in Table 9, impurities, water content (theoretical=6.8 wt %) and form by XRPD. Results of the stability testing are described in Table 10.

TABLE 9

HPLC conditions used in stability testing
Column: Supelco Ascentis Express Phenyl-Hexyl, 150 × 4.6 mm, 2.7 μm. Cat#533353-U

| Flow rate: 1.0 mL/min | Time (min) | MPB (%) |
|---|---|---|
| MPA: 0.1% TFA in water | 0 | 20 |
| MPB: 0.1% TFA in MeCN | 12 | 50 |
| Injection vol. 5 μL | 25 | 95 |
| Wavelength: 220 nm | 30 | 95 |
| Column temperature: 25 °C | 30.1 | 20 |
| Concentration: 1.0 mg/mL | 35 | 20 |
| Diluent: water/MeCN 75/25 | | |

TABLE 10

Results of stability testing of 2-(t-butoxy)-4-(3-methyl-3-(5-(methylsulfonyl) isoindolin-2-yl)butyl)phenol hemi-fumarate dihydrate salt crystal form E

| | | | | | Impurities | | | | |
|---|---|---|---|---|---|---|---|---|---|
| Storage Conditions | Time point | Appearance | XRPD | Purity | RRT 1.08 | RRT 1.69 | RRT 2.02 | Total | Moisture (% w/w) |
| NA | T0 | white powder | Form E | 99.7% | 0.21% | | 0.08% | 0.29% | 6.81% |
| 25° C. 60% RH | 1 month | white powder | Form E | 99.7% | 0.21% | | 0.05% | 0.27% | 6.65% |
| | 3 months | white powder | Form E | 99.7% | 0.22% | | 0.06% | 0.28% | 7.03% |
| | 6 months | white powder | Form E | 99.7% | 0.21% | | 0.05% | 0.27% | 6.41% |
| | 9 months | white powder | Form E | 99.7% | 0.23% | | 0.06% | 0.29% | 7.16% |
| | 12 months | white powder | Form E | 99.8% | 0.24% | | <LOQ | 0.24% | 7.24% |
| 40° C. 75% RH | 1 month | white powder | Form E | 99.7% | 0.22% | | 0.06% | 0.28% | 6.87% |
| | 3 months | white powder | Form E | 99.7% | 0.26% | | 0.07% | 0.33% | 6.92% |
| | 6 months | white powder | Form E | 99.7% | 0.21% | | 0.04% | 0.25% | 6.87% |

No significant changes were observed over the duration of the study in any of the tested items. Suggesting the material is stable at 25° C./60% RH for 12 M and 40° C./75% RH for 6M.

This stands in contrast to the form A which shows impurity growth over time in most lots at 40° C./75% RH for 6 M (Table 11).

TABLE 11

Results of stability testing of 2-(t-butoxy)-4-(3-methyl-3-(5-(methylsulfonyl)isoindolin-2-yl)butyl)phenol mono-fumarate salt crystal form A

| Time point | Total Impurities |
|---|---|
| Lot A | |
| 0 | 0.06% |
| 1 month | 0.15% |
| 3 months | 0.23% |
| 6 months | 0.26% |
| Lot B | |
| 0 | 0.23% |
| 1 month | 0.36% |
| 3 months | 0.43% |
| 6 months | 0.53% |
| Lot C | |
| 0 | 0.10% |
| 1 month | 0.70% |
| 3 months | 1.1% |
| 6 months | 1.0% |

Due to the interconversion of crystal forms A and F and the stability of crystal from E, crystal form E is of particular importance as an API.

Example 10: Water Activity Studies at 25° C.

2-(t-butoxy)-4-(3-methyl-3-(5-(methylsulfonyl)isoindolin-2-yl)butyl)-phenol mono-fumarate salt crystal form A was equilibrated at 25° C. in ethanol with six different water. Results are shown in Table 12 and FIGS. 36-38.

TABLE 12

Water Activity at 25 °C

| Solvent/ Concentration (mg/mL) | Water activity | XRPD | Additional tests |
|---|---|---|---|
| Ethanol (63) | 0.0 | Crystal form F* (FIG. 36) | free form: fumaric acid = 1:0.96 ($^1$H NMR) |
| Ethanol/Water (97.0/3.0, v/v) (64) | 0.2 | Crystal form F (FIG. 36) | |
| Ethanol/Water (95.2/4.8, v/v) (64) | 0.3 | Mixture of crystal form F and crystal form E (FIG. 37) | free form: fumaric acid = 1:0.60 ($^1$H NMR) |
| Ethanol/Water (92.7/7.3, v/v) (63) | 0.4 | Crystal form E (FIG. 38) | free form: fumaric acid = 1:0.47 ($^1$H NMR) |
| Ethanol/Water (89.6/10.4, v/v) (64) | 0.5 | Crystal form E (FIG. 38) | |
| Ethanol/Water (80.2/19.8, v/v) (63) | 0.7 | Crystal form E (FIG. 38) | |
| Ethanol/Water (45.0/55.0, v/v) (64) | 0.9 | Crystal form E (FIG. 38) | |

*Ambient humidity about 80% RH

Example 11: Relative Form Stability Evaluation by Competitive Slurry Test

To assess the relative stability of crystal form A, crystal form F, and crystal form E in EtOH/water and IPA/water near the stability boundary conditions, a set of competitive slurry experiments was designed. Water activities in EtOH/water and IPA/water were chosen between 0.2-0.4.

Figure 39:
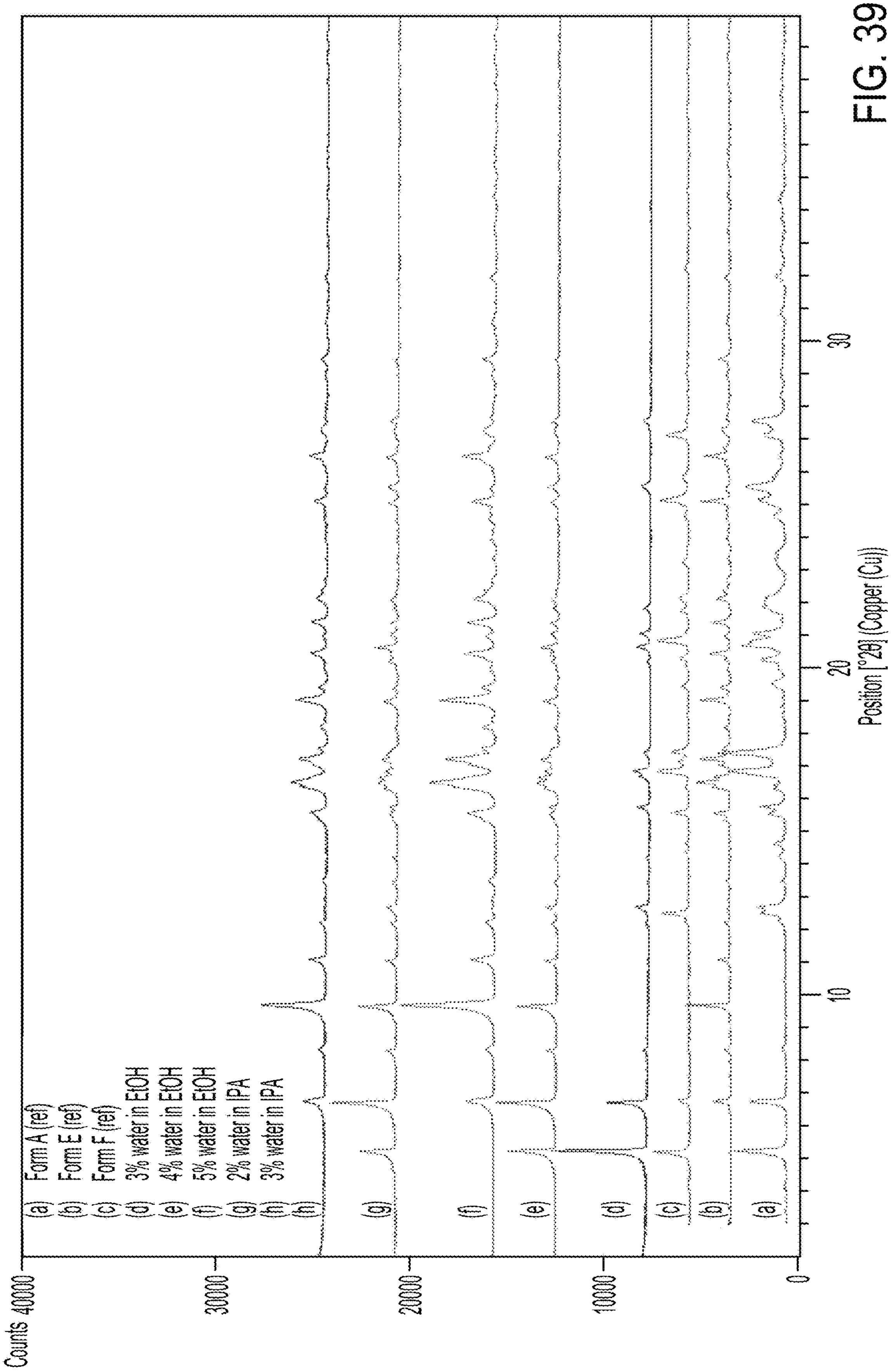
FIG. 39 is an XRPD overlay of samples of a competitive slurry experiment of crystal forms A, E and F in water activities in EtOH/water and IPA/water. XRPD (a) is a reference XRPD of form A, XRPD (a) is a reference XRPD of form A, XRPD (b) is a reference XRPD of form E, (c) is the XRPD resulting from the competitive slurry in 3% water in EtOH, (d) is the XRPD resulting from the competitive slurry in 3% water in EtOH, (e) is the XRPD resulting from the competitive slurry in 4% water in EtOH, (f) is the XRPD resulting from the competitive slurry in 5% water in EtOH, (g) is the XRPD resulting from the competitive slurry in 2% water in IPA, (h) is the XRPD resulting from the competitive slurry in 3% water in IPA.

Equal amounts of crystal form A and crystal form E were added to a clean supernatant solution (5 mL) of each desired solvent (i.e. 3, 4, and 5 vol % water in EtOH, and 2 and 3 vol % water in IPA). Each resulting slurry was equilibrated at 20° C. for 24 h on a shaker at 500 rpm. The final wet solids were analyzed by PLM and XRPD. The results are presented in Table 13 and FIG. 39.

TABLE 13

Results of Competitive Slurry Experiment at 20 °C

| | Solvent | Ratio (v/v) | Water activity ($a_w$) | PLM (end slurry) | XRPD (final slurry) |
|---|---|---|---|---|---|
| 1 | EtOH/water | 97:3 | 0.28 | Needles only | A |
| 2 | | 96:4 | 0.34 | Needles + cubes | A + E |
| 3 | | 95:5 | 0.40 | Cubes only | E |
| 4 | IPA/water | 98:2 | 0.29 | Needles + cubes | A + E |
| 5 | | 97:3 | 0.40 | Cubic only | E |

It was observed that a) when $a_w \geq 4.0$, all crystal form A (or F) converted to crystal form E; b) when $0.3 \leq a_w \leq 0.4$, a mixture of crystal form A (or F) and crystal form E remained; and c) at $a_w = 0.28$ in EtOH, crystal form E converted to Pattern A (or F).

Crystal form E exhibits cubic morphology while crystal form A (or F) present as needles.

These results indicate that crystal Form A disproportionation to Form E in water or solutions with a water activity ($a_w$)>0.4.

The invention claimed is:

1. 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) comprising characteristic 2θ peaks at 9.69, 16.51, 17.23, 19.02, 25.10, and 26.49° (±0.2°).

2. The 2-(t-butoxy)-4-(3-methyl-3-(5-(methylsulfonyl)isoindolin-2-yl)butyl)phenol hemi-fumarate dihydrate salt crystal form E of claim 1, wherein the XRPD further comprises peaks at 6.75, 11.09, 15.56, 16.35, 16.67, 20.43, 21.39, and 22.12° (±0.2°).

3. The 2-(t-butoxy)-4-(3-methyl-3-(5-(methylsulfonyl)isoindolin-2-yl)butyl)phenol hemi-fumarate dihydrate salt crystal form E of claim 1, wherein the XRPD further comprises peaks at 17.04, 17.54, 19.41, and 29.45° (±0.2°).

4. The 2-(t-butoxy)-4-(3-methyl-3-(5-(methylsulfonyl)isoindolin-2-yl)butyl)phenol hemi-fumarate dihydrate salt crystal form E of claim 1, wherein the XRPD further comprises peaks at 15.34, 22.35, 26.71, 27.17, and 27.29° (±0.2°).

5. The 2-(t-butoxy)-4-(3-methyl-3-(5-(methylsulfonyl)isoindolin-2-yl)butyl)phenol hemi-fumarate dihydrate salt crystal form E of claim 1, wherein the XRPD comprises peaks at 6.75, 8.33, 9.69, 11.09, 12.22, 12.62, 12.93, 13.49, 15.34, 15.56, 16.35, 16.51, 16.67, 17.04, 17.23, 17.54, 18.19, 18.44, 19.02, 19.41, 20.00, 20.26, 20.43, 20.71, 20.97, 21.39, 22.12, 22.35, 22.68, 23.35, 23.95, 24.23, 24.55, 24.82, 25.10, 25.51, 26.02, 26.28, 26.49, 26.71, 27.17, 27.29, 27.64, 27.98, 28.49, 28.95, 29.45, 30.25, 30.54, 31.24, 31.95, 33.39, 34.40, 35.41, 35.82, 36.33, 36.75, 37.89, 38.72, and 39.30° (±0.2°).

6. The 2-(t-butoxy)-4-(3-methyl-3-(5-(methylsulfonyl)isoindolin-2-yl)butyl)phenol hemi-fumarate dihydrate salt crystal form E of claim 1, characterized by a differential scanning calorimetry (DSC) curve that comprises a broad dehydration peak at T onset of about 90.8° C.

7. The 2-(t-butoxy)-4-(3-methyl-3-(5-(methylsulfonyl)isoindolin-2-yl)butyl)phenol hemi-fumarate dihydrate salt crystal form E of claim 1, which has a polymorph purity of at least 90% form E.

8. The 2-(t-butoxy)-4-(3-methyl-3-(5-(methylsulfonyl) isoindolin-2-yl)butyl)phenol hemi-fumarate dihydrate salt crystal form E of claim 1, which has a polymorph purity of at least 95% form E.

9. The 2-(t-butoxy)-4-(3-methyl-3-(5-(methylsulfonyl) isoindolin-2-yl)butyl)phenol hemi-fumarate dihydrate salt crystal form E of claim 1, which has a polymorph purity of at least 97% form E.

10. The 2-(t-butoxy)-4-(3-methyl-3-(5-(methylsulfonyl) isoindolin-2-yl)butyl)phenol hemi-fumarate dihydrate salt crystal form E of claim 1, which has a polymorph purity of at least 99% form E.

11. The 2-(t-butoxy)-4-(3-methyl-3-(5-(methylsulfonyl) isoindolin-2-yl)butyl)phenol hemi-fumarate dihydrate salt crystal form E of claim 1, which has a chemical purity of at least 95 A %.

12. The 2-(t-butoxy)-4-(3-methyl-3-(5-(methylsulfonyl) isoindolin-2-yl)butyl)phenol hemi-fumarate dihydrate salt crystal form E of claim 1, which has a chemical purity of at least 97 A %.

13. The 2-(t-butoxy)-4-(3-methyl-3-(5-(methylsulfonyl) isoindolin-2-yl)butyl)phenol hemi-fumarate dihydrate salt crystal form E of claim 1, which has a chemical purity of at least 99 A %.

14. The 2-(t-butoxy)-4-(3-methyl-3-(5-(methylsulfonyl) isoindolin-2-yl)butyl)phenol hemi-fumarate dihydrate salt crystal form E of claim 1, which has a unit crystal that shows, in single-crystal analysis, the following crystal data:

| | |
|---|---|
| Crystal dimension (mm) | 0.15 × 0.12 × 0.08 |
| Temperature (K) | 170 |
| a (Å) | 32.5801(12) |
| b (Å) | 9.7212(4) |
| c (Å) | 21.2820(7) |
| α (°) | 90 |
| β (°) | 126.4700(10) |
| γ (°) | 90 |
| V (Å$^3$) | 5420.4(4) |
| Space Group | C2/c |
| Z | 8 |
| Chemical formula/ asymmetric unit | $C_{24}H_{34}NO_4S \cdot 0.5C_4H_2O_4 \cdot 2H_2O$ |
| Crystal density (g/cm$^3$) | 1.288. |

15. A method of treating a disease selected from the group consisting of Alzheimer's Disease, Dementia with Lewy Bodies and Dry age-related macular degeneration in a subject in need thereof, comprising treating the subject with 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) comprising characteristic 2θ peaks at 9.69, 16.51, 17.23, 19.02, 25.10, and 26.49° (±0.2°).

16. A process for preparing 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) comprising characteristic 2θ peaks at 9.69, 16.51, 17.23, 19.02, 25.10, and 26.49° (±0.2°), comprising:

a) heating 2-(t-butoxy)-4-(3-methyl-3-(5-(methylsulfonyl)isoindolin-2-yl)butyl)phenol, and fumaric acid in ethanol to form a solution;

b) slowly adding water to the solution of step a) to form a slurry; and c) slowly cooling the slurry to obtain the 2-(t-butoxy)-4-(3-methyl-3-(5-(methylsulfonyl)isoindolin-2-yl)butyl) phenol hemi-fumarate dihydrate salt crystal form E.

17. The process of claim 16, wherein the heating in step a) is a temperature of about 55° C.

18. The process of claim 16, wherein the fumaric acid is 0.5 equivalents (moles) to 1 equivalent (moles) of 2-(t-butoxy)-4-(3-methyl-3-(5-(methylsulfonyl)isoindolin-2-yl) butyl)phenol.

19. The process of claim 16, wherein the solution of step a) is filtered through a cartridge and the solution temperature readjusted to about 50° C. prior to step b).

20. The process of claim 16, wherein the water in step b) is added over a period of about 1 hour.

21. The process of claim 16, wherein the volume of ethanol in step a) to water in step b) is about 90/10 v/v.

22. The process of claim 16, wherein seed crystals of 2-(t-butoxy)-4-(3-methyl-3-(5-(methylsulfonyl)isoindolin-2-yl)butyl)phenol hemi-fumarate dihydrate salt crystal form E are added after addition of water in step b) and prior to step c).

23. The process of claim 22, wherein the seed crystals are added at an amount of about 1% by weight relative to the 2-(t-butoxy)-4-(3-methyl-3-(5-(methylsulfonyl)isoindolin-2-yl)butyl)phenol.

24. The process of claim 16, wherein the slurry is aged at 50° C. for about 90 minutes prior to step c).

25. The process of claim 16, wherein the cooling in step c) is a temperature of about 20° C.

26. The process of claim 16, wherein the slowly cooling takes place over a period of about 11 hours.

27. The process of claim 16, further comprising isolating the 2-(t-butoxy)-4-(3-methyl-3-(5-(methylsulfonyl)isoindolin-2-yl)butyl)phenol hemi-fumarate dihydrate salt crystal form E.

28. The process of claim 27, wherein the isolating comprises filtering the slurry of step c).

29. A process for preparing 2-(t-butoxy)-4-(3-methyl-3-(5-(methylsulfonyl)isoindolin-2-yl)butyl)phenol hemi-fumarate dihydrate salt crystal form E characterized by an X-ray powder diffraction pattern (XRPD) comprising characteristic 2θ peaks at 9.69, 16.51, 17.23, 19.02, 25.10, and 26.49° (±0.2°), comprising:

a) heating 1 equivalent (moles) of 2-(t-butoxy)-4-(3-methyl-3-(5-(methylsulfonyl)isoindolin-2-yl)butyl) phenol, and 0.5 equivalents (moles) of fumaric acid in ethanol at about 55° C. to form a solution;

b) clarifying the solution through a cartridge, collecting the solution and readjusting the temperature of the solution to about 50° C.;

c) adding water to the solution in step b) over a period of about 1 hour, followed by the addition of about 1% of seed crystals to form a slurry, wherein the amount of water added achieves about a 90/10 v/v ethanol to water mixture;

d) aging the slurry of step c) for about 90 minutes at about 50° C.; and e) cooling the slurry of step d) to 20° C. over about 11 hours; to obtain the 2-(t-butoxy)-4-(3-methyl-3-(5-(methylsulfonyl)isoindolin-2-yl)butyl)phenol hemi-fumarate dihydrate salt crystal form E.

30. The process of claim 29, wherein the process further comprises:

f) isolating the 2-(t-butoxy)-4-(3-methyl-3-(5-(methylsulfonyl)isoindolin-2-yl)butyl)phenol hemi-fumarate dihydrate salt crystal form E.

* * * * *